US008772028B2

(12) United States Patent
Zuniga-Pflucker et al.

(10) Patent No.: US 8,772,028 B2
(45) Date of Patent: Jul. 8, 2014

(54) CD34+CD7+CD5+CD1A-HUMAN PROGENITOR T-CELLS PRODUCED IN VITRO AND METHODS OF USING

(75) Inventors: Juan Carlos Zuniga-Pflucker, Toronto (CA); Geneve Awong, Toronto (CA); Ross La Motte-Mohs, Toronto (CA)

(73) Assignee: Sunnybrook Health Sciences Centre, Toronto, Ontario (CA)

( * ) Notice: Subject to any disclaimer, the term of this patent is extended or adjusted under 35 U.S.C. 154(b) by 344 days.

(21) Appl. No.: 13/127,490

(22) PCT Filed: Nov. 6, 2009

(86) PCT No.: PCT/CA2009/001601

§ 371 (c)(1), (2), (4) Date: Jul. 19, 2011

(87) PCT Pub. No.: WO2010/051634

PCT Pub. Date: May 14, 2010

(65) Prior Publication Data

US 2011/0274671 A1 Nov. 10, 2011

Related U.S. Application Data

(60) Provisional application No. 61/112,503, filed on Nov. 7, 2008.

(51) Int. Cl.
*C12N 5/00* (2006.01)
*C12N 15/00* (2006.01)
*C12N 5/0789* (2010.01)
*C12N 5/0783* (2010.01)
*C12N 5/071* (2010.01)

(52) U.S. Cl.
CPC ............ *C12N 5/0647* (2013.01); *C12N 5/0636* (2013.01); *C12N 2501/42* (2013.01); *C12N 2502/21* (2013.01); *C12N 2501/2307* (2013.01); *C12N 5/0663* (2013.01); *C12N 5/0669* (2013.01)
USPC ........... 435/373; 435/377; 435/384; 435/386; 435/372.3; 435/357

(58) Field of Classification Search
CPC ........... C12N 2501/23; C12N 2501/26; C12N 5/0647; C12N 5/0636; C12N 2501/42; C12N 2502/21; C12N 2501/2307; C12N 5/0663; C12N 5/0669
See application file for complete search history.

(56) References Cited

FOREIGN PATENT DOCUMENTS

| | | | |
|---|---|---|---|
| WO | WO01/32841 | A2 | 5/2001 |
| WO | WO2008/101272 | A1 | 8/2008 |

OTHER PUBLICATIONS

Schmitt et al. Induction of T Cell Development by Delta-like-1. Immunity, 2002, vol. 17, pp. 749-756.*
Dalloul et al. Functional and Phenotypic Analysis of Thymic CD34+CD1a-Progenitor-Derived Dendritic Cells: Predominance of CD1a+ Differentiation Pathway. J. Immunology, 1999, vol. 162, pp. 5821-5828.*
Riddell et al. J. Antimicrobial Chemotherapy, 2000, vol. 45, Topic T3, pp. 35-43.*
Sullivan et al. CD4+ CD25+ T-Cell Production in Healthy Humans and in Patientswith Thymic Hypoplasia. Clinical and Vaccine Immunology, 2002, vol. 9, pp. 1129-1131.*
Brentjens et al. Eradication of Systemic B-cell Tumors . . . Nature Med. 2003, vol. 9, pp. 279-286.*
Marquez et al. Identification of a Common Developmental Pathway for Thymic Natural Killer Cells and Dendritic Cells. Blood, 1998, vol. 91, pp. 2760-2771.*
Awong, G. et al., "In vitro human T cell development directed by notch-ligand interactions", Methods in Molecular Biology Humana Press Inc., 999 Riverview Dr., Ste. 208, Totowa, NJ 07512-1165 USA Series: Methods in Molecular Biology, p. 135-142, Jan. 1, 2008.
Awong, G. et al. "Generation of pro-T cells in vitro: potential for immune reconstitution", Seminars in Immunology, LNKD-Pubmed: 17997108, vol. 19, No. 5, p. 341-349, Oct. 2007.
La Motte-Mohs, R.N. "Induction of T-cell development from human cord blood hematopoietic stem cells by Delta-like 1 in vitro", Blood, American Society of Hematology, US, vol. 105, No. 4, p. 1431-1439, Feb. 15, 2005.
Schmitt, T.M. et al. "Induction of T cell development and estabilishment of T cell competence from embryonic stem cells differentiated in vitro", Nature Immunology, Nature Publishing Group GB, vol. 5, No. 4, p. 410-417, Apr. 1, 2004.
La Motte-Mohs et al. In Vitro models of human T cell development: dishing out progenitor T cells. Current Immunology Reviews. 2007, vol. 3, pp. 57-75, ISSN 1573-3955. Whole document.
Imataki, O et al. Limited but potential efficacy by graft-versus-leukemia (GVL) for Pro T-ALL. Gan to kagaku ryoho. Nov. 1, 2008, vol. 35, No. 11, pp. 1911-1914, ISSN 0385-0684. Abstract only.
Haddad, R et al. Dynamics of thymus-colonizing cells during human development. Immunity. 2006, vol. 24, pp. 217-230, ISSN 0167-5699. Whole document.
Liu, C-C et al. The emerging role of IL-15 in NK-cell development. Immunology today. 2000, vol. 21, No. 3, pp. 113-116, ISSN 0167-5699. Whole Document.
Sanchez, MJ et al. Identification of a common T/Natural Killer cell progenitor in human fetal thymus. The Journal of Experimental Medicine. 1994, vol. 180, pp. 569-576, ISSN 0022-1007. Abstract, results.
Timmermans, F et al. Generation of T cells from human embryonic stem cell-derived hematopoietic zones. Journal of Immunology. Jun. 1, 2009, vol. 182, No. 11, pp. 6879-6888, ISSN 0022-1767. Whole document.

(Continued)

*Primary Examiner* — Deborah Crouch
(74) *Attorney, Agent, or Firm* — Bereskin & Parr LLP/S.E.N.C.R.L., s.r.l.; Micheline Gravelle

(57) ABSTRACT

Human progenitor T cells that are able to successfully engraft a murine thymus and differentiate into mature human T and NK cells are described The human progenitor T cells have the phenotype CD34+CD7+CD1a−CD5− or CD34+CD7+CD1a−CD5+ and are derived from human hematopoietic stem cells, embryonic stem cells and induced pluripotent stem cells b\ coculture with cells expressing a Notch receptor ligand (OP9-DL1 or OP9-DL4) Such cells are useful in a variety of applications including immune reconstitution, the treatment of immunodeficiencies and as carriers for genes used in gene therapy.

9 Claims, 27 Drawing Sheets

(56) References Cited

OTHER PUBLICATIONS

Awong, G et al. Characterization in vitro and angraftment potential in vivo of human progenitor T cells generated from hematopoietic stem cells. Blood. Jun. 2, 2009, vol. 114, No. 5, pp. 972-982, ISSN 1528-0020. Whole document.

Traggiai, E. et al. "Development of a human adaptive immune system in cord blood cell-transplanted mice", Science, 2004, 304,104-7.

* cited by examiner

A
d0
d4
d6
d8
d10
d12
CD45RA
CD7
26.7
0.42
0
13.5
28.9
48.9
8.72
13.3
60.1
21.5
5.18
7.63
85.6
4.2
2.6
3.17
85.6
1.14
10.1
4.72
88.1
1.95
5.24
B
CD34
CD7
26.1
51.3
42
RCN
CD45RA
gated CD34+CD7++

Thymus: flow cytometric analysis of cell surface markers

Thymus: flow cytometric analysis of cell surface markers

Thymus: flow cytometric analysis of cell surface markers

In vivo experiment, Repeat #2, 1 mouse proT , 1 mouse HSC

Figure 16. Engraftment potential of in vitro-derived proT cells in NOD/SCID $\gamma_c^{-/-}$ mice proT1
proT2
OP9-control (NK conditions)
OP9-DL1
6.15
57.7
31.3
4.87
8.15
79.4
7.75
4.71
0.052
0.37
3.29
96.3
0.037
0.9
3.66
95.4
CD56
CD7

Figure 24
A
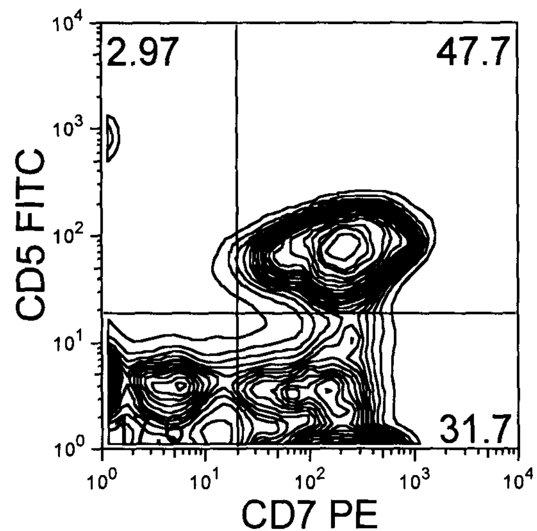
B
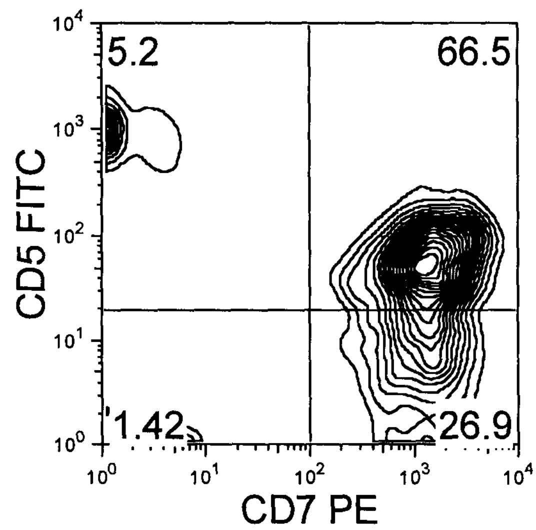

```
                          SEQUENCE LISTING

<160> NUMBER OF SEQ ID NOS: 24

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1

caaccaaatt gcagacatct caac                                              24


<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2

ccatgctggc tgaggtacct                                                   20


<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3

gtgagcaaga gcgacgtgaa g                                                 21


<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4

accacatcct cgggattctt act                                               23


<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5

cgggtccacc agtttgaatg                                                   20


<210> SEQ ID NO 6
<211> LENGTH: 21
<212> TYPE: DNA
<213> ORGANISM: Artificial Sequence
<220> FEATURE:
```

<223> OTHER INFORMATION: Primer

<400> SEQUENCE: 6
gttgtattgg ttcggcacca t 21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
gatggcacgg gacactacct 20

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
gctctcctgg ctgcagaca 19

<210> SEQ ID NO 9
<211> LENGTH: 19
<212> TYPE: DNA
<213> ORGANISM: Artificial Sequence
<220> FEATURE:
<223> OTHER INFORMATION: Primer

<400> SEQUENCE: 9
cggacttggt gcgtctaag 19

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gaggcaggaa acctccaaat 20

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
tgtcccaggg agagttgca 19

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gggtgtcatg gtgggtcagt 20

<210> SEQ ID NO 13
<211> LENGTH: 19
<212> TYPE: DNA
<213> ORGANISM: Artificial Sequence
<220> FEATURE:
<223> OTHER INFORMATION: Primer

<400> SEQUENCE: 13
gtgccatgcc tctgcaact 19

<210> SEQ ID NO 14
<211> LENGTH: 19
<212> TYPE: DNA
<213> ORGANISM: Artificial Sequence
<220> FEATURE:
<223> OTHER INFORMATION: Primer

<400> SEQUENCE: 14
tgtcccacag ctgcaagct 19

<210> SEQ ID NO 15
<211> LENGTH: 22
<212> TYPE: DNA
<213> ORGANISM: Artificial Sequence
<220> FEATURE:
<223> OTHER INFORMATION: Primer

<400> SEQUENCE: 15
tctgagactg ccaaggtctt ca 22

<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
cagctggtat ttgtcggaca tc 22

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
aagctgactg ttcatgggtt tgt 23

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tctccaccat gcacgtttca 20

<210> SEQ ID NO 19
<211> LENGTH: 20
<212> TYPE: DNA
<213> ORGANISM: Artificial Sequence
<220> FEATURE:
<223> OTHER INFORMATION: Primer -continued

<400> SEQUENCE: 19
cagtgccgag ttcaccaaga 20

<210> SEQ ID NO 20
<211> LENGTH: 22
<212> TYPE: DNA
<213> ORGANISM: Artificial Sequence
<220> FEATURE:
<223> OTHER INFORMATION: Primer

<400> SEQUENCE: 20
gccttgccag aaatagcttc ct 22

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
tcagaattgg atttggctca ttt 23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
cctgagctta gctggtgttg tg 22

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ttgccgacag gatgcagaa 19

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gccgatccac acggagtact 20

CD34+CD7+CD5+CD1A-HUMAN PROGENITOR T-CELLS PRODUCED IN VITRO AND METHODS OF USING

CROSS-REFERENCE TO RELATED APPLICATIONS

The present application is a national phase entry application of PCT/CA2009/001601 which claims priority to U.S. provisional patent application No. 61/112,503 filed Nov. 7, 2008, both of which are incorporated herein by reference in their entirety.

INCORPORATION OF SEQUENCE LISTING

A computer readable form of the Sequence Listing "20925-36_SequenceListing.txt" (4,864 bytes), submitted via EFS-WEB and created on Apr. 29, 2011, is herein incorporated by reference.

FIELD

The application relates to progenitor T cells, methods of preparing same, and all uses of the progenitor T cells including the use of the T cells to create mature human T-cell populations, to engraft into thymus tissue and in therapeutic applications.

BACKGROUND

T cells are the major cellular arm of the immune system that elicit potent and specific immune responses in vivo against bacterial and viral antigens. Individuals born with severe combined immunodeficiency (SCID) exhibit a complete absence of T cells, while individuals infected with HIV/AIDS or treated for cancer with chemo/radio-therapy exhibit a profound depletion of T cells. Regardless of whether the immunodeficiency is congenital or acquired, these individuals are compromised in their capacity to generate new T cells from incoming bone marrow-derived stem cells and to mount sufficient immune responses against opportunistic infections. Conversely, individuals with certain autoimmune diseases such as arthritis and diabetes exhibit inappropriate immune responses against self-tissue due in part to an absence of a particular kind of T cell termed T-regulatory cells. Thus, the ability to generate new designer T cells in vitro through the differentiation of expanded progenitor cells extracted from a particular individual may offer therapeutic benefits in the treatment of many diseases by restoring T cell numbers and the capacity to maintain and regulate a functional immune system. An in vitro differentiation system in which mouse hematopoietic stem cells are induced to differentiate towards a T cell lineage following a period of coculture with the mouse OP9 bone marrow stromal cell line that expresses the Notch receptor ligands Delta-like-1 or -4 has been described, however, the characterization human hematopoietic stem cells using the same system has yet to be elucidated.

Hematopoietic stem cells (HSCs) which give rise to erythroid, myeloid, and lymphoid lineages, can be identified based on the expression of CD34 and the absence of lineage specific markers (termed Lin−) (Kawamoto et al., 1997). Human umbilical cord blood (CB) provides a rich source of HSCs, which are comparable to bone marrow-derived HSCs (Barker and Wagner, 2003; de Wynter et al., 1999; Fisher et al., 1990; Galy et al., 1993; Gluckman et al., 1997; Ito et al., 2002; Lewis and Verfaillie, 2000; McCune et al., 1991; Sanchez et al., 1993; Wilpshaar et al., 2002). Human T cells differentiate in the thymus via discrete developmentally-regulated steps that involve a series of commitment events and developmental checkpoints including T cell receptor (TCR) variable (V), diversity (D), and joining (J) gene segment rearrangements [V(D)J], and positive/negative selection of developing thymocytes (Spits, 2002). The earliest intrathymic progenitors express high levels of CD34 and CD7, do not express CD1a, and are triple-negative (TN) for mature T cell markers: CD4, CD8, and CD3 (Galy et al., 1993). Commitment to the T cell lineage is associated with the expression of CD1a by CD7-expressing pro-thymocytes (Spits, 2002; Spits et al., 2000).

Several studies have implicated the Notch pathway in promoting HSC expansion, self-renewal (Stier et al., 2002), survival (Deftos and Bevan, 2000; Osborne and Miele, 1999), and the induction of T cell lineage commitment (MacDonald et al., 2001; Osborne and Miele, 1999; Pear and Radtke, 2003; Radtke et al., 2002; Robey, 1999; von Boehmer, 2001). In humans there are four Notch receptors (Ellisen et al., 1991; Lardelli et al., 1994; Milner et al., 1994; Uyttendaele et al., 1996; Weinmaster et al., 1991), which can pair with two serrate like ligands (Jagged 1 & 2) (Lindsell et al., 1995; Luo et al., 1997) or three delta-like-ligands (DII-1, -3 & -4) (Karanu et al., 2001; Shutter et al., 2000) Notch signaling appears to act at multiple stages of T cell differentiation (Deftos et al., 2000; Garcia-Peydró et al., 2003; Izon et al., 2001; Jiang et al., 1998; Robey et al., 1996; Washburn et al., 1997) The strongest evidence for the role of Notch signaling in T cell development comes from gain-of-function and loss-of-function studies (Allman et al., 2002; Izon et al., 2002; MacDonald et al., 2001; Pear et al., 1996; Pui et al., 1999; Radtke et al., 2002; Wilson et al., 2001), in which signaling though Notch-1 was shown to play a crucial role in determining the B cell versus T cell lineage choice (Pear and Radtke, 2003; Radtke et al., 2002).

HSCs express multiple Notch receptors (Milner et al., 1996; Milner et al., 1994) but the expression patterns of the various Notch ligands have been reported to be distinct between bone marrow stromal cells (Jones et al., 1998; Karanu et al., 2001; Li et al., 1998; Varnum-Finney et al., 1998; Walker et al., 1999) and thymic epithelial cells (Anderson et al., 2001) Taken together, these results suggest that different Notch receptors and ligands may control different aspects of hematopoiesis depending on the micro-environment: allowing for self-renewal in the bone marrow and influencing cell fate decisions in the thymus (Varnum-Finney et al., 1998). This led to the hypothesis that bone marrow stromal lines, such as OP9 cells (Cho et al., 1999; Kim et al., 2003; Kodama et al., 1994), which support B cell differentiation may do so because the appropriate Notch ligand to induce T cell commitment and differentiation is absent. This hypothesis was tested, and demonstrated that OP9 cells, which do not express DII1, when retrovirally-transduced to express DII-1 (OP9-DL1) inhibited the development of B cells and favored the development of T cells from fetal liver-derived HSCs (Schmitt and Zúñiga-Pflücker, 2002) or mouse ESCs (Schmitt et al., 2004). Given the high level of homology (90%) between mouse and human DII-1 molecules, and the observation that mouse stromal lines can support the differentiation of human HSCs (Bennaceur-Griscelli et al., 2001; Jaleco et al., 2001; Karanu et al., 2001; Rawlings et al., 1995), the inventors sought to determine whether human CB-derived HSCs ($CD34^+CD38^-$) cultured on OP9-DL1 cells could initiate and support T cell differentiation in vitro.

T-cells develop within the thymus from bone marrow-derived hematopoietic progenitors, and follow a series of stage-specific differentiation events, which are broadly characterized by the developmentally-coordinated expression of CD4 and CD8 (Blom and Spits, 2006; Spits, 2002).

The initial stages of human T-cell development include precursors that express the stem cell marker CD34 (Haddad et al., 2006; Hao et al., 2001), which is also present on hematopoietic stem cells (HSCs) and on multipotent or lineage-specified progenitor cells. Furthermore, several groups have established that the most primitive cells in the human thymus possess multi-lineage potential (Blom et al., 1997; Res et al., 1996; Weerkamp et al., 2006a) as they give rise to T-lineage, as well as, natural killer (NK), dendritic cells (DCs) and to some extent myeloid-lineage cells (Blom et al., 1997; La Motte-Mohs et al., 2007). Within the known hierarchy of T-cell development, the earliest precursor subset is further defined by their lack of CD3, CD4, CD8 and CD1a expression (Galy et al., 1993; Vanhecke et al., 1995).

While immature stages of T-cell development are typically delineated as $CD34^+CD1a^-$ (most immature) and $CD34^+$ $CD1a^+$ cells, these populations remain heterogeneous. Of note, CD7 expression is one of the earliest cell surface markers known to appear during T-lymphopoiesis (Haddad et al., 2006; Haynes et al., 1988). Importantly, the transition from $CD34^+CD7^+CD1a^-$ to $CD34^+CD7^+CD1a^+$ by early thymocytes is associated with T-cell commitment, as a small percentage (~10%) of these cells bear rearrangement at the T-cell receptor β-chain (TCRβ) locus (Blom et al., 1999; Dik et al., 2005). In addition, $CD34^+CD7^+CD1a^+$ cells appear to be T-lineage restricted, as these cells show low precursor activity towards non-T-cell lineages (Spits, 2002). Following this stage, thymocytes progress to a CD4 immature single positive (CD4ISP) stage, at which point CD4 is expressed in the absence of CD8. Thereafter, a subset of CD4ISP cells are thought to complete TCRβ rearrangement leading to β-selection and differentiation to the $CD4^+CD8^+$ double positive (DP) stage. Finally, following TCRα rearrangement, TCRαβ-expressing DP thymocytes undergo positive and negative selection, and yield $CD4^+CD8^-$ and $CD4^-CD8^+$ single positive (SP) T-cells, which emigrate to the periphery (Vanhecke et al., 1997).

Current understanding of the above-outlined stages has been obtained from analyses of human fetal or adult thymocyte subsets, and by analyzing T-cell development in vitro using xenogeneic engraftment of mouse fetal thymus organ cultures (FTOCs) (Fisher et al., 1990; La Motte-Mohs et al., 2007). While these systems have provided important insight into T-cell development, the capacity to evaluate specific progenitor populations has remained difficult to assess given the requirement of human thymus tissue, and the limited number of progenitor T-cells that can be readily analyzed.

Previous work from the inventors' laboratory established that human T-lineage differentiation can be induced from umbilical cord-blood (UCB)-derived HSCs cocultured with OP9-DL1 cells (La Motte-Mohs et al., 2005). The inventors showed normal stage-specific expression of various cell surface molecules, including the generation of immature DP T-lineage cells. However, these studies were not performed using quantitative clonal analyses, and it was unresolved whether different UCB $CD34^+$ subsets could give rise to T-lineage cells and whether Delta-like/Notch signals influence the T-progenitor frequency of $CD34^+$ UCB cells. Additionally, it was unclear whether functional T-cells could be generated. Finally, the inventors' initial studies (La Motte-Mohs et al., 2005) showed that during the early stages of HSC/OP9-DL1 differentiation a population of cells resembling T-progenitors became apparent, however the potential of these cells to serve as effective T-cell progenitors was not addressed.

SUMMARY

The inventors examined the early stages of human T-cell development in vitro, and performed limiting dilution and single-cell assays to address the T-cell progenitor frequency of various UCB-derived $CD34^+$ stem/progenitor subsets. The inventors assessed the effect of Delta-like/Notch interactions in enhancing T-cell progenitor potential among Notch-signaled $CD34^+$ subsets. Furthermore, using limiting dilution thymus-reconstitution approaches, the inventors findings revealed that different tissue culture-derived T-progenitor subsets vary in their thymus-engrafting effectiveness, although these cells display a similar potential to give rise to T-lineage cells when assayed on OP9-DL1 cells. In particular, two distinct subsets, $CD34^+$ $CD7^{++}$ $CD5^-$ $CD1a^-$ (proT1) and $CD34^+$ $CD7^{++}$ $CD5^+$ $CD1a^-$ (proT2) were analyzed. The inventors also showed that mature functional T-cells are generated in vitro, and that these cells upon TCR-stimulation display T-cell effector-function. The pro-T cells can also give rise to natural killer (NK) cells when cultured with IL-15.

Together, these findings support the use of the progenitor T cells (pro-T cells) for the generation and study of human T-cells and NK cells, and provide support for the use of in vitro-generated pro-T cells, mature T-cells and NK cells in cell-based immune-reconstitution approaches.

Accordingly, one aspect of the present application provides an isolated progenitor T cell having the phenotype $CD34^+$ $CD7^+CD1a^-$. In one embodiment, the isolated progenitor T cell has the phenotype $CD34^+CD7^+CD5^-CD1a^-$. In another embodiment, the isolated progenitor T cell has the phenotype $CD34^+CD7^+CD5^+CD1a^-$.

In another aspect, the present application provides a pharmaceutical composition comprising an isolated progenitor T cell in admixture with a suitable diluent or carrier.

In another aspect, the present application provides the use of the human progenitor T cells in all applications, including preparing mature T cells, preparing NK cells, engrafting a thymus, immune reconstitution, the treatment of conditions requiring an increase in T cells as carriers for genes used in gene therapy.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

Advantages of the present application can be readily appreciated as the same becomes better understood by reference to the following detailed description when considered in connection with the accompanying drawings. The following is a brief description of the drawings, which are presented only for the purposes of further illustrating the applications and not for the purposes of limiting the same.

NOD/SCID $\gamma c^{-/-}$ Figure Legend

Figure 16:
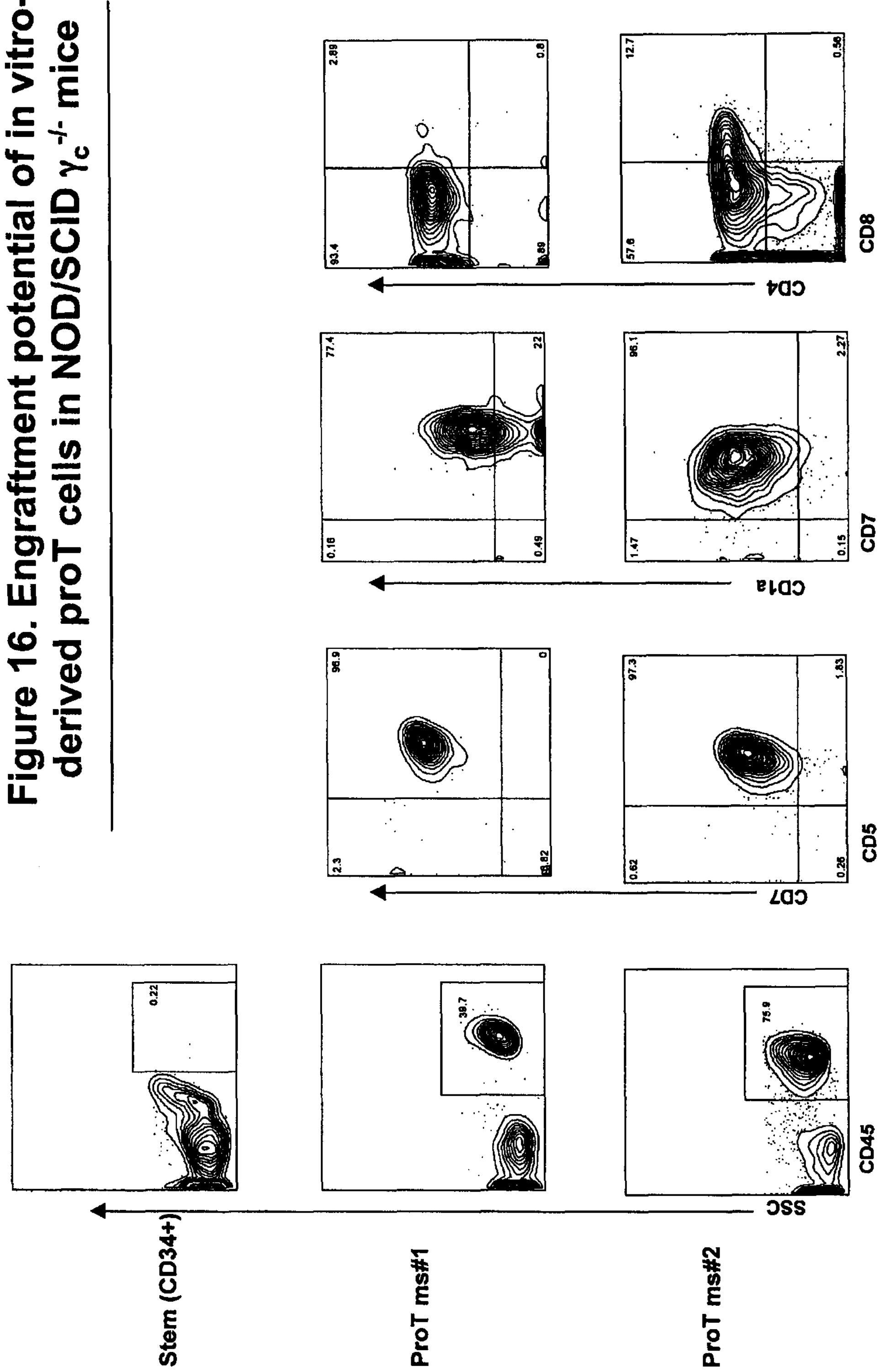

FIG. 16. Flow cytometric analysis of thymuses from NOD/SCID $\gamma c^{-/-}$ mice receiving either $CD34^+$ HSCs or $CD34^+$ $CD7^+$ progenitor T cells. Following live lymphocyte gating, cells were analyzed for the expression of CD7, CD5, CD1a, CD4 and CD8 expression after SSC and human CD45 gating. Numbers in plots indicate percentage of cells within each quadrant.

Figure 17:
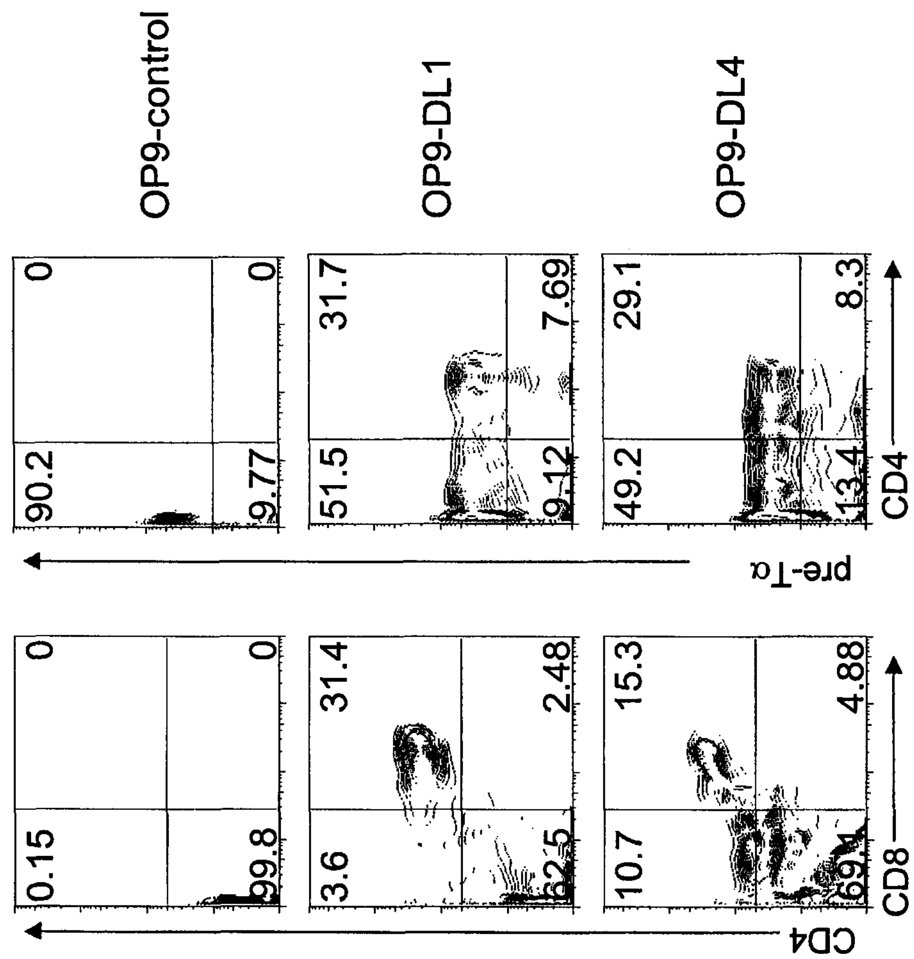

FIG. 17. Flow cytometric analysis of human HSCs induced to differentiate on OP9-control, OP9-DL1 and OP9-DL4 cells. Following live lymphocyte gating, day 24 cocultured cells were analyzed for the expression of CD4, CD8, and pre-Tα expression. Numbers in plots indicate percentage of cells within each quadrant.

Figure 18:
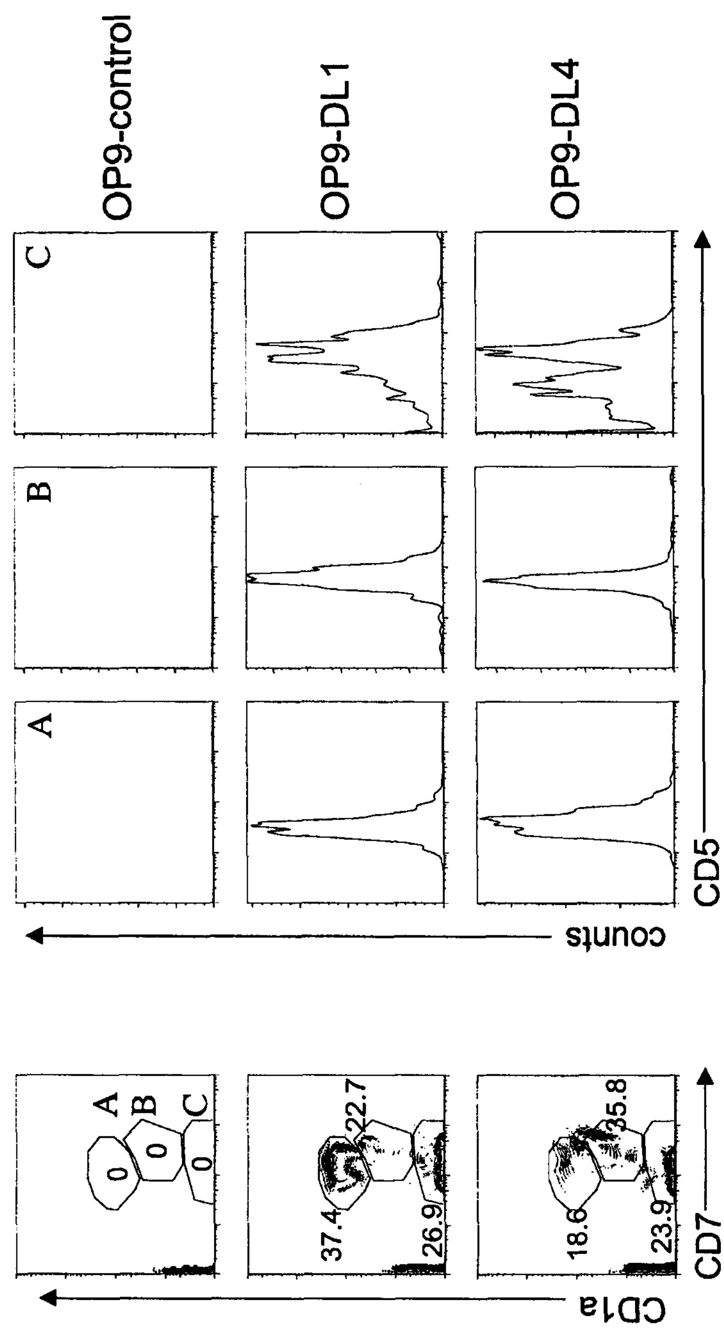

FIG. 18. Flow cytometric analysis of human HSCs induced to differentiate on OP9-control, OP9-DL1 and OP9-DL4 cells. Following live lymphocyte gating, day 24 cocultured cells were analyzed for the expression of CD7, CD1a, and CD5 (right 3 columns) expression. Gated on T cell populations (left column) corresponding to (A) $CD7^+CD1a^{++}$ (more mature T cells), (B) $CD7^{++}CD1a^+$ (committed T cells), and (C) $CD7^{++}CD1a^-$ (progenitor T) and were examined for CD5 (right 3 columns) expression in each of the corresponding populations labeled as A, B or C. Numbers in plots indicate percentage of cells within each gated population.

Figure 19:
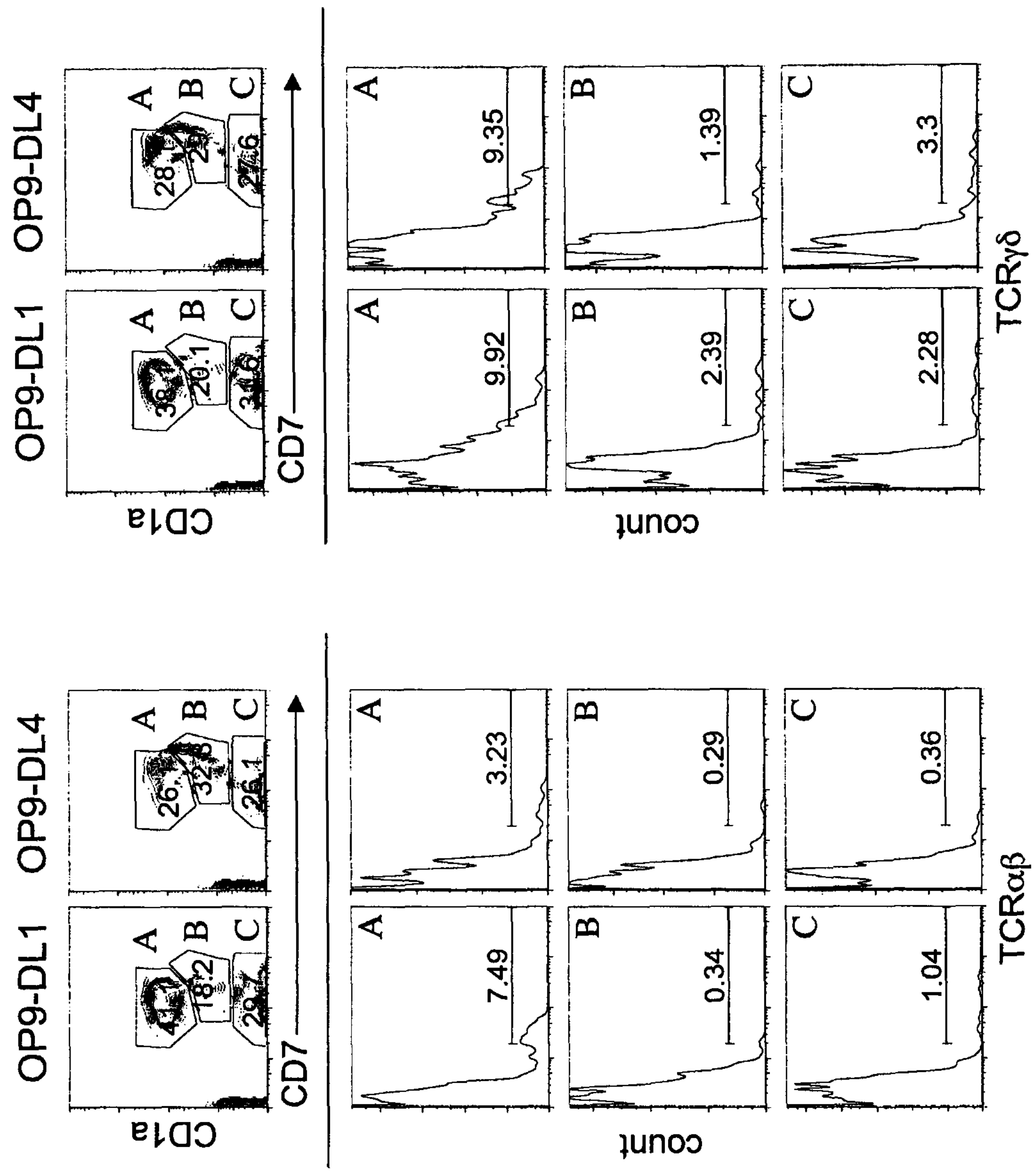

FIG. 19. Flow cytometric analysis of human HSCs induced to differentiate towards the T lineage upon coculture with OP9-DL1 and OP9-DL4 cells. Following live lymphocyte gating, day 40 cocultured cells were analyzed for the expression of CD7, CD1a, TCR-αβ, and TCR-γδexpression. Gated on T cell populations (top row) corresponding to (A) $CD7^+$ $CD1a^{++}$ (more mature T cells), (B) $CD7^{++}CD1a^+$ (committed T cells), and (C) $CD7^{++}CD1a^-$ (progenitor T) were examined for TCR-αβ (left panel, bottom 3 rows), and TCR-γδ (right panel, bottom 3 rows) expression in each of the corresponding populations labeled as A, B or C. Numbers in plots indicate percentage of cells of positive cells within each gated population.

Figure 20:
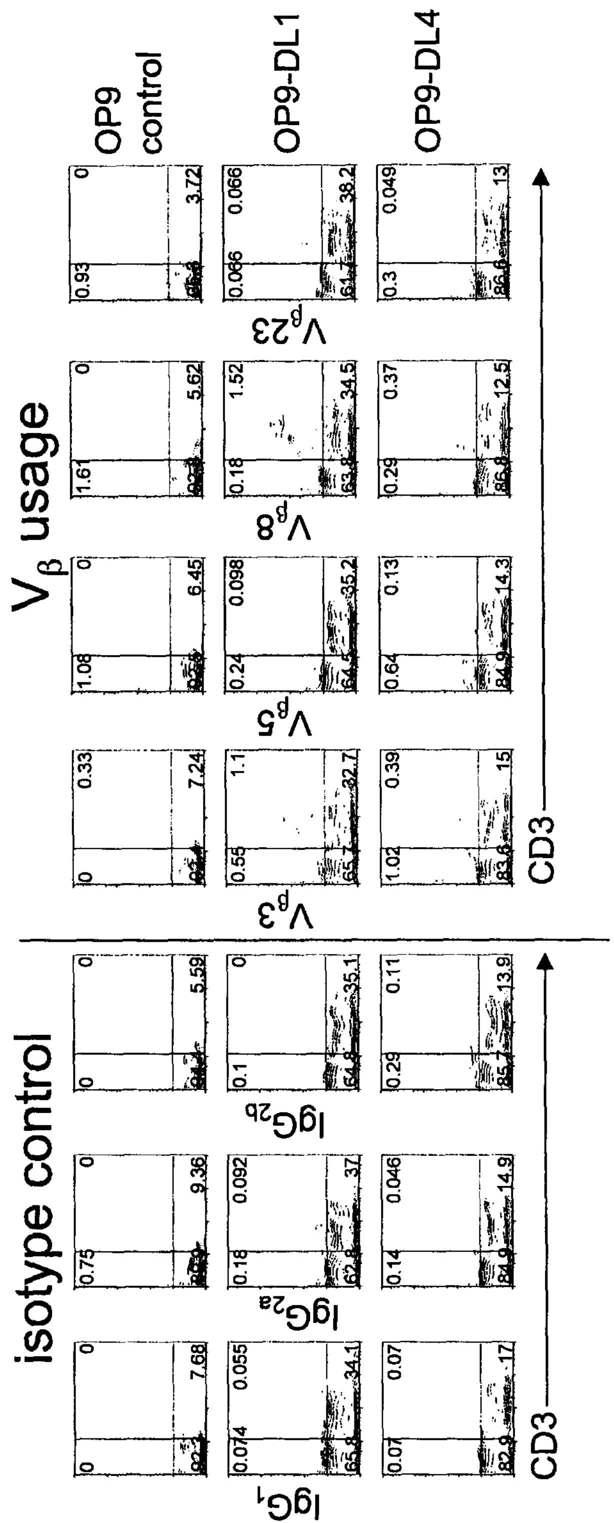

FIG. 20. Flow cytometric analysis of human HSCs induced to differentiate on OP9-control, OP9-DL1 and OP9-DL4 cells. Following live lymphocyte gating, day 40 cocultured cells were analyzed for the expression of CD3, V-beta ($V_\beta$)-3, 5, 8, 23 (right panel). Corresponding isotype controls are shown (left panel). Numbers in plots indicate percentage of cells within each quadrant.

Figure 21:
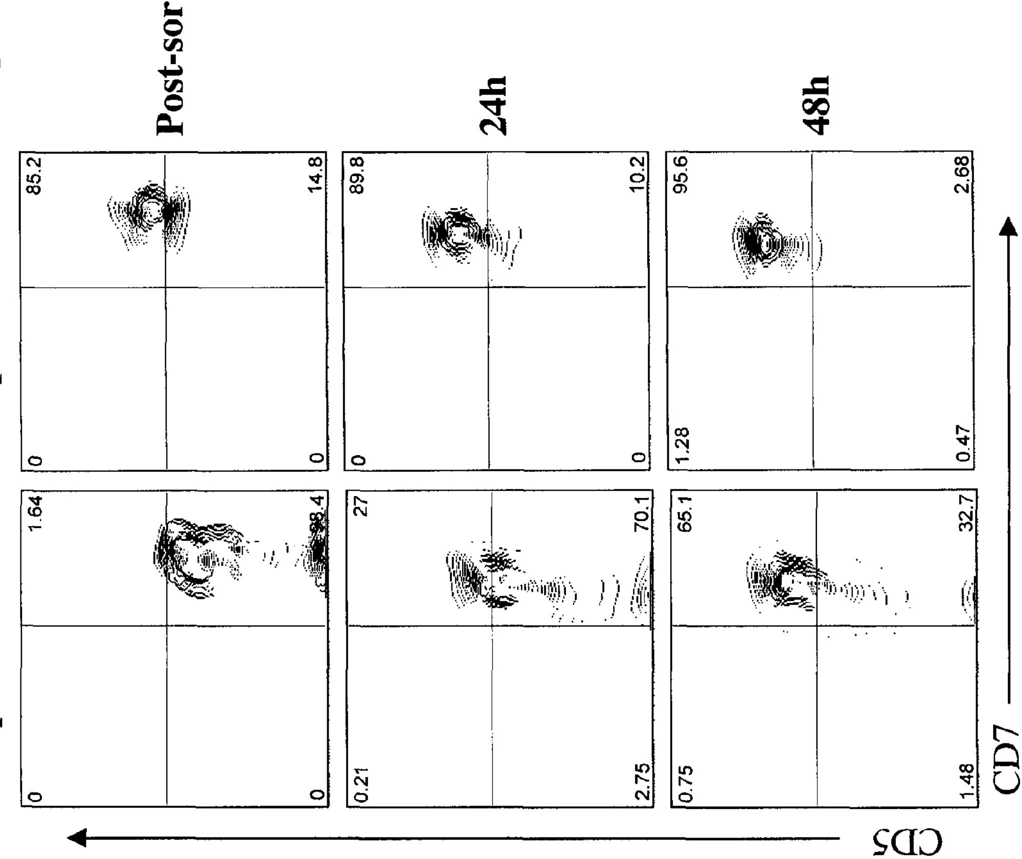

FIG. 21. ProT1 cells directly give rise to proT2 cells in vitro. Flow cytometric analysis of $CD34^+$ $CD7^{++}$ $CD5^-$ (proT1) and $CD34^+$ $CD7^{++}$ $CD5^+$ (proT2) cells. Left-side panels, sorted in vitro-generated-proT1 cells were placed onto OP9-DL1 cells and the acquisition of cell surface CD5 was examined at the indicated time points. Right-side panels, as a control, proT2 were sorted and re-cultured on OP9-DL1 cells. All plots shown were gated for $CD34^+$ $CD7^{++}$ expression for the analysis.

Figure 22:
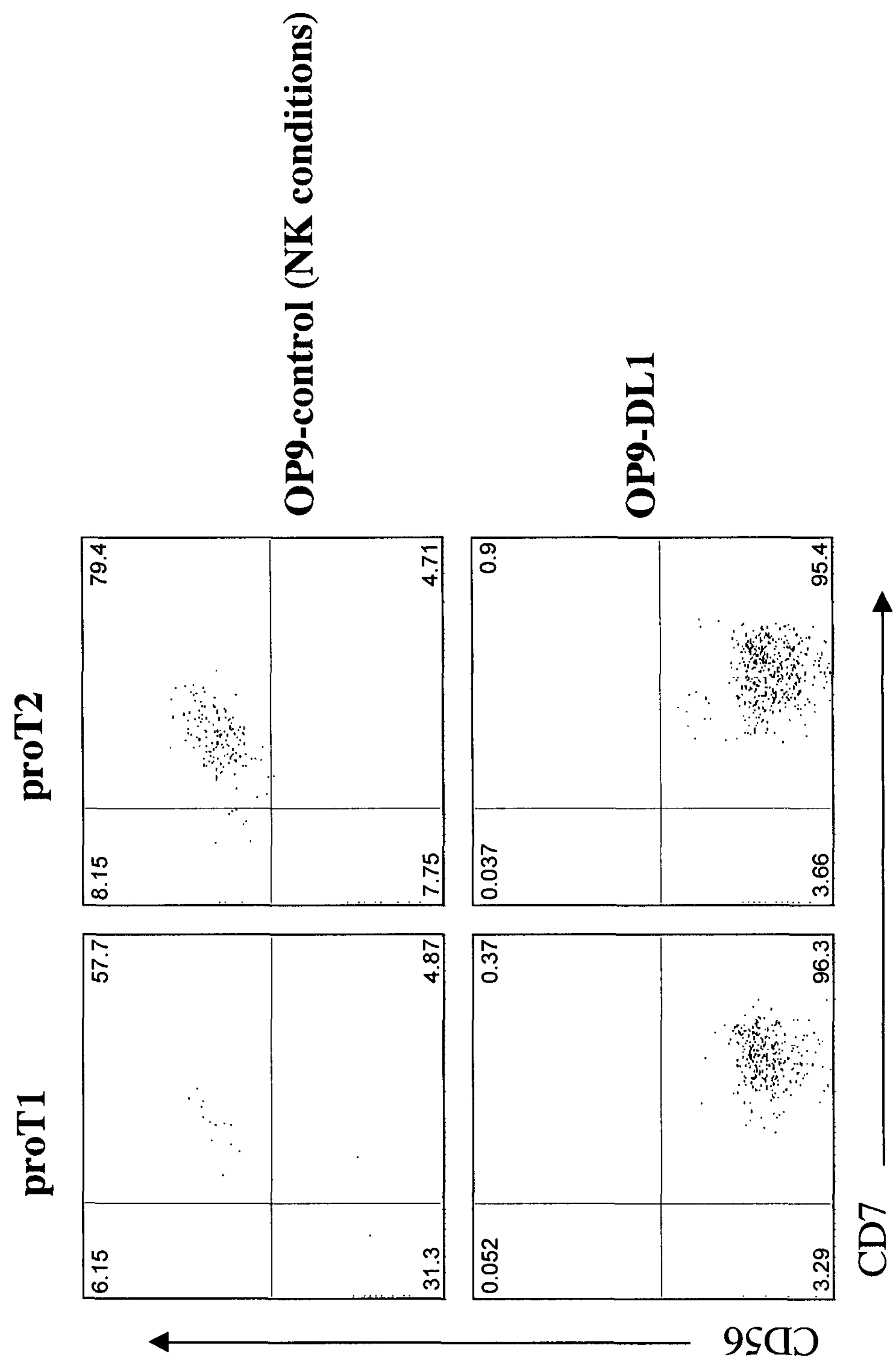

FIG. 22. Natural killer (NK) cell differentiation potential of $CD34^+$ $CD7^{++}$ $CD5^-$ (proT1) and $CD34^+$ $CD7^{++}$ $CD5^+$ (proT2) cells. Sorted proT1 and proT2 cells from a day 10 HSC/OP9-DL1 coculture were placed onto OP9-control cells supplemented with rhIL-15 (5 ng/mL); or proT1 and proT2 cells were placed back onto OP9-DL1 cells. The expression of the NK cell lineage marker CD56 was examined after 12 days of culture.

FIG. 23. Human proT2 cells effectively engraft the thymus of immunodeficient mice and facilitate thymic engraftment of UCB-derived HSCs. Analysis of thymus engraftment and differentiation of HSCs coinjected with in vitro-derived proT2 cells into immunodeficient mice. Human UCB $CD34^+$ $CD38^{-/lo}$ (HLA-$A2^-$) cells were differentiated on OP9-DL1 cells for 10-12 days, and $CD34^+$ $CD7^{++}$ $CD5^+$ (proT2) cells were sorted by flow cytometry. On the same day that proT2 cells were sorted, human UCB $CD34^+$ $CD38^{-/lo}$ (HLA-$A2^+$) cells were also sorted. Irradiated (130 cGy) neonatal NOD/SCID/$\gamma c^{null}$ mice from the same litter were injected intrahepatically with $3.5\times10^4$ HSCs; $2.5\times10^5$ proT2 cells; or $3.5\times10^4$ HSCs mixed with $2.5\times10^5$ proT2 cells. Bone marrow (BM), spleen and thymuses were harvested 6 weeks after injection, single cell suspensions were obtained and analyzed by flow cytometry. The analysis was performed by gating for human $CD45^+$ cells and donor cell type (HSC-derived-$A2^+$, or proT2-derived-$A2^-$), based on the absence (proT2-derived) or presence (HSC-derived) of HLA-A2 expression on $CD45^+$ cells. Flow cytometric analysis for cell surface expression of CD45 and HLA-A2 of (A) BM and (B) spleens from HSC only, HSC+proT2, and proT2 only, treated mice are shown. The lower rows show CD19 and CD33 cell surface staining on $CD45^+$ HLA-$A2^+$ (second row; HSC-derived) and $CD45^+$ HLA-$A2^-$ (third row; proT2-derived) gated cells. (C) Flow cytometric analysis for cell surface expression of CD45 and HLA-A2 of thymuses from HSC only, HSC+proT2, and proT2 only, treated mice are shown. The upper row displays CD45 and HLA-A2 cell surface staining. The lower rows show CD45 and CD3 cell surface staining on $CD45^+$HLA-$A2^+$ (second row; HSC-derived) and $CD45^+$ HLA-$A2^-$ (third row; proT2-derived) gated cells. (D) Flow cytometric analysis of thymuses from HSC+proT2 coinjected mice. The upper row displays CD45 and HLA-A2 cell surface staining. The lower rows show CD8 and CD4 cell surface staining on $CD45^+$ HLA-$A2^+$ (second row; HSC-derived) and $CD45^+$ HLA-$A2^-$ (third row; proT2-derived) gated cells.

FIG. 24. Human ESCs and human iPSCs can generate early human T-lineage progenitor cells upon coculture with OP9-DL1 or OP9-DL4 cells. (A) Using the two-stage protocol method (see text for details), $CD34^{++}$ cells sorted from embryoid bodies, were placed onto OP9-DL1 cells and examined for cell surface expression of CD5 and CD7 after 20 days of culture; and, (B) human iPSCs aggregated to form embryoid bodies were sequentially induced to differentiate towards the hematopoietic lineage, sorted $CD34^{++}$ cells were placed onto OP9-DL4 cells and analyzed for the expression of CD7 and CD5 by flow cytometry as indicated.

DETAILED DESCRIPTION

T cell development is known to follow a defined set of stage-specific differentiation steps. However, the molecular and cellular events occurring at early stages of human T-cell development have not previously been fully elucidated. To address this, human umbilical cord blood (UCB)-derived hematopoietic stem cells (HSCs) were induced to differentiate to the T-lineage by coculture with OP9-DL1 cells. A developmental program was revealed that is highlighted by an early, sequential and temporally discrete expression of CD34, CD7, CD45RA, CD5, CD1a, CD2, and CD4. Quantitative clonal analyses demonstrated that $CD34^+$ $CD38^-$ and $CD34^+$ CD38$^{lo}$ subsets of UCB cells contain a similarly high T-cell progenitor frequency of 1 in 4 cells, while the frequency in CD34$^{+}$ CD38$^{+/hi}$ cells was 5-fold lower. To address whether Delta-like/Notch-induced signals can affect the T-cell progenitor frequency of UCB CD34$^{+}$ CD38$^{-/lo}$ cells differentiated on OP9-DL1 cells, two distinct subsets, CD34$^{+}$ CD7$^{++}$ CD5$^{-}$ CD1a$^{-}$ (proT1) and CD34$^{+}$ CD7$^{++}$ CD5$^{+}$ CD1a$^{-}$ (proT2) were analyzed, and both subsets showed a 2-fold increase in frequency. The inventors established that these progenitor subsets are able to successfully engraft a mouse thymus and differentiate into CD4 and CD8 human T-cells in vitro. Surprisingly, the in vitro-generated proT2 cells showed a 3-fold enhanced thymus-engrafting capacity in vitro than the more immature proT1 progenitor subset. The proT2 cells also showed an almost 3-fold enhancement in thymus-engrafting capacity in vivo than the proT1 cells. Further analysis of these subsets showed that proT2 cells express higher levels of CCR9, PSGL-1 and key integrins than proT1 cells, which may allow for the enhanced engrafting ability. Moreover, the inventors also demonstrate that human HSC/OP9-DL1 cocultures support the generation of mature functional αβ-T cell receptor/CD3$^{+}$ CD8 T-cells. Further, in the presence of IL-15, the proT cells can generate natural killer (NK) cells. In addition to human hematopoietic stem cells, the proT cells can also be generated from embryonic stem cells and induced pluripotent stem cells. Lastly, the inventors have extended the in vitro studies that demonstrate thymus reconstitution ability within FTOC, towards in vivo models that show human thymic reconstitution within immodeficient strains of mice through intrahepatic injection of progenitor-T cells. Taken together, the generation and identification of defined in vitro-generated T-progenitor subsets, which are readily differentiate into functionally mature T-cells and NK cells in vitro and engraft both in FTOC (in vitro) and immunodeficient mice (in vivo), may offer important avenues to improve cellular based immune-reconstitution approaches for the treatment of immunodeficiencies.

I. Progenitor T Cells

Generally, the present application provides isolated progenitor T-cells.

In one aspect, the present application provides an isolated human progenitor T cell having the phenotype CD34$^{+}$CD7$^{+}$ CD1a$^{-}$. In one embodiment, the isolated progenitor T cell has the phenotype CD34$^{+}$ CD7$^{+}$CD5$^{-}$CD1a$^{-}$ (pro-T1). In another embodiment, the isolated progenitor T cell has the phenotype CD34$^{+}$ CD7$^{+}$CD5$^{+}$CD1a$^{-}$ (pro-T2). In a specific embodiment, the pro-T2 cells express CCR9, PSGL-1 and integrins.

The term "isolated" as used herein means that the progenitor cell has been separated or purified from cellular or biological material found with the cells in their native environment. It thus distinguishes the cells from how they exist in nature.

The term "a cell" or "the cell" includes a plurality of cells.

The term "progenitor T cell" or "pro-T cell" as used herein means a T cell that is capable of maturing into a mature T cell or lymphocyte. A mature T cell includes CD4$^{+}$ and CD8$^{+}$ T cells. A lymphocyte includes CD56+ NK cells.

The progenitor T cell is preferably human and derived from a stem cell or progenitor cell. Stem or progenitor cells may be obtained from any suitable source, including, without limitation, umbilical cord, blood, embryos, embryonic tissue, fetal tissue, bone marrow and blood. In one embodiment, the stem or progenitor cell is a hematopoietic stem or progenitor cell. In another embodiment, the stem cell is an embryonic stem cell. In a further embodiment, the stem cell is an induced pluripotent stem cell. For therapeutic applications, the stem cells or progenitor cells used to generate the progenitor T cells may be preferably obtained from the patient to be treated.

Progenitor T cells may be isolated from the stem or progenitor cells by techniques known in the art. Typically, a sample containing the cells is first depleted with non-stem cells or mature cells.

Negative and positive selection methods known in the art may be used for enrichment of the progenitor cells. For example, cells can be sorted based on cell surface antigens using a fluorescence activated cell sorter, or magnetic beads which bind cells with certain cell surface antigens. Negative selection columns can be used to remove cells expressing lineage specific surface antigens.

In an embodiment, a sample containing stem or progenitor cells is separated into lineage-negative (Lin$^{-}$) and lineage position (Lin$^{+}$) fractions. The Lin− fraction can be sorted for CD34$^{+}$ cells.

The enriched progenitor cells or stem cells are cultured under suitable conditions to generate pro-T cells. Preferably, the cells are cultured in the presence of one or more Notch ligand for a sufficient time to form pro-T cells. More preferably, the stem cells are cultured in the presence cells expressing a Notch ligand. This is described in greater detail in US-2004-0171148-A1 which is incorporated herein by reference.

In an embodiment, the progenitor cells or stem cells are cultured in a 6 cm or 10 cm tissue culture-treated dish with a Notch Ligand Cell Preparation. For example, the concentration of hematopoietic progenitor cells or embryonic stem cells in the culture is between 1-10$^{9}$, preferably 1×10$^{2}$ to 1×10$^{6}$, more preferably 1×10$^{3}$ to 1×10$^{4}$. In a particular embodiment, hematopoietic progenitor cells or embryonic stem cells (about 1−5×10$^{4}$ cells) are cultured on a monolayer of OP9 cells expressing Delta-like-1 or Delta-like 4.

One or more positive cytokines that promote commitment and differentiation of pro-T cells may also be added to the culture. The cytokines may be human in origin, or may be derived from other species. The concentration of a cytokine in a culture is typically about 1-10 ng/ml. The following are representative examples of cytokines that may be employed in the present application: all members of the fibroblast growth factor (FGF) family including FGF-4 and FGF-2, Flt-3-ligand, and interleukin-7 (IL-7). Preferably the cytokines used herein are Flt-3-ligand and IL-7. The cytokines may be used in combination with equal molar or greater amounts of a glycosaminoglycan such as heparin sulfate. The cytokines are commercially available or can be produced by recombinant DNA techniques and purified to various degrees. Some of the cytokines may be purified from culture media of cell lines by standard biochemical techniques.

The progenitor cells and stem cells may be cultured in culture medium comprising conditioned medium, non-conditioned medium, or embryonic stem cell medium. Examples of suitable conditioned medium include IMDM, DMEM, or αMEM, conditioned with embryonic fibroblast cells (e.g. human embryonic fibroblast cells or mouse embryonic fibroblast cells), or equivalent medium. Examples of suitable non-conditioned medium include Iscove's Modified Delbecco's Medium (IMDM), DMEM, or αMEM, or equivalent medium. The culture medium may comprise serum (e.g. bovine serum, fetal bovine serum, calf bovine serum, horse serum, human serum, or an artificial serum substitute) or it may be serum free.

The culture conditions entail culturing the progenitor cells or stem cells for a sufficient period of time so that cells in the preparation form pro-T cells. The cells are maintained in culture generally for 4-50 days, preferably 5 to 20 days. It will be appreciated that the cells may be maintained for the appropriate amount of time required to achieve the desired cellular composition.

Accordingly, the present application provides a method of generating a pro-T cell comprising (a) culturing a sample comprising stem cells or progenitor cells with cells that express a Notch ligand and (b) isolating pro-T cells. The cells expressing a Notch ligand are preferably OP9 cells expressing DL1 or DL4. The pro-T cells may be characterized by the phenotype $CD34^{+}CD7^{+}CD1a^{-}$.

The methods of the present application allow the generation of large numbers of pro-T cells. The pro-T cells exhibit, or have the potential to differentiate into cells that exhibit morphological, physiological, functional, and/or immunological features of T cells. The generation of large numbers of pro-T cells with the ability to form mature T cells makes them highly useful in cell therapy.

In another embodiment, the progenitor T-cell is obtained by co-culturing stem cells such as HSC with OP9-DL1 cells or OP9-DL4 cells, fractionating the cells and collecting the cells of a desired phenotype. The fractionation step may involve any suitable cell separation technique known in the art such as (density gradient, ferromagnetic beads cytometry and fluorescence activated call sorting.) Bioreactors (matrices). In particular, the cells cultured on the OP9-DL1 or OP9-DL4 cells may be further fractionated into $CD5^{+}$ (pro-T2) and $CD5^{-}$ (pro-T1) subsets. The pro-T2 subset may be preferably used for T-cell engraftment.

In another embodiment, the progenitor T cells may be used to generate NK cells when cultured under appropriate conditions. Appropriate conditions to generate NK cells include culturing the pro-T cells with cytokines such as IL-15 or IL-2. The pro-T cells can also be cultured stromal cells such as OP-9 cells. Accordingly, the present application provides a method of generating natural killer (NK) cells comprising a) culturing an isolated progenitor cell with IL-15 and b) isolating NK cells. The NK cells may be characterized by the phenotype $CD56^{+}$.

II. Pharmaceutical Compositions

In another aspect, the present application provides a pharmaceutical composition comprising isolated pro T-cells and a pharmaceutically acceptable diluent or carrier.

Suitable diluents and carriers are described, for example, in Remington's Pharmaceutical Sciences. On this basis, the compositions include, albeit not exclusively, solutions of the pro-T cells in association with one or more pharmaceutically acceptable vehicles or diluents, and contained in buffered solutions with a suitable pH and iso-osmotic with the physiological fluids.

Pharmaceutical compositions include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween™), alcohols, polyols, glycerin and vegetable oils, for example. Extemporaneous injection solutions and suspensions may be prepared from sterile powders, granules, tablets, or concentrated solutions or suspensions. The composition may be supplied, for example but not by way of limitation, as a lyophilized powder which is reconstituted with sterile water or saline prior to administration to the patient.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesyl-phosphotidyl-ethanolamine (DOPE), and liposomes. Such compositions should contain a therapeutically effective amount of the compound, together with a suitable amount of carrier so as to provide the form for direct administration to the patient.

The compositions of the application can be administered for example, by parenteral, intravenous, subcutaneous, intramuscular, intracranial, intraorbital, ophthalmic, intraventricular, intracapsular, intraspinal, intracisternal, intraperitoneal, intranasal, aerosol or oral administration. For parenteral administration, solutions of the pro-T cells described herein can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

Preferably the pre T-cells are present in an amount effective for treating a disease state in a mammalian need thereof. In one embodiment the pre T-cell is present in an amount effective to enhance hematopoietic progenitor cell engraftment in a mammal in need thereof. Optionally, the composition further comprises pre T-cells, or tissue for transplantation. In one embodiment the tissue comprises a thymus. In another embodiment the tissue comprises an organ.

III. Applications

The present application includes the use of pro-T cells in any and all applications.

A. Genetic Modification

Pro-T cells generated using the methods of the application may be genetically modified (transduced or transfected) either in nature or by genetic engineering techniques in vivo or in vitro. Cells can be modified by introducing mutations into genes in the cells or by introducing transgenes into the cells. Insertion or deletion mutations may be introduced in a cell using standard techniques. A gene encoding a selectable marker may also be integrated into the cells.

An aspect of the present application relates to pro-T cells that are genetically engineered in such a manner that the cells or cells derived therefrom produce, in vitro or in vivo, polypeptides, hormones and proteins not normally produced in the cells in biologically significant amounts, or produced in small amounts but in situations in which regulatory expression would lead to a therapeutic benefit. For example, the cells could be engineered with a gene that expresses insulin at levels compatible with normal injected doses, or with a gene that can make up for a deficiency or abnormality of a gene causing a disease. Alternatively the cells could be modified such that a protein normally expressed will be expressed at much lower levels. These products would then be secreted into the surrounding media or purified from the cells. The cells formed in this way can serve as continuous short term or long term production systems of the expressed substance.

Thus, in accordance with this aspect of the application, pro-T cells generated using the methods of the application can be modified with genetic material of interest. The modified cells can be cultured in vitro under suitable conditions so that they are able to express the product of the gene expression or secrete the expression product. These modified cells can be administered so that the expressed product will have a beneficial effect.

In a further embodiment, transduced pro-T cells (with the potential to form mature T cells) can be induced in vivo to differentiate into T cells that will express the gene product. For example, the transduced cells may be administered to induce production of T cells having the transduced gene. The cells may be administered in a mixture with other cells or separately and may be delivered to a targeted area. The cells can be introduced intravenously and home to a targeted area. Alternatively, the cells may be used alone and caused to differentiate in vivo.

Thus, genes can be introduced into cells that are then injected into a recipient where the expression of the gene will have a therapeutic effect. For example, an insulin gene may be introduced into the cells to provide a constant therapeutic dose of insulin in the bone marrow and peripheral blood.

The technology may be used to produce additional copies of essential genes to allow augmented expression by T cells of certain gene products in vivo. These genes can be, for example, hormones, matrix proteins, cell membrane proteins, and cytokines.

In a specific embodiment, the pro-T cells are engineered to recognize an antigen such as a tumor antigen, a viral antigen or a bacterial antigen. As such the immune response to the target antigen will be augmented by administering antigen specific progenitor T cells.

B. Therapeutic Applications

The ability to generate in vitro-derived human progenitor T cells and to test their safety in human/mouse immune engraftment models, opens avenues for cellular based approaches for treating immune-related disorders of the T lineage (Legrand et al., 2006; van den Brink et al., 2004). T cells are the major effector arm of the adaptive immune system in recognizing and eliminating viral and bacterial pathogens. In certain rare blood cancers such as T cell acute lymphoblastic leukemia (T-ALL), T cells proliferate crowding out healthy immune cells and perturbing normal immune function (Ferrando et al., 2002; Weng et al., 2004). Although chemotherapy can often impart therapeutic benefits in cancer patients, it often can lead to immuno-deficiency and susceptibility to opportunistic infections. Opportunistic infections also pose a serious concern in AIDS patients whose $CD4^+$ T cells have been depleted following infection with HIV. While immunodeficiency remains a serious concern in HIV/AIDS and cancer, immune-hypereactivity is equally problematic in autoimmune disease where T cells that lack proper regulatory control, make immune responses to self-tissue.

Accordingly, the present application includes a method of treating an animal having a condition requiring an increase in the number of T cells comprising administering an effective amount of a progenitor T cell to an animal in need thereof.

As used herein, the phrase "effective amount" or "therapeutically effective amount" means an amount effective, at dosages and for periods of time necessary to achieve the desired result. Effective amounts may vary according to factors such as the disease state, age, sex, weight of the animal. The amount of a given cell preparation that will correspond to such an amount will vary depending upon various factors. Such as the pharmaceutical formulation, the route of administration, the type of disease or disorder, the identity of the subject or host being treated, and the like, but can nevertheless be routinely determined by one skilled in the art. An "effective amount" will preferably be an amount effective for the progenitor T cells to engraft the subject being treated.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "Treatment" can also mean prolonging survival as compared to expected survival if not receiving treatment. "Treating" and "treatment" as used herein also include prophylactic treatment.

The term "animal" as used herein means any member of the animal kingdom and is preferably a human.

A "condition requiring an increase in number of T cells" includes any condition wherein T cell levels are reduced as compared to a healthy animal, including, without limitation, immunodeficiency, cancer, genetic diseases, infectious diseases and autoimmunity, some of which are described in detail below.

(i) Cancer

In 2005, nearly 128,000 individuals were diagnosed with myeloma, lymphoma and leukemia in North America (US & Canada). Following aggressive myeloablative-chemo/radiotherapy of these blood cancers, these individuals may become immunodeficient and require stem cell transplantation to replace or restore their immune system. Indeed, every year in North America 9,000 individuals undergo stem cell transplantation. Although, HSCs may be obtained from bone marrow, GM-CSF-mobilized peripheral blood, or cord blood, several clinical challenges present themselves in most stem cell transplantations: from finding a suitably major-histocompatible matched donor, to preventing GvHD, to successful engraftment of a donor immune system onto the host (Socie, 2005). Most immune cells recover quickly following transplantation, but T cells take the most time (~2 years) to recover in terms of cell numbers and function (Petropoulos and Chan, 2005). This is perhaps dictated by the broad repertoire of TCRs required to cover the range of environmental and pathogenic antigens that an individual will be exposed to. Until that broad repertoire is re-established, gaps may exist that permit the emergence of opportunistic infections.

Accordingly, the present application provides a method of treating or preventing cancer comprising administering an effective amount of a progenitor T cell to an animal in need thereof.

In one embodiment, the pro-T cells have been genetically engineered to recognize tumor specific antigens. For example, progenitor T cells could be manufactured to recognize tumor-specific antigens found in certain breast cancers as well as Burkitt's lymphoma, neuroblastoma, malignant melanoma, osteosarcoma, and renal cell carcinoma (Renkvist et al., 2001). One example of this genetic approach utilizing $CD8^+$ Wilms' tumor (WT1) gene-specific cytotoxic T-lymphocyte clones for the treatment of Chronic Myeloid Leukemia (CML) or Acute Lymphoblastic Leukemia (ALL). Thus, progenitor T cell transplantation could be used as an adjuvant therapy with stem cell transplantation to quickly reconstitute the T cell compartment in patients with terminal illness or specifically target cancer cells for destruction (van den Brink et al., 2004).

(ii) HIV/AIDS:

Acquired Immunodeficiency Syndrome (AIDS), which follows the infection with the Human Immunodeficiency Virus (HIV), is characterized by a chronic decline in the number of CD4 helper T cells. The CD4 T cell is a critical immune or white-blood cell that helps to maintain the function of "killer" CD8 cytotoxic T cells, which lyse virus-infected cells (Grossman et al., 2006). AIDS has become a global pandemic with an estimated 38 million people living with the disease worldwide and 1.6 million cases in North America alone. Current treatment regimens including the highly active anti-retroviral therapy (HAART), a combination of several anti-HIV drugs [i.e.: Viramune (nevirapine), Rescriptor (delavirdine), Invirase (saquinavir), and Norvir (ritonavir)], have been effective in reducing viral load and extending the life-span of HIV-infected individuals but have proven difficult to implement/achieve/maintain over long-periods of times for a variety or reasons (i.e.: toxicity, financial burden, government apathy, and evolving resistance of HIV to these drugs). Indeed, HAART is often given in cycles with 'vacations'/break periods to allow the patient to recover from anti-viral drug induced toxicity. As a result there is continued interest to find more efficacious drugs and/or cellular based therapies (i.e. vaccines or stem cell approaches) that keep pace with the evolving resistance of HIV and would augment or replace current treatment regimens to restore or maintain T cell numbers.

In the case of HIV/AIDS, the value of the present application may be the ability to create large numbers of in vitro-generated progenitor T cells that would offer therapeutic benefits to individuals that HAART has failed or that have gone off HAART due to drug toxicity. One advantage of a progenitor T cell based therapy would be minimal toxicity and side-effects of these cells compared to anti-retrovirals. Given, that few treatment options are available to this subpopulation of individuals that have failed HAART, the use of progenitor T cells could be a viable option. Although these progenitor T cells and their $CD4^{+}$ progeny would again be subject to HIV infection in vivo and require multiple treatments, the capacity to expand non-infected cells in vitro and restore T cell numbers in vivo may help to restore immune function and limit the emergence of opportunistic infections for some time during periods of planned HAART 'vacation' or failure. This presents two future extensions of this technology for therapeutic potential. First, the OP9-DL1 coculture system may have therapeutic potential as an adjuvant therapy in combination with HAART, or as a stand-alone therapy when HAART is periodically discontinued. As with the case of cancer, the OP9-DL1 coculture system lends itself towards emerging genetic approaches to create designer T cells resistant to HIV infection. One example of such an innovative approach would be the expression of the mutant form of the chemokine co-receptor CCR5 that blocks viral infection (Markovic, 2006; Samson et al., 1996) in progenitor T cells. Such an approach would offer a novel means to treat HIV/AIDS by preventing HIV infection and thus maintaining T cell numbers and T cell function and is no longer far-fetched as several clinical trials have been approved for the treatment of HIV/AIDS using genetically modified mature-$CD4^{+}$ T cells and $CD34^{+}$ HSCs, but not-progenitor T cells.

Accordingly, the present application provides a method of treating or preventing an immunodeficiency comprising administering an effective amount of a progenitor T cell to an animal in need thereof. In one embodiment, the immunodeficiency is HIV/AIDS.

(iii) Autoimmunity

Traditionally, tolerance was thought to be established centrally in the thymus to self-antigen presented by thymic cells and blood-borne self-antigens, while T cells with specificity towards tissue-specific antigens underwent tolerance induction in the periphery (Kyewski and Derbinski, 2004). The recent observation that thymic epithelial cells that express the AIRE gene can promote the promiscuous expression of tissue-restricted antigens has yielded new insights for how self-tolerance is maintained and broken (Kyewski and Derbinski, 2004). Autoimmune diseases result from the dysregulation or breakdown of the processes that maintain self-tolerance in the periphery. Many investigators have demonstrated that a population of T cells with regulatory activity ($T_{Reg}$) can suppress pathological immune responses in murine models of autoimmune disease, transplantation and GvHD (Chatenoud et al., 2001) suggesting that these cells could be utilized therapeutically to treat human autoimmune disease (Bluestone, 2005). $T_{Reg}$ cells express CD4 and CD25 as wells as the forkhead transcription factor boxP3 (Foxp3) (Sakaguchi, 2005), which serves as a master regulator for $T_{Reg}$ development and function (Fontenot et al., 2003; Hori et al., 2003). Indeed, Foxp3-mutant mice have a deficiency in $T_{Reg}$ cells and develop severe lymphoproliferative autoimmune syndrome. Similarly, humans with the rare recessive disorder: Immunodysregulation, Polyendocrinopathy and Enteropathy X-linked (IPEX) syndrome exhibit aggressive autoimmunity and early (Walker et al., 2003).

$T_{Reg}$ cells can be generated both in the thymus and in the periphery and appear phenotypically and functionally similar. Studies with TCR-transgenic systems indicate that relatively high-affinity interactions of αβTCR with self-peptide agonists presented on thymic epithelial cells are required to efficiently generate $T_{Reg}$ cells in a CD28-dependent manner (Apostolou et al., 2002; Jordan et al., 2001; Tai et al., 2005; Walker et al., 2003). As a result, intrathymic $T_{Reg}$ cells utilize a diverse TCR repertoire (Bluestone and Abbas, 2003) skewed toward autoantigen recognition. Recently, it was demonstrated Hassall's corpuscles express thymic stromal lymphopoietin (TSLP), which activates thymic dendritic cells to induce the proliferation of $T_{Reg}$ cells (Watanabe et al., 2005). Alternatively, $T_{Reg}$ cells can be expanded extrathymically through differences in self-peptide exposure and cytokine milieu (i.e.: transforming growth factor-β (TGF-β) and IL-10) (Apostolou and von Boehmer, 2004; Belghith et al., 2003; Roncarolo et al., 2001; Weiner, 2001).

The observation that $T_{Reg}$ cells are deficient in patients with multiple sclerosis, type 1 diabetes, rheumatoid arthritis (Ehrenstein et al., 2004; Lindley et al., 2005; Viglietta et al., 2004) has raised hope that treatment of these and other autoimmune diseases may rest with the restoration of $T_{Reg}$ cells (Bluestone, 2005). In contrast, the elimination of $T_{Reg}$ cells may play a significant role in enhancing cancer immunotherapeutic approaches by releasing the breaks on antitumor T cell responses and inducing limited local autoimmunity (Sakaguchi et al., 2001). Finally, $T_{Reg}$ cells may play a critical role in the establishment of tolerance following allogenic organ transplant thereby minimizing rejection mediated by GvHD (Gregori et al., 2005; Hoffmann and Edinger, 2006; Touraine et al., 2005).

As with most cellular based therapies, the major obstacle for the utilization of $T_{Reg}$ cells in the treatment of autoimmunity is the ability to generate them in large numbers to realize therapeutic effectiveness. Currently, the OP9-DL1 coculture system does not support the generation of large numbers of $T_{Reg}$ cells from progenitor T cells. Given the role of TSLP in the generation of $T_{Reg}$ cells (Watanabe et al., 2005), it is unclear whether the absence of $T_{Reg}$ cells in the OP9-DL1 coculture system is due to a deficiency of OP9 cells to produce TSLP.

Regardless, stem cell transplantation for the treatment of severe autoimmunity is gaining momentum (Bluestone, 2005; Gregori et al., 2005; Sykes and Nikolic, 2005) with the development of human/immunodeficient mouse models of alloreaction (Thomsen et al., 2005), methods to expand regulatory T cell populations (Kretschmer et al., 2005) and to engineer stem cells and progenitor T cells to express self-antigen (Alderuccio et al., 2003).

Accordingly, the present application provides a method of treating or preventing an autoimmune disease comprising administering an effective amount of a progenitor T cell to an animal thereof.

(iv) Genetic Diseases

As mentioned previously, the pro-T cells may be transfected with a desired gene. Such cells can be used for treatment of genetic diseases. Hematopoietic cell-related genetic diseases can be treated by grafting the cellular composition with cells transfected with a gene that can make up for the deficiency or the abnormality of the gene causing the diseases. For example, a normal wild type gene that causes a disease such as β-thalassemia (Mediterranean anemia), sickle cell anemia, ADA deficiency, recombinase deficiency, recombinase regulatory gene deficiency and the like, can be transferred into the pro-T cells by homologous or random recombination and the cells can be grafted into a patient. Further, a cellular composition comprising normal T cells free from abnormalities of genes (from a suitable donor) can be used for treatment.

Another application of gene therapy permits the use of a drug in a high concentration, which is normally considered to be dangerous, by providing drug resistance to normal T cells by transferring a drug resistant gene into the cells. In particular, it is possible to carry out the treatment using an anticancer drug in high concentration by transferring a gene having drug resistance against the anticancer drug, e.g., a multiple drug resistant gene, into pro-T cells in a cellular composition of the application.

Diseases other than those relating to the hematopoietic system can be treated by using the cellular compositions comprising pro-T cells in so far as the diseases relate to a deficiency of secretory proteins such as hormones, enzymes, cytokines, growth factors and the like. A deficient protein can be induced and expressed by transferring a gene encoding a target protein into the pro-T cells under the control of a suitable promoter. The expression of the protein can be controlled to obtain the same activity as that obtained by the natural expression in vivo.

It is also possible to insert a gene encoding a ribozyme, an antisense nucleic acid or the like (e.g., short-interfering RNA) or another suitable gene into pro-T cells to control expression of a specific gene product in the cells or to inhibit susceptibility to diseases. For example, the pro-T cells can be subjected to gene modification to express an antisense nucleic acid, siRNA, or a ribozyme, which can prevent growth of hematic pathogens such as HIV, HTLV-I, HTLV-II and the like in pro-T cells. In an embodiment, pro-T cells of a cellular composition of the application are created which express known inhibitory genes of HIV replication, such as RNA decoys or the Tat- or Rev-responsive elements, or a dominant negative mutant of the Rev trans-activator protein. Pro-T cells derived from hematopoietic progenitor cells or ES carrying these genes would provide a potentially limitless and defined source of HIV-resistant lymphocyte progenitors.

C. Screening

The cellular compositions comprising pro-T cells may be used to screen for potential modulators or therapeutics that modulate development or activity of pro-T cells or cells differentiated therefrom. In particular, the cellular compositions may be subjected to a test substance, and the effect of the test substance may be compared to a control (e.g. in the absence of the substance) to determine if the test substance modulates development or activity of pro-T cells or cells differentiated therefrom.

In an aspect of the application a method is provided for using a cellular composition of the application comprising pro-T cells or cells differentiated therefrom to assay the activity of a test substance comprising the steps of:

(a) generating pro-T cells with a system or method of the application in the presence of a test substance, or culturing pro-T cells compositions generated using a system or method of the application in the presence of a test substance; and (b) detecting the presence or absence of an effect of the test substance on the survival of the cells or on a morphological, functional, or physiological characteristic and/or molecular biological property of said cells, whereby an effect altering cell survival, a morphological, functional, or physiological characteristic and/or a molecular biological property of the cells indicates the activity of the test substance.

In another aspect a method is provided for using pro-T cells or cells differentiated therefrom generated in accordance with the application, to screen a potential new drug to treat a disorder involving T cells comprising the steps of:

(a) generating pro-T cells with a system or method of the application in the presence of a potential new drug, or culturing pro-T cells preparations generated using a system or method of the application in the presence of a potential new drug; and (b) detecting the presence or absence of an effect of the potential new drug on the survival of the cells in vitro or on a morphological, functional or physiological characteristic and/or molecular biological property of said cells, whereby an effect altering cell survival, a morphological, functional, or physiological characteristic and/or a molecular biological property of the cells in vitro indicates the activity of the potential new drug.

The cellular compositions of the application may be used to prepare model systems of disease. The cellular compositions of the application can also be used to produce growth factors, hormones, etc.

The cellular compositions of the application can be used to screen for genes expressed in or essential for differentiation of T cells. Screening methods that can be used include Representational Difference Analysis (RDA) or gene trapping with for example SA-lacZ (D. P. Hill and W. Wurst, Methods in Enzymology, 225: 664, 1993). Gene trapping can be used to induce dominant mutations (e.g. by deleting particular domains of the gene product) that affect differentiation or activity of T cells and allow the identification of genes expressed in or essential for differentiation of these cells.

The following non-limiting examples are illustrative of the present application:

EXAMPLES

Example 1

Preparation of Umbilical Cord Blood Sample

Obtain 25-50 mls of human umbilical cord blood (UCB) by syringe extraction and collect in a single blood pack unit containing citrate phosphate dextrose anti-coagulant (CPDA) (Baxter Healthcare, Deerfield, Ill.). Within 12 hours of collection, cord blood mononuclear cells are isolated using Ficoll density centrifugation and frozen until further use. Specifically, the human cord blood sample is diluted 1:4 in PBS or HBSS+2 mM EDTA. The mononuclear cells are isolated by gradient centrifugation in Ficoll-Paque Plus (Amersham Biosciences, Cat 17-1440-03). Using a thin sterile Pasteur Pipette underlay the diluted cord blood sample with Ficoll-Paque. Centrifuge at 1350-1860 rpm for 30-40 minutes at 18-20° C. Wash lymphocyte layer 3× in PBS or HBSS, centrifuging between each wash at 1200 rpm for 5 minutes, removing supernatants each time. Resuspend cells in 1 ml of sterile FACS sorting buffer and freeze at −80° C. For each experiment, frozen UCB was thawed and then pre-enriched into lineage-negative (Lin−) and lineage-positive ($Lin^+$) fractions with the autoMACS™ or autoMACS-pro separator (Miltenyi Biotec, Auburn, Calif.) using the StemSep® human progenitor cell enrichment cocktail (Stem Cell technologies, Vancouver, BC, Canada). To isolate the human HSCs, $Lin^-$ cells were stained with anti-human CD38-APC mAbs and anti-human CD34-PE mAbs and subsequently sorted for $CD34^+$ $CD38^{-/lo}$ cells utilizing a BD Biosciences FACSAria digital cells sorter (San Jose, Calif.). Sorted human HSCs were greater than 99% pure as determined by post-sort analysis.

Example 2

Human Hematopoietic Stem Cells and OP9-DL1 or OP9-DL4 Cell Coculture

OP9 cells retrovirally-transduced to express either GFP-vector backbone (OP9-control) or bicistronic plasmid containing GFP and Delta-like 1 (OP9-DL1) or Delta-like 4 (OP9-DL4) were generated as previously described (Schmitt and Zúñiga-Pflücker, 2002), and maintained in α-MEM medium supplemented with 20% coculture-characterized fetal bovine srum (FBS) (Hyclone), plus 50 U/ml penicillin and 50 μg/ml streptomycin (OP9-media). In most experiments, $1\text{-}5\times10^4$ sorted human HSCs ($CD34^+$ $CD38^{-/lo}$) were added per individual well of a 6-well plate containing confluent OP9-DL1 or OP9-DL4 cells, and cultured in OP9-media supplemented with recombinant human cytokines Flt-3L (5 ng/ml) and IL-7 (5 ng/ml), (Peprotech, Rocky Hill, N.J.). Every 4-5 days, human HSCs/(OP9-DL1 or OP9-DL4) cocultures were transferred onto a fresh confluent monolayer of OP9-DL1 or OP9-DL4 cells. For high cell density cocultures, media changes were performed every 2 days between passages as previously described (Awong et al., 2008).

The ability to utilize simple stromal cell monolayers that express Delta-like-molecules such as OP9-DL1 cells or S17-DL1 cells has permitted a closer examination of human T cell development than was previously possible. The OP9-DL1 cells have been already distributed to nearly 400 laboratories around the world. Research emerging from these laboratories has confirmed the molecular elements required to sustain the generation of T cells (Lehar and Bevan, 2002; Wang and Spangrude, 2003) from numerous sources of progenitor cells and has helped to elucidate many other factors with critical roles in T cell development (Gutiérrez-Frías et al., 2004; Outram et al., 2000; Pongracz et al., 2003; Shah et al., 2004; Staal et al., 2004; Weerkamp et al., 2006b; Weerkamp et al., 2006d).

While the paradigm that T cell development requires signaling through Delta-like ligands has been firmly established for Delta-like-1 expression, it is beginning to emerge that Delta-like-4 expression can also recapitulate T cell development in vitro (Schmitt and Zúñiga-Pflücker, 2006). This is not surprising given that Delta-like-4 shares sequence homology with Delta-like-1 and is also expressed within the thymus (Schmitt and Zúñiga-Pflücker, 2002).

Prior to the advent of OP9-DL1 or OP9-DL4 cells, the study of human T cell development required cumbersome FTOCs and their derivative systems, which although functional, were cumbersome, inefficient, and impractical given the limitations of hybrid/mouse FTOCs and the lack of available human fetal thymic tissue. Thus, it was difficult to conceive how one could generate the numbers of human progenitor T cell needed to elicit therapeutic effectiveness for the treatment of immune-related disease. The OP9-DL1 and OP9-DL4 technology has numerous advantages. Many of these advantages have been reviewed previously with an emphasis on mouse T cell development (Zúñiga-Pflücker, 2004) and offer similar advantages with regard to the study of human T cell development.

An important practical consideration of the OP9-DL1 and OP9-DL4 coculture systems is its technical simplicity. Human HSCs are cultured directly on a simple monolayer with the addition of two human cytokines Flt-3L and IL-7 for long periods of time. Thus, with media changes and transfer onto new stroma, the OP9-DL1 and OP9-DL4 cells are easily manipulated and readily expanded into larger cultures. This is in contrast to cumbersome FTOCs, which often require direct microinjection of human progenitor cells and have limited culture times. Given these constraints, the OP9-DL1 and OP9-DL4 coculture system represents an improvement over FTOCs in that a single cell can be now assayed for T cell progenitor cell function (Ciofani et al., 2006; Schmitt and Zúñiga-Pflücker, 2002). Although this was possible using FTOCs (Ikawa et al., 1999; Michie and Zúñiga-Pflücker, 2000; Williams et al., 1986), the feasibility of large-scale analyses was nearly prohibitive and there were no reports of progenitor frequency using single cell analysis for human progenitor T cells. Thus, together with the current assays presently used in FTOCs, the inventors' system can complement different approaches utilized in the study of human T cell development, opening new avenues for future research to test the immune reconstitution capabilities and immune function of in vitro-derived T cells (Jenkinson and Anderson, 1994; Takahama, 2000).

Additionally, the OP9-DL1 and OP9-DL4 systems have been able to support generation of T cells from a number of defined sources. Mouse progenitor cells obtained from fetal liver, bone marrow, fetal thymus, and peripheral blood, and embryonic stem cells (ESCs) generate T cells upon OP9-DL1 coculture (Adolfsson et al., 2005; Ciofani and Zúñiga-Pflücker, 2005; Schmitt et al., 2004; Schmitt and Zúñiga-Pflücker, 2002). Similarly, human progenitor cells isolated from fetal liver, bone marrow, fetal thymus, GM-CSF-mobilized peripheral blood, and umbilical cord blood generate T cells upon OP9-DL1 coculture (De Smedt et al., 2004; La Motte-Mohs et al., 2005; Weerkamp et al., 2006a). With regard to ESCs and HSCs, the emerging uses of short interfering RNA (siRNA) (Gimeno et al., 2004; McManus and Sharp, 2002) and locked nucleic acids (Grünweller et al., 2003) as methods of choice to quickly assay for the functional importance of a particular gene, for instance during T cell development, can be easily adapted to the OP9-DL1 and OP9-DL4 cell coculture systems. This allows for a practical approach to characterize the role during T cell development of many genes that when deleted, result in an embryonic lethal phenotype and simply cannot be further studied. Similarly, the OP9-DL1 system is adaptable to genetic engineering. This principle has been demonstrated with retroviral and lentiviral vectors in $CD34^+$ HSC (immature) (Case et al., 1999; Gimeno et al., 2004; Haas et al., 2000; Klug et al., 2000; Su et al., 1997), but not progenitor T cells. As progenitor T cells are cycling and renewed in the OP9-DL1 coculture system, it is likely they will prove equally amenable to genetic manipulation. Thus, together with the current assays presently used with mouse T cell development, there are many different approaches that can now be easily applied to the study of human T cell development.

In contrast to mouse ESCs, undifferentiated human ESCs have not yet generated progenitor cells that can give rise to T cells following coculture with either OP9-DL1 or OP9-DL4 cells. Indeed, the differentiation of human ESCs in OP9-DL1 coculture has proven more challenging. Several groups have demonstrated efficient differentiation of human ESCs into $CD34^+$ cells through embryonic body formation (Cerdan et al., 2004; Chadwick et al., 2003; Wang et al., 2004; Zambidis et al., 2005; Zhan et al., 2004) or coculture on S17 (Tian et al., 2006), MS5 or OP9 (Vodyanik et al., 2005) stromal lines. These $CD34^+$ cells when sorted and re-cultured onto bone marrow stroma give rise to B (Vodyanik et al., 2005) and NK {Woll, 2005 #219(Vodyanik et al., 2005)} cells and dendritic cells (Slukvin et al., 2006) in the presence of the appropriate cytokine, suggesting that human ESCs can differentiate into progenitor cells with multilineage potential. In contrast, sorted human ESC-derived $CD34^+$ cells have thus far not differentiated in vitro into T cells upon coculture with OP9-DL1 cells, nor have embryonic body-derived $CD45^-$, PECAM-$1^+$, Flk-$1^+$, and VE-cadherin$^+$ (PFV) cells upon intra-femoral injection into immunodeficient NOD/SCID mice (Wang et al., 2005b), suggesting that human ESCs may be less sensitive in vitro to Delta-like-Notch induced differentiation signals than mouse ESCs to promote T cell differentiation. Alternatively, the OP9-DL1 cells may not completely substitute for all of the factors required for the induction and early differentiation of human ESCs. This issue has recently been circumvented in vivo through the direct injection of human ESC-derived GFP-labeled $CD34^+$ cells into conjoint human thymic/liver (Thy/Liv) tissues implanted under the kidney capsule into sublethally irradiated immunodeficient SCID-mice (Fleming and Scadden, 2006; Galic et al., 2006).

The ability to derive T cells from human ESCs remains an attractive goal for the treatment of immune-related disorders. This is due to the general consensus that theoretically, unlimited numbers of human T cells may be generated from undifferentiated human ESC cell lines, whereas human HSCs may possess only limited differentiation and proliferation potential from exhaustible sources such as bone marrow and cord blood. Foresight not withstanding, only a small number of human HSCs can be isolated from limited tissue and therefore must be properly stored and expanded for future use. Efforts to expand human HSCs numbers while preventing their differentiation are under development and could be utilized in concert to generate even greater numbers of progenitor T cells. Taken into consideration that not all HSCs exhibit long-term reconstitution potential, and the thymus does not contain progenitor cells that self-renew, the utilization of HSCs and progenitor T cells may have limited niches for the treatment of T cell based immunodeficiency or autoimmunity. Human ESCs are not without their drawbacks and serious concerns remain about their safety given their genomic instability, epigenetic status, their propensity spontaneous differentiation and their potential to cause cancer (Odorico et al., 2001; Olsen et al., 2006; Rugg-Gunn et al., 2005; Wang et al., 2005a).

In the OP9-DL1 or OP9-DL4 coculture systems, human HSCs derived from cord blood and bone marrow show robust expansion. Indeed, the OP9-DL1 or the OP9-DL4 system generates a population of T lineage cells that are highly homogenous and easily isolated based on human markers of T cell differentiation. This system generates T lineage cells efficiently (>90%) at the expense of other lymphocytes and myeloid cells; however, the upper-limit of this T cell expansion is unknown. The output of progenitor-T cells in this coculture system is at least $10^3$-$10^5$ times higher than other in vitro systems suggesting that further scaling-up of this system could yield clinically relevant numbers to achieve therapeutic benefits in patients with immune related disorders. Long term OP9-DL1 cocultures initiated with human $CD34^+$ $CD38^-$ cells demonstrate sustained T cell development for at least 120 days and retain a population of cells, which are $CD34^+$ $CD7^+$. Whether these cells are capable of self-renewal is unclear, although multiple waves of T cell development have been observed in long-term OP9-DL1 or OP9-DL4 cocultures [La Motte-Mohs, unpublished observations]. These waves of T cell development could simply reflect apoptosis of $CD4^+CD8^+$ DP T cell populations that did not receive positive and negative selection signals followed by the re-emergence of progenitor T cells derived from early progenitors maintained in the cultures. Indeed, such a possibility is consistent with the dual role of Notch signaling in maintaining progenitor cell renewal and promoting T cell differentiation (Varnum-Finney et al., 1998). Further studies are required to determine whether the OP9-DL1 or OP9-DL1 coculture systems promote both T cell differentiation and self-renewal at the same time Although the differentiation from stem cell to functional T cell can be obtained readily by coculture on OP9-DL1 cells (Schmitt et al., 2004; Schmitt and Zúñiga-Pflücker, 2002), there are still some drawbacks to this system. For instance, OP9 cells express mouse MHC class I molecules and support the differentiation of mouse HSCs into $CD8^+$ T cells, but do not express mouse MHC class II molecules and do not appear to express CD1d; thus, limiting their ability to support the differentiation of CD4 T cells and NKT cells, respectively (Schmitt and Zúñiga-Pflücker, 2002; Zúñiga-Pflücker, 2004). While there is evidence that mouse MHC molecules can support the differentiation of human HSCs (Fisher et al., 1990; Traggiai et al., 2004), this could be especially problematic when developing cellular immune-therapies to treat immune-related disorders without invoking an autoimmune response or graft-verses host disease (GvHD). However, OP9-DL1 cells could be modified to ectopically express human MHC molecules, which would permit a re-examination of the contributions of these molecules to the development of specific subsets of T cells as well as generate MHC-matched T cells to an individual. Specifically, the inventors have reported the robust and sustained generation of human T cells to the DP stage from cord blood-derived HSCs; however, the generation of $CD4^+$ or $CD8^+$ SP T cells has been limited (La Motte-Mohs et al., 2005), which is likely due to the absence of human HLA molecules on mouse OP9-DL1 cells. Strikingly, under long-term densely packed coculture conditions the inventors can detect $CD4^+$ or $CD8^+$ T cells that express TCRαβ [unpublished observations, Ross La Motte-Mohs]. At first glance, the emergence of human single positive T cells seems difficult to reconcile given the published reports that isolation of human progenitor T cells require human thymic stromal elements to realize their full differentiation potential towards SP T cells. Nevertheless, a recent paper by Choi et al demonstrated that thymocyte-thymocyte (T-T) interactions can mediate positive selection and promote the maturation of CD4 T cells in the absence of MHC-class $II^+$ thymic stroma (Choi et al., 2005). Similarly, the emergence of human $CD4^+$ SP T cells during high-density coculture conditions with OP9-DL1 cells may take advantage of T-T interactions as developing progenitor T cells ($CD34^+CD7^+$) express high levels of human MHC class II molecules [unpublished observations, Ross La Motte-Mohs. Alternatively, γδ-T cells, which emerge later in OP9-DL1 coculture may function as professional APCs towards emerging αβ-T cells permitting further differentiation (Brandes et al., 2005; Modlin and Sieling, 2005).

Interestingly, another drawback is the limited number of self-antigens that OP9-DL1 cells are likely to present to developing T cells. Initially, OP9 cells, in contrast to thymic medullary epithelial cells, were thought unlikely to express the AIRE gene (Anderson et al., 2002) and mediate ectopic self-antigen presentation for peripheral tolerance. However the detection of low levels AIRE message in OP9-DL1 cells [personal communication, Lynn Rumfelt] suggests that OP9-DL1 cells may posses some capacity to present tissue-specific-antigens, such as insulin, which was also detected in OP9 cells. Whether the AIRE transcription factor is functional in OP9-DL1 cells remains to be confirmed experimentally. However, the recent demonstration that skin cells that express AIRE and Delta-like-1 can support thymic-independent T cell development and mediate negative selection (Clark et al., 2005), suggests a similar possibility for the OP9-DL1 cells. Thus, questions dealing with the mechanisms responsible for positive and/or negative selection of the TCR repertoire can be investigated by appropriately manipulating the OP9-DL1 cells and are currently under investigation in the inventors' laboratory. Nonetheless, issues related to the ability or function of OP9-DL1 cells to properly select mature T cells can be avoided by simply transferring $CD4^-$ $CD8^-$ double negative progenitors or immature $CD4^+$ $CD8^+$ T cells, obtained from stem cells cultured on OP9-DL1 cells, into FTOC or intrathymically into host mice (Schmitt et al., 2004). Such an approach not only provides a practical solution to the self-MHC restriction and tolerance issues, but also opens new avenues for future possibilities to test the immune function of the in vitro-derived T cells as well as their efficacy in adapting T cells to treat human immune-related disorders.

These studies underline valid concerns to determine the efficacy and therapeutic effectiveness for the utilization of in vitro-derived progenitor T cells for the treatment of immune-related disorders. Progenitor T cells, whether autologous, or allogeneic, generated in the OP9-DL1 system are immature and still need to undergo positive and negative selection in the host thymus. This suggests that they are unlikely to evoke an auto-immune response or GvHD in vivo. Although GvHD remains a concern in stem cell transplantation, the reconstitution of a human immune system using $CD34^+$HSC, but not progenitor T cells, in both patients and immunodeficient mice have demonstrated the principle of this approach (Barker and Wagner, 2003; de Wynter et al., 1999; Gimeno et al., 2004; Traggiai et al., 2004). Indeed, the utilization of human/mouse models of engraftment (Legrand et al., 2006) may prove particularly useful in helping to evaluate the safety of in vitro derived human progenitor T cells for the treatment of immune-related disorders.

Example 3

Human-Mouse Fetal Thymic Organ Coculture (FTOC)

FTOC (Fisher et al., 1990; Plum et al., 2000) was performed by isolating fetal thymuses from embryos of time-pregnant CD1 mice at day 15 of gestation (Jackson Laboratories, Bar Harbor Me.). The thymuses were cultured for 5 days in the presence of 1.35 mM deoxyguanosine (dGuo) to remove endogenous thymocytes. Human pro-T subsets derived from HSC/OP9DL1 cocultures supplemented with Flt-3L (5 ng/ml), IL-7 (5 ng/ml) and SCF (30 ng/ml) (Peprotech, Rocky Hill, N.J.) were sorted and placed into hanging drops in Terasaki wells for 24 hours followed by transfer to Nucleopore filters on Gelfoam rafts for 7-21 days as indicated. OP9-media and cytokines (Flt-3L and IL-7) were replenished every 5 days. Cells were analyzed by crushing the thymic lobes with a nylon mesh cell strainer to obtain single-cell suspensions.

Traditionally, the development of in vitro models to study human T lymphopoiesis and progenitor cell commitment have relied on the use of host thymic tissue obtained from fetal mice, or from electively terminated human fetuses, and from thymus tissue discarded during pediatric cardiac surgeries. Until recently, the only in vitro model system that permitted the generation of human T cells was the hybrid FTOC system first adapted by Fisher et al (Fisher et al., 1990). In this whole organ based approach, embryonic day 14/15 mouse thymic lobes are depleted of endogenous thymocytes through treatment with 2-deoxyguanosine, seeded with hematopoietic progenitor cells via the hanging drop method and cultured for a period of time on GelFoam-rafts. T cell developmental stages can then be assessed at various time points following introduction of murine hematopoietic progenitors into the thymic rudiments. Using this hybrid human/mouse FTOC, Fisher et al demonstrated the proliferation and generation of mature SP T cells from human fetal thymic progenitor cells (Fisher et al., 1990). This approach was also demonstrated later with postnatal human progenitor thymocytes (Merkenschlager and Fisher, 1991) and human progenitor cells obtained from bone marrow and cord blood (Yeoman et al., 1993). The study by Fisher et al noted that efficient colonization of murine thymic rudiments by human thymic progenitor cells depended on the addition of human thymic stromal elements (Fisher et al., 1990). In order to improve thymic colonization and T cell development, several groups directly injected human progenitor cells into human fetal thymic fragments (Galy et al., 1993; Peault et al., 1991). Despite its inefficiency and technical complexity, hybrid human/mouse FTOCs are routinely used to examine human hematopoiesis and T cell differentiation (Barcena et al., 1995; De Smedt et al., 2002; Galy et al., 1993; Plum et al., 1994; Res et al., 1997).

Example 4

Quantitative Real-Time Reverse-Transcriptase Polymerase Chain Reaction (Q-PCR)

Total RNA was isolated in Trizol reagent and reverse transcribed using Superscript III and Oligo$(dT)_{12-18}$ primers (Invitrogen, Burlington, ON). Diluted cDNA samples from total OP9-control cocultures, total OP9-DL1 cocultures, sorted T-lineage subsets from OP9-DL1 cocultures as indicated in the figures, UCB purified $Lin^+$ $CD3^+$ and $CD33^+$ cells, or bulk and $Lin^-$ human post-natal thymocytes (PNT) were used as templates for Q-PCR reactions. Detection of the Q-PCR was performed with the SYBR Green PCR master mix according to manufacturer's instructions (Qiagen, Mississauga, Ontario or Bio-Rad, Hercules Calif.) on the Applied Biosystems Sequence Detection System 7000. All transcript levels were normalized to human β-actin. Gene-specific forward (F) and reverse (R) primers are as follows: Rag-1, (F) CAACCAAATTGCAGACATCTCAAC (SEQ ID NO:1) and (R) CCATGCTGGCTGAGGTACCT (SEQ ID NO:2); Deltex-1 (F) GTGAGCAAGAGCGACGTGAAG (SEQ ID NO:3) and (R) ACCACATCCTCGGGATTCTTACT (SEQ ID NO:4); Notch-1 (F) CGGGTCCACCAGTTTGAATG (SEQ ID NO:5) and (R) GTTGTATTGGTTCGGCACCAT (SEQ ID NO:6); Gata-3 (F) GATGGCACGGGACACTACCT (SEQ ID NO:7) and (R) GCTCTCCTGGCTGCAGACA (SEQ ID NO:8); Cebpα (F) CGGACTTGGTGCGTCTAAG (SEQ ID NO:9) and (R) GAGGCAGGAAACCTCCAAAT (SEQ ID NO:10); Ccr9, (F) TGTCCCAGGGAGAGTTGCA (SEQ ID NO:11) and (R) GGGTGTCATGGTGGGTCAGT (SEQ ID NO:12); Selplg (F) GTGCCATGCCTCTGCAACT (SEQ ID NO:13) and (R) TGTCCCACAGCTGCAAGCT (SEQ ID NO:14); Itga2 (F) TCTGAGACTGCCAAGGTCTTCA (SEQ ID NO:15) and (R) CAGCTGGTATTTGTCGGA-CATC (SEQ ID NO:16); Itga4 (F) AAGCTGACTGT-TCATGGGTTTGT (SEQ ID NO:17) and (R) TCTCCAC-CATGCACGTTTCA (SEQ ID NO:18); Itga5 (F) CAGTGCCGAGTTCACCAAGA (SEQ ID NO:19) and (R) GCCTTGCCAGAAATAGCTTCCT (SEQ ID NO:20); Itgb1 (F) TCAGAATTGGATTTGGCTCATTT (SEQ ID NO:21) and (R) CCTGAGCTTAGCTGGTGTTGTG (SEQ ID NO:22); and β-actin (F) TTGCCGACAGGATGCAGAA (SEQ ID NO:23) and (R) GCCGATCCACACGGAGTACT (SEQ ID NO:24).

Example 5

Flow Cytometry

Fluorescein isothiocyanate (FITC)-, R-Phycoerythrin (PE)-, allophycocyanin (APC)-, PE-Cy7-, Peridinin chlorophyll protein (PerCP) PerCP-Cy5.5-, Alexa $Fluor_{700}$-, Alexa $Fluor_{750}$-, and Pacific Blue-conjugated antibodies were purchased commercially. They include the following antibodies: FITC: anti-CD34 (clone 581), anti-CD27 (clone M-T271), anti-CD3 (clone HIT3a), anti-TCRαβ (clone T10B9.1A-31); PE: anti-CD7 (M-T701), anti-CD4 (clone RPA-T4), anti-CD49d (clone 9F10) anti-granzyme B (clone eBioGrB); APC: anti-CD1a (clone HI149), anti-CD7 (CD7-6B7), anti-CD8 (clone RPA-T8); PE-Cy7: anti-CD8 (clone RPA-T8); PerCP-Cy5.5: anti-CD5 (clone L17F12); Alexa $Fluor_{700}$: anti-CD4 (clone RPA-T4); APC-Cy7/APC-Alexa $Fluor_{750}$: anti-CD4 (clone RPA-T4); Pacific Blue: anti-CD3 (clone UCHT1). Intracellular staining for granzyme B was performed using the Cytofix/Cytoperm kit according to manufacturer's instructions (BD Biosciences, San Diego, Calif.). All antibodies were obtained from BD Pharmigen with the exceptions of anti-CD49d-PE, anti-granzyme B-PE, anti-CD3-FITC and anti-CD4-APC-Alexa $Fluor_{750}$, which were purchased from eBioscience (San Diego, Calif.). For flow cytometric analyses, cell suspensions obtained from OP9-DL1 cocultures, or fetal thymic organ cultures (FTOCs) were FcRII blocked and stained. Cells were run on a FACSCalibur (BD-Biosciences) or a four-laser LSR II benchtop flow cytometer. Data analysis was performed using FlowJo software (Tree Star, Ashland, Oreg.) by gating on live lymphocytes and lack of propidium iodide uptake. GFP-expressing OP9 stromal cells were excluded through GFP expression and side scatter gating. This procedure eliminated 99% of contaminating GFP-expressing OP9 stromal cells. Numbers in quadrant corners represent percent of gated cells.

Example 6

T Cell Stimulation Assays

In vitro-generated CD3/TCR-$\alpha\beta^+$ $CD8^+$ single positive (SP) cells were sorted from HSC/OP9-DL1 cocultures at days 60-70. For T cell stimulation assays, $4\times10^4$ cells were seeded in individual wells of a flat bottom 96-well plate coated with or without anti-CD3 (2 or 10 μg/ml) and soluble anti-CD28 (1 μg/ml) mAbs. All wells contained OP9-media supplemented with recombinant human IL-2 (1 ng/ml) and recombinant human IL-7 (1 ng/ml) cytokines and were analyzed after 5 days. For T cell proliferation assays, $4\times10^4$ in vitro-generated $CD8^+$ T cells were sorted and loaded with 10 μM carboxyfluorescein succinimidyl ester (CFSE) according to manufacturer's protocol (Molecular Probes, Eugene, Oreg.) prior to plating. Loss of CFSE labeling was assayed after 5 days of stimulation using a FACSCalibur flow cytometer.

Example 7

Precursor Frequency Analysis

Human HSC limiting dilution assay (LDA) was performed by serial dilutions from different cell subsets of UCB samples. UCB cells were sorted as $CD34^+$ $CD38^-$, $CD34^+$ $CD38^{lo}$, $CD34^+$ $CD38^{+/hi}$ using the FACSDiVa cell sorter, and 1 (n=36), 3 (n=24), 10 (n=90), 30 (n=56), 100 (n=58) or 300 (n=13) cells of each subset were directly deposited into individual wells of a 96 well/plate containing OP9-DL1 cell monolayers. Cells were cultured for 11 days, after which they were harvested from individual wells and analyzed by flow cytometry. The presence of $CD45^+$ $CD7^{++}$ cells was scored, and the progenitor frequency determined by the method of maximum likelihood applied to the Poisson model (Fazekas de St, 1982). For human in vitro-derived progenitor-T cells limiting dilution assays were performed using sorted $CD34^+$ $CD7^{++}$ $CD5^-$ and $CD34^+$ $CD7^{++}$ $CD5^+$ subsets obtained from a day 13 HSC/OP9-DL1 coculture, and seeded into a dGuo-FTOC-derived thymus lobe at 500 (n=2), 1000 (n=18), 1500 (n=12), 2000 (n=13), 3000 (n=13), 9000 (n=4) or 22000 (n=1) cells per lobe for $CD34^+$ $CD7^{++}$ $CD5^-$ progenitors or 100 (n=4), 300 (n=9), 500 (n=10), 1000 (n=10), 3000 (n=10), 9000 (n=4) or 22000 (n=1) cells per lobe for $CD34^+$ $CD7^{++}$ $CD5^+$ progenitors. Progenitors were also seeded back onto OP9-DL1 cells in 96 well/plates, and deposited at 1 (n=36), 3 (n=20), 10 (n=20), 30 (n=14), and 100 (n=6) cells per well. Cells were analyzed after 7 days of differentiation, and scored for the presence of $CD45^+$ $CD7^{++}$ (FTOC) or $CD7^{++}$ $CD1a^{-/+}$ cells (OP9-DL1) cells. The progenitor frequency was determined by the method of maximum likelihood applied to the Poisson model (Fazekas de St, 1982).

Example 8

Thymic Reconstitution of Immunodeficient Mice by Human Progenitor Cells Generated In Vitro Materials & Methods Umbilical cord blood samples: Human UCB samples were obtained by syringe extraction and collected in a blood-pack unit containing citrate phosphate dextrose anti-coagulant (Baxter Healthcare, Deerfield, Ill.) from consenting mothers following delivery at Women's College Hospital in accordance to approved guidelines established by the Research Ethics Board of Sunnybrook Health Sciences Centre. Within 12 hours of collection, UCB mononuclear cells were isolated by Ficoll density centrifugation. For each experiment, frozen UCB was thawed and pre-enriched into lineage-negative (Lin−) and lineage-positive ($Lin^+$) fractions with the autoMACS™ (Miltenyi Biotec, Auburn, Calif.) using the StemSep® enrichment cocktail (Stem Cell technologies, Vancouver, BC, Canada). To isolate human HSCs, $Lin^-$ cells were stained with anti-human CD38-APC and anti-human CD34-PE mAbs and subsequently sorted for $CD34^+CD38^{-/lo}$ cells using a BD Biosciences FACSAria sorter (San Jose, Calif.). Sorted human HSCs were greater than 99% pure as determined by post-sort analysis.

NOD/SCIDγc$^{-/-}$ and RAG2$^{-/-}$γc$^{-/-}$Reconstitution Studies:

5-6×$10^5$ sorted HSCs (CD34$^+$ CD38$^{-/lo}$) were added at 3×$10^4$ cells per individual well of a 6-well plate containing confluent OP9-DL1 cells, and the cultures were maintained for 10-12 days in the presence of OP9 media plus rhIL-7 (5 ng/mL); rhFlt-3L (5 ng/mL) and rhSCF (30 ng/mL) after which CD34$^+$CD7$^+$ progenitor T cells (ProT) were sorted. Sorted human pro-T cells were resuspended in recombinant human IL-7/M25 mixture (provided by Dr. C. Surh) and 3.5-5×$10^5$ cells injected (30 μl/mouse) intrahepatically into 4-5 day old neonates. As controls, mice were injected with either PBS or CD34$^+$ stem cells (1.5-2.5×$10^5$). Mice were boosted with IL-7/M25 mixture every 3-4 days. Thymus, spleen and bone marrow were harvested 21-27 days after intrahepatic transplant and single cell suspensions counted then stained for flow cytometry. For coinjection experiments, human UCB CD34$^+$CD38$^{-/lo}$ (HLA-A2$^-$) cells were differentiated on OP9-DL1 cells for 10-12 days, and CD34$^+$CD7$^{++}$ CD5$^+$ (proT2) cells were sorted by flow cytometry. On the same day that proT2 cells are sorted, CD34$^+$CD38$^{-/lo}$ (HLA-A2$^+$) cells from umbilical cord-blood were also sorted. Irradiated (130 cGy) neonatal NOD/SCID/γc$^{null}$ mice from the same litter were injected intrahepatically with 3.5×$10^4$ HSCs alone; 2.5×$10^5$ proT2 cells alone, and 3.5×$10^4$ HSCs together with 2.5×$10^5$ proT2 cells.

Flow Cytometry: Fluorescein isothiocyanate (FITC)-, R-Phycoerythrin (PE)-, allophycocyanin (APC)-, PE-Cy7-, Peridinin chlorophyll protein (PerCP) PerCP-Cy5.5-, Alexa Fluor$_{700}$-, and Alexa Fluor$_{750}$-, conjugated antibodies were purchased commercially (BD Biosciences or eBioscience). Cell suspensions were FcRII-blocked and stained, and analyzed with an LSR-II cytometer. Data analysis was performed using FlowJo software (Tree Star, Ashland, Oreg.) by gating on live lymphocytes, lack of 4',6-diamidino-2-phenylindole (DAPI) uptake followed by CD45 gating for human-specific hematopoietic cells. Numbers in quadrant corners represent percent of gated cells.

Immune Engraftment:

The study of human hematopoiesis employing mouse models first arose in the late 1980's following the discovery of the scid (sever combined immune deficiency) mutation in the C.B-17 mouse strain (Bosma et al., 1983). Such mice harbor a mutation in the prkdc (protein kinase DNA catalytic protein) gene involved in non-homologous end joining during TCR and immunoglobulin rearrangement (Bosma et al., 1983), thus, lacking both mature T and B cells. Soon after, C.B-17 SCID mice were used by McCune et al (McCune et al., 1988) as an experimental system for studying human T cell development in relation to HIV-1. Using this model, (SCID/hu (thy/liv) model) fragments of human fetal thymus and fetal liver are placed under the kidney capsule of the animal and the graft is allowed to vascularize. Fetal liver provides a rich source of human HSCs and the fetal thymus provides the environment where the HSCs can differentiate into T cells. Although it was a groundbreaking model for studying human lymphocyte development in vivo, most of the engrafted cells were restricted to the fetal explants without seeding the mouse bone marrow or other tissues.

Models were then employed to better reflect the ability of human hematopoietic cells to home and differentiate within the mouse environment without human fetal tissues. Many groups were able to demonstrate that sublethally irradiated C.B-17 SCID mice support the engraftment and differentiation of CD34$^+$ progenitor cells from human bone marrow and human cord blood (Lapidot et al., 1992; Vormoor et al., 1994) into multiple hemopoietic lineages. In light of this, CD34$^+$ stem cells were coined 'SCID repopulating cells' (SRC) as they were capable of repopulating hematopoietic lineages in a SCID mouse. Unfortunately, the levels of engraftment were quite low and T cell development in particular was typically absent. A major barrier to this engraftment was innate immune function still present in the SCID mice. In particular, NK cell function was a critical factor determining host resistance to xeno-engraftment. Use of the non-obese diabetic mouse (NOD) aided tremendously in facilitating human cell engraftment. The inbred NOD mouse strain lacks many aspects of innate immune function due to: (1) complement deficiency due to a mutation in the C5 gene (Baxter and Cooke, 1993) (2), compromised NK function and (3) defects in macrophage function due to reduced IL-1 secretion. Indeed, introduction of the SCID mutation onto the NOD background (NOD/SCID) has allowed for successful human engraftment by many groups and is widely used for the study of human hematopoiesis and HSCs (De Smedt et al., 2002; Larochelle et al., 1996). Importantly, Kerre et al demonstrated robust T cell development, albeit in a low percentage of mice, using NOD/SCID animals treated with an antibody blocking murine IL-2Rβ, thus further lowering NK function (Kerre et al., 2002).

Recently, two new mouse models to examine human hematolymphoid development have emerged: RAG2$^{-/-}$$\gamma_c^{-/-}$ and NOD/SCID/$\gamma_c^{-/-}$ immunodeficient mouse strains. Recombinase activation gene 2 (RAG2) deficient mice lack RAG function leading to complete abrogation of T and B cell development, due to an absence of TCR and Ig receptor rearrangement. Furthermore, absence of the common cytokine receptor γ chain ($\gamma_c$), a critical subunit for the IL-2, IL-4, IL-7, IL-9, IL-15 and IL-21 cytokine receptors, renders these cytokines nonfunctional on their target cells. Most importantly, NK cells do not develop in both RAG2$^{-/-}$$\gamma_c^{-/-}$ and NOD/SCID/$\gamma_c^{-/-}$ mouse strains as IL-15R$\gamma_c$ is critical for their development (Goldman et al., 1998), thus improving human immune engraftment (Kerre et al., 2002; Legrand et al., 2006; McKenzie et al., 2005). Recently, Traggiai and colleagues (Traggiai et al., 2004) demonstrated that newborn RAG2$^{-/-}$$\gamma_c^{-/-}$ transplanted with human CD34$^+$ CB cells, developed all major immune cell subsets. Strikingly, T-lymphopoiesis was supported at high levels, in contrast to the inefficiency of earlier models. The study by Traggiai et al also demonstrated that human T cells can populate the peripheral organs and elicit anti-viral immune responses indicating that engrafted human HSCs differentiate and undergo positive selection events (Traggiai et al., 2004). Accordingly, it has been suggested that human T cells undergoing positive selection in the thymus of an immunodeficient mouse would therefore be biased towards mouse MHC molecules and may require transplantation of human thymic fragments to observe selection on human MHC class molecules (Legrand et al., 2006). Alternatively, the type of APC used to present viral antigens or the targeted tissue used by infections agents could determine whether human T cells are positively selected on mouse or human MHC molecules. The study by Traggiai et al seems to support the former possibility given that Epstein-Barr Virus (EBV) infects human B cells which can present viral epitopes in the context of human MHC molecules (Traggiai et al., 2004). Clearly, in vivo models with a superior capacity to accept human immune grafts are available, rendering them as powerful tools to gain insight into human hematolymphoid development and to test the safety of in vitro derived progenitor T cells in the treatment of immune disorders of the T cell lineage.

Results

Cellular Analysis of the Sequential Induction of T-Cell Development in Vitro.

An important step in the establishment of an effective in vitro system for human T-lymphopoiesis is to fully characterize the early stages of T-cell development. To this end, the inventors performed a temporal kinetic analysis of early developmental changes that occur when UCB-derived HSCs are induced to differentiate on OP9-DL1 cells. As expected, flow cytometric analysis of the starting stem cell population showed that sorted $CD34^{+}CD38^{-/lo}$ cells do not express markers of early T-cell differentiation, such as CD7, CD5, CD1a, and CD10; nor markers of late T-cell differentiation such as CD2, CD4, CD8, and CD3 (FIG. 1A).

The inventors made use of CD7 surface expression as a common marker for the temporal analysis of T-cell differentiation (Bárcena et al., 1995; Blom and Spits, 2006). Analysis of CD7 expression in early HSC/OP9-DL1 cocultures revealed that this approach recapitulates early and late stages of T-cell development, in which CD7 expression is first detected at day 4 on $CD34^{+}$ cells, followed by high level expression on $CD34^{+}$ cells by days 6-8, and then slightly decreasing on a subset of $CD34^{-}$ cells at later time points (beyond day 14) (FIG. 1B).

Figure 7:
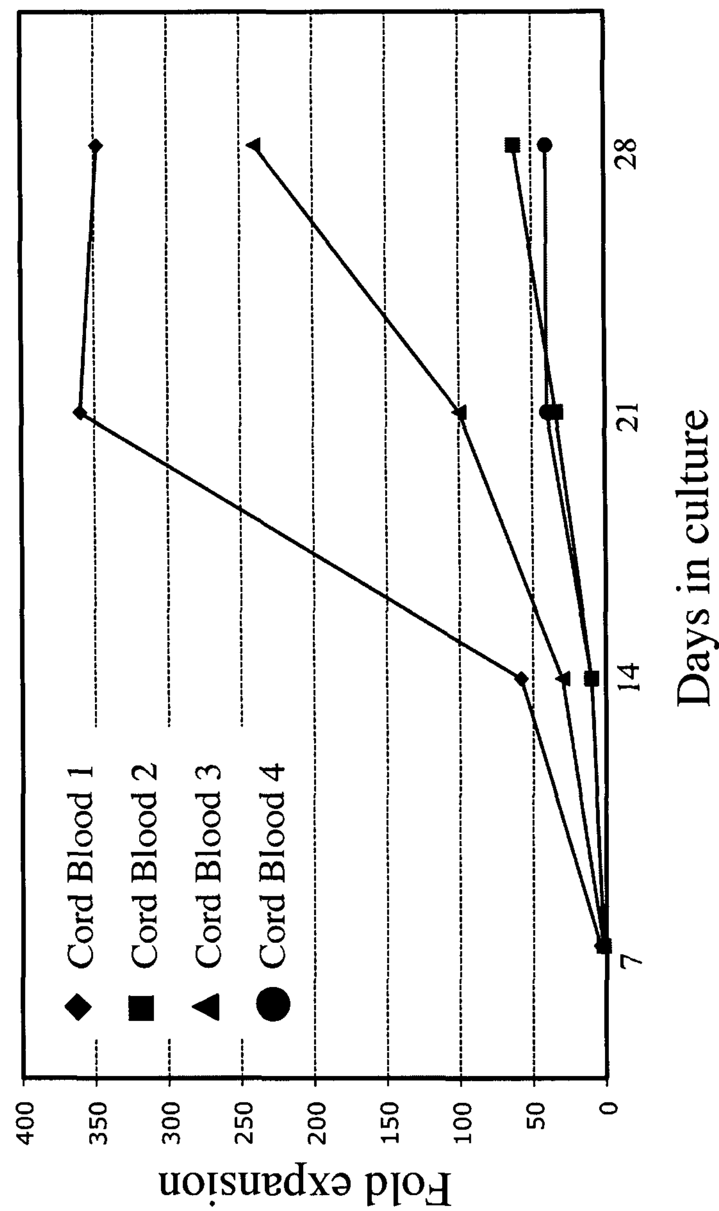
FIG. 7. Analysis of total cellularity from HSC/OP9-DL1 cocultures at different time-points. Human $CD34^+$ $CD38^{-/lo}$ HSCs ($1\times10^4$) from four separate cord bloods were placed into a well of a 6-well plate containing OP9-DL1 cells. Cellularity was determined at the indicated time-points by counting cells under the microscope with a hemocytometer based on trypan blue exclusion, and fold expansion determined by the cellularity obtained at the indicated day divided by the initial input of HSCs.

During the initial week of coculture, as $CD34^{+}$ cells rapidly acquire CD7 expression, the overall cell numbers remain constant (FIG. 7) and the cells remain negative for the expression of CD5, CD1a, CD2 and CD4. By day 8 of culture, CD5 expression is first detected on $CD34^{+}CD7^{++}$ cells, which remain $CD1a^{-}$ (FIG. 16). $CD1a^{+}$ cells begin to be detected by day 10, and present on about 15% of the $CD7^{++}$ cells, which correspond to cells that have also started to down-regulate CD34 expression. By day 14, expression of CD5 is observed on nearly all of the $CD7^{++}$ cells, with CD1a being expressed on the majority of these cells. Day 14 also corresponds to when cells show a blasting phenotype (data not shown) and when cellular expansion begins to become apparent (FIG. 7).

Figure 1:
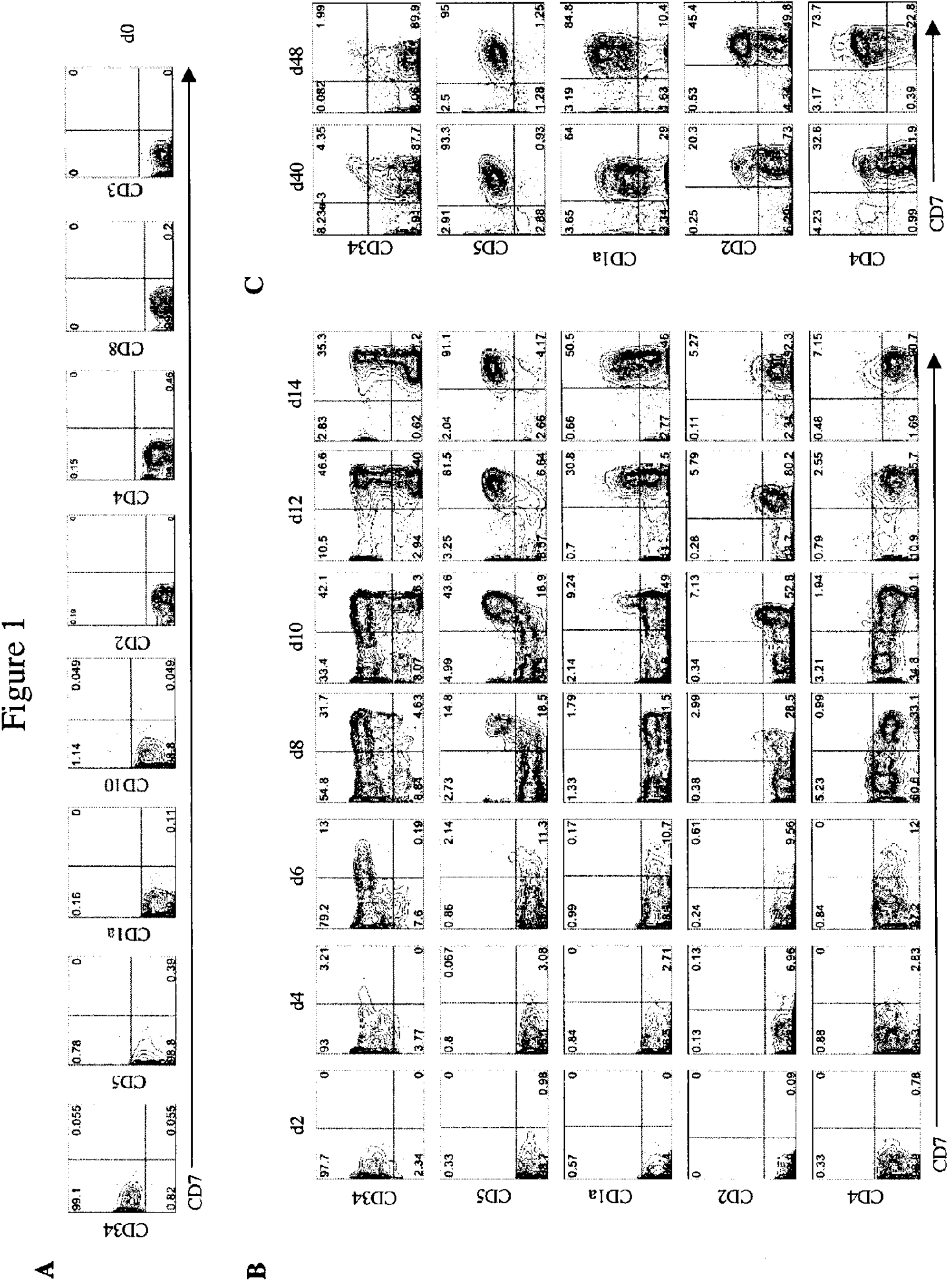
FIG. 1. Developmental progression of human T-lineage cells from $CD34^+$ $CD38^{-/lo}$ HSCs cultured on OP9-DL1 cells. (A) Flow cytometric analysis for the cell surface expression of CD34, CD5, CD1a, CD10, CD2, CD4, CD8, CD3 and CD7 from purified human $CD34^+CD38^{-/lo}$ HSCs prior to coculture with OP9-DL1 cells. (B, C) HSC/OP9-DL1 cocultures were harvested and analyzed by flow cytometry at the indicated time-points for the expression of the markers as shown. Data are representative of at least 5 independent cocultures. Numbers in plots indicate percentage of cells within each quadrant.

At later time points, $CD7^{++}$ and $CD7^{+}$ populations expressing CD2 and CD4 begin to predominate (FIG. 1C). In addition, a population of $CD7^{+}CD1a^{++}$ cells continues to expand, and eventually accounted for nearly 90% of the CD7-expressing cells by day 48. In contrast to early time points (days 8-10), in which CD2 expression is low on $CD7^{++}$ cells, by day 48 nearly 50% of the cells express high levels of CD2 (FIG. 1C). The expression of CD4 on $CD7^{++}$ cells emerges as early as day 12 (FIG. 1B) and continues to increase, eventually accounting for ~75% of the CD7-expressing cells by day 48 (FIG. 1C). Although a small percentage of $CD4^{+}$ cells that lack CD7-expression were detected, the inventors have previously reported that these cells belong to the myeloid lineage (La Motte-Mohs et al., 2005).

Figure 2:
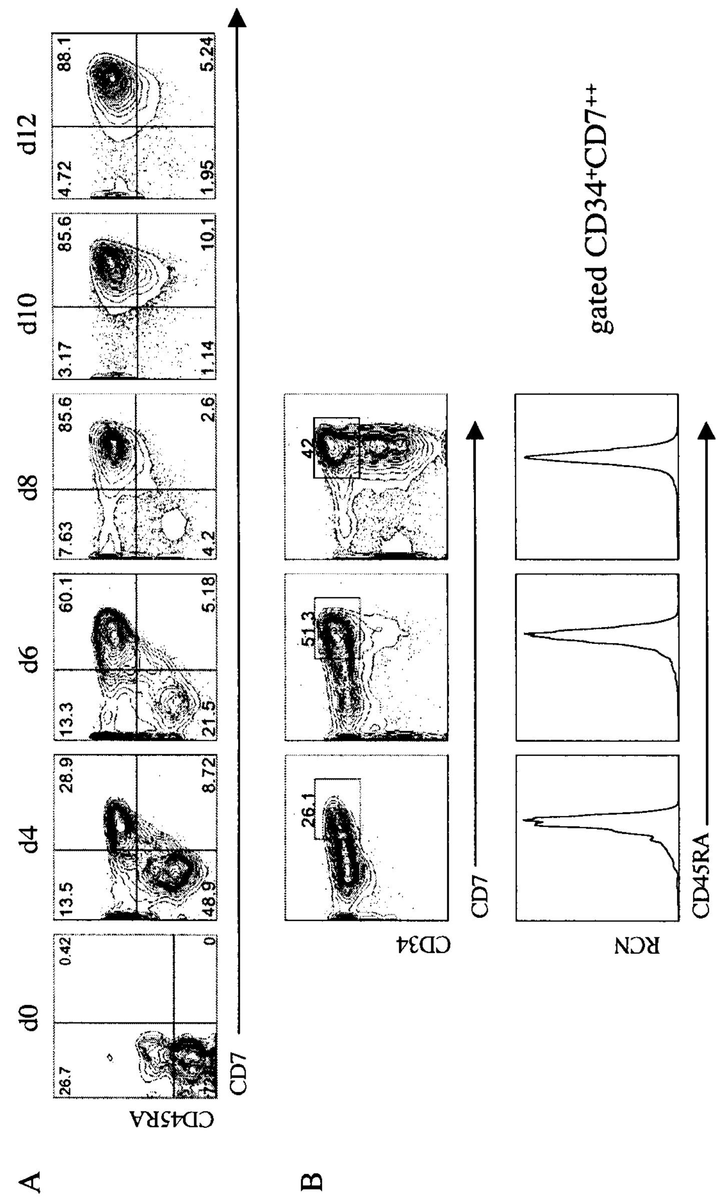
FIG. 2. Analysis for the presence of T-cell progenitors generated in vitro. (A) Flow cytometric analysis for the expression of CD7 and CD45RA from HSC/OP9-DL1 cocultures harvested at the indicated time-points, including a day 0 prior to the start of coculture. (B) Flow cytometric analysis of CD7 and CD34 expression from HSC/OP9-DL1 cocultures harvested at days 4, 6, and 8 (upper row), with CD45RA expression shown for cells gated as $CD34^+$ $CD7^{++}$ (lower row). Data are representative from 3 independent cocultures. Numbers in plots indicate percentage of cells within each quadrant, and RCN=relative cell number.

Thymus-seeding cells, identified as $CD34^{+}CD45RA^{hi}CD7^{+}$, have been shown to be present in UCB (Haddad et al., 2004) or fetal bone marrow (Haddad et al., 2006). To determine whether a similar population can be generated in vitro, the inventors looked for cells bearing this phenotype at early coculture time points. Of note, the starting UCB-HSC population contained a subset of $CD34^{+}$ cells that expressed the CD45RA isoform at low levels (Hao et al., 2001; Payne and Crooks, 2002), however these cells were $CD7^{-}$ (FIG. 2A). The analysis showed that CD45RA expression is up-regulated within the first 4 days on $CD34^{+}$ cells, and by day 6 nearly all $CD34^{+}CD7^{++}$ cells express CD45RA (FIG. 2B). Thus, a population of $CD34^{+}CD7^{++}CD45RA^{+}$ cells displaying a thymic-colonizing phenotype, as seen in vivo (Haddad et al., 2004; Haddad et al., 2006), is present in vitro and may also possess thymus reconstituting potential.

Molecular Analysis of the Sequential Induction of T-Cell Development in Vitro.

Figure 3:
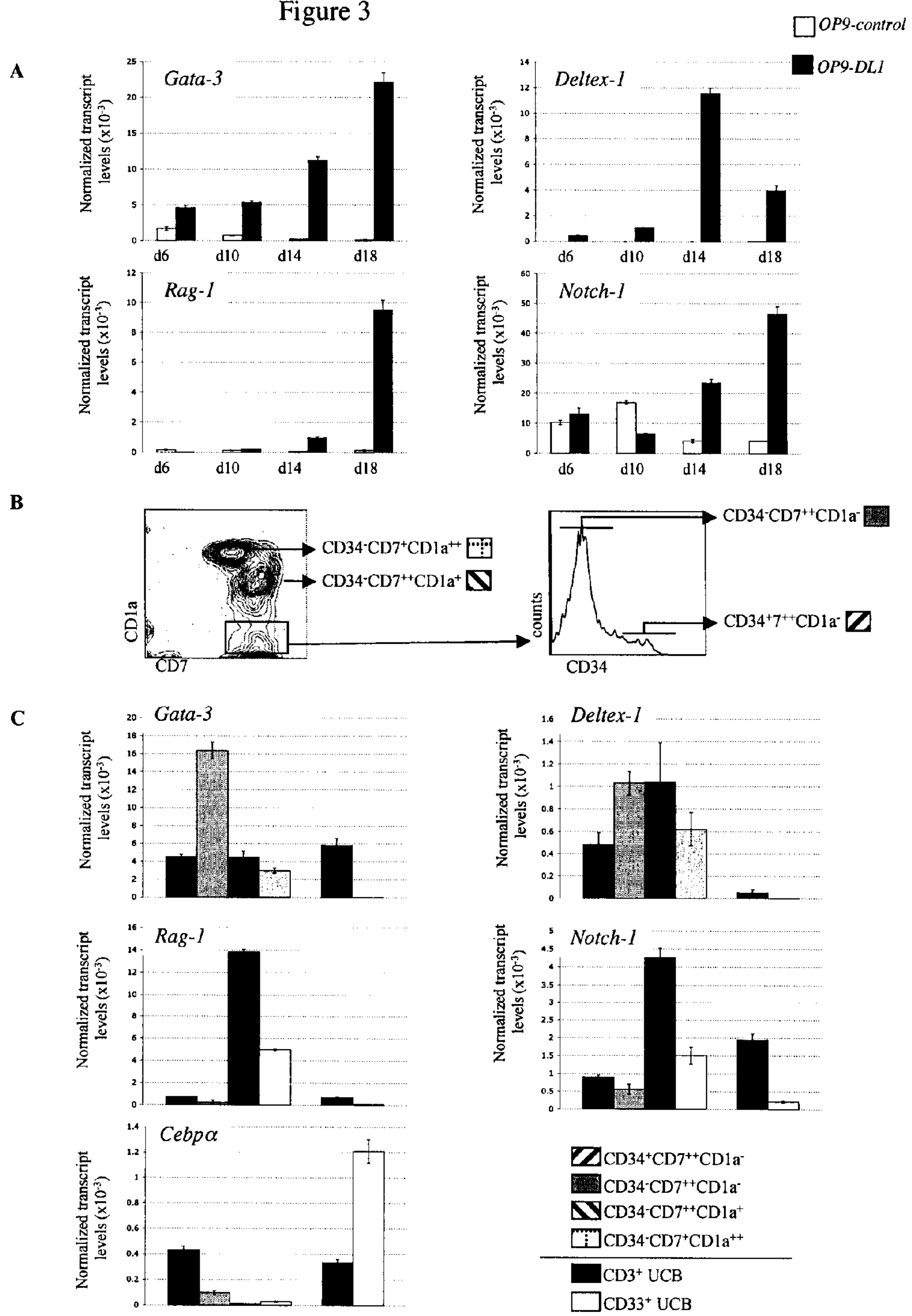
FIG. 3. Gene expression analysis of $CD34^+$ $CD38^{-/lo}$ HSCs cultured on OP9-DL1 cells. (A) Temporal kinetics of gene expression by quantitative real-time Q-PCR analysis from human $CD34^+$ $CD38^{-/lo}$ HSCs cultured on either OP9-control or OP9-DL1 cells for 6, 10, 14 and 18 days. (B) Flow cytometric analysis for the cell surface expression of CD7 and CD1a from a day 40 HSC/OP9-DL1 coculture, with CD34 expression shown for cells gated as $CD7^+CD1a^-$. (C) Gene expression analysis by Q-PCR from the coculture-derived subsets as indicated in (B), $CD34^+CD7^{++}$ $CD1a^-$, $CD34^-$ $CD7^{++}$ $CD1a^-$, $CD34^-$ $CD7^{++}$ $CD1a^+$, $CD34^-$ $CD7^+$ $CD1a^{++}$ see figure key. $CD3^+$ T cells and $CD33^+$ myeloid cells were purified from the $lineage^+$ fraction of UCB samples and served as controls. Transcript levels for the indicated genes were normalized to human β-actin, and these data are representative of three independent experiments, with the STD error bars shown corresponding to values obtained from triplicate wells within an individual experiment.

Although human HSC/OP9-DL1 cocultures exhibited a cellular expression pattern consistent with stages of T-cell development observed in the thymus, the precise temporal kinetics of Notch-dependent gene expression during early T-cell differentiation (Izon et al., 2002; Radtke et al., 2004) are undefined. The inventors examined the expression of Gata-3, Deltex-1, Rag-1, and Notch-1 transcripts from HSCs cocultured with OP9-control (GFP-only) or OP9-DL1 cells. As shown in FIG. 3A, expression of Gata-3, Deltex-1, Rag-1 and Notch-1 showed a general trend toward elevated transcript levels in OP9-DL1 as compared to OP9-control cocultures, with a clear difference starting at around day 14. Consistent with its role in early T-cell specification and commitment (Pai et al., 2003; Rothenberg and Taghon, 2005), Gata-3 expression was differentially induced early and steadily increased over time in OP9-DL1 cocultures. Deltex-1, a known Notch-induced target gene (Pear and Radtke, 2003), was also specifically up-regulated as early as day 6 in OP9-DL1 cocultures. Rag-1, an essential gene for TCR gene rearrangements (Shultz et al., 2000), became differentially up-regulated in OP9-DL1 cocultures by day 14. Finally, expression of Notch-1 was observed throughout in both cocultures, but was clearly up-regulated as a consequence of Delta-like-induced-signaling (Pear and Radtke, 2003).

Although the gene expression kinetics described above are consistent with the induction of T-lineage differentiation by Notch/Delta-like interactions, the inventors sought to more precisely characterize the changes in gene expression occurring at specific T-cell differentiation stages. To this end, subsets of CD7-expressing cells, with each subset representing a distinct and sequential stage of T-cell development, were analyzed. As shown in FIG. 3B, the developmental progression of CD7-expressing cells, from a day 40 OP9-DL1 coculture, can be ordered sequentially based on the loss of CD34 and the gain of CD1a expression into 4 stages: $CD34^{+}CD7^{++}CD1a^{-}$, $CD34^{-}CD7^{++}CD1a^{-}$, $CD34^{-}CD7^{++}CD1a^{++}$ and finally $CD34^{-}CD7^{+}CD1a^{++}$. These subsets, as well as T-cells ($CD3^{+}$) and myeloid cells ($CD33^{+}$) sorted from UCB as lineage controls, were then examined for the expression of Gata-3, Deltex-1, Rag-1, Notch-1, as well as the myeloid-specific gene Cebpα (Dahl et al., 2003) (FIG. 3C). Up-regulation of Gata-3 transcripts became apparent as $CD7^{++}$ cells lose CD34 surface expression, and remained high during the next stage, but is then reduced at later stages, which is in keeping with previous observations (Rothenberg and Taghon, 2005). Deltex-1 was up-regulated in each of the CD7-expressing subsets when compared to either $CD3^{+}$ mature T-cells or $CD33^{+}$ myeloid cells. Of note, Rag-1 and Notch-1 transcript up-regulation was most pronounced at the $CD34^{-}CD7^{++}CD1a^{+}$ stage, consistent with the role of these genes in the generation and functional outcomes of the pre-TCR complex (Ciofani et al., 2004). As expected, when CD34 expression is extinguished, CD7-expressing cells become more restricted to the T-cell lineage, which parallels the observed loss of Cebpα expression within these subsets.

Taken together, human HSC/OP9-DL1 cocultures display stage- and temporal-specific cellular and molecular signatures, which not only recapitulates key hallmarks of T-lymphopoiesis but also provides a simple and effective way to further dissect the developmental program of human T-cells.

Generation of Functional Human CD8 Sp T-Cells from HSCs Cultured with OP9-DL1 Cells.

Figure 4:
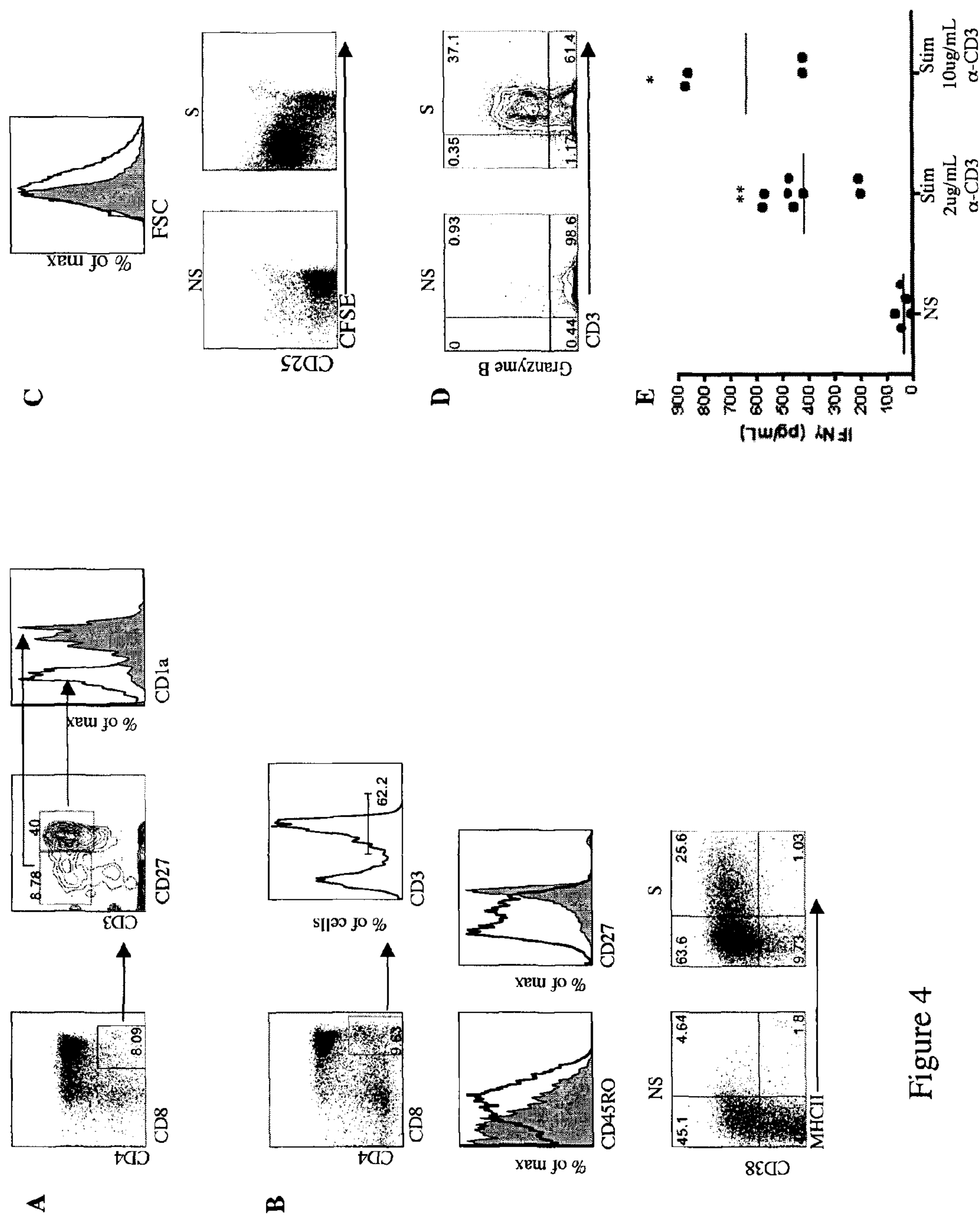
FIG. 4. Characterization of $CD8^+$ T cells generated in vitro. (A) Flow cytometric analysis for the expression of CD8 and CD4 from human UCB-derived HSCs cultured on OP9-DL1 cells for 65 days. $CD8^+CD4^-$ single positive (SP) cells were gated, as indicated, and analyzed for the expression of CD27 and CD3, with CD1a expression shown for cells gated as $CD3^+$ $CD27^-$ or $CD27^+$ (shaded and clear histograms, respectively). (B-D) Day 60-70 HSC/OP9-DL1 coculture-derived CD8 SP T cells were purified as shown, $CD8^+$ $CD4^-$ and $CD3^+$, and stimulated anti-CD3/CD28 mAbs for 5 days. Flow cytometric analyses of stimulated (S) or control (non-stimulated, NS) $CD8^+$ $CD3^+$ cells (clear and shaded histograms, respectively) for the expression of CD45RO, CD27, MHC-class II and CD38 (B); CFSE levels and CD25 (lower row), with cell size measured by Forward-light Scatter (FSC) intensity (C); and, CD3 and intracellular Granzyme B (D) are shown. (E) Human IFNγ levels from culture supernatants derived from the above-outlined experiment (B) were determined by ELISA. Statistical significant was measured by unpaired t-Test. *($p<0.005$) 2 μg/ml anti-CD3/CD28 stimulated group versus non-stimulated control. **($p<0.0005$) 10 μg/ml anti-CD3/CD28 versus non-stimulated control. Data are representative of at least 3 independent experiments, with the exception of the data from the 10 μg/ml stimulations, which are derived from 2 independent experiments.

The inventors have previously reported the ability to generate $CD4^{+}CD8^{+}$ T-lineage cells from human HSC/OP9-DL1 cocultures (La Motte-Mohs et al., 2005), however whether functional T-cells could be generated was not assessed. To address this, the inventors analyzed long-term cocultures, and FIG. 4A shows the presence of both DP and SP subsets from a day 65 coculture. The inventors further examined the CD8 SP subset present in these cultures for the expression of CD3 and CD27 (Res and Spits, 1999; Vanhecke et al., 1995) typically expressed on mature T-cells. Amongst the SP CD8 cells (SP8s) found in late cocultures, about 50-60% expressed CD3/αβTCR. Of note, the majority of $CD3^+$ SP8s were found to co-express CD27. In addition, $CD27^+CD3^+SP8s$ were also found to lack CD1a expression, which is indicative of functional maturity (Res et al., 1997). This is in contrast to $CD27^-$ $CD3^+$ SP8s that continued to express CD1a, which is characteristic of the preceding stage in T-cell differentiation (Res et al., 1997).

To address the functional status of in vitro-generated SP8s, the inventors sorted the CD3/TCR-expressing subset (FIG. 4B) and examined whether these cells had the capacity to up/down-regulate downstream differentiation markers, proliferate, express cytolytic effector-function molecules, and secrete γ-interferon (IFNγ) following stimulation. As shown in FIG. 4C, a blast-like appearance based on forward size scatter is seen in stimulated (S) cells as compared to non-stimulated (NS) cells. Additionally, stimulated cells up-regulated CD45RO, CD38 and MHC-class II expression and down-regulated CD27 expression, as compared to non-stimulated cells (FIG. 4B). This complex phenotype is unique to activated human T-cells (Holling et al., 2002; Ko et al., 1979) and consistent with full effector maturation and greater cytolytic capability (Hamann et al., 1997; van Baarle et al., 2002). Furthermore, to address the extent of cellular proliferation induced by TCR-stimulation, sorted $CD3^+CD8^+$ T-cells were loaded with CFSE. FIG. 4C shows that stimulated cells undergo many rounds of cell division as indicated by the loss of CFSE compared to non-stimulated cells, with proliferating cells also displaying marked up-regulation of CD25 expression.

To determine whether in vitro-derived SP8s can be induced to express cytotoxic/effector-function molecules, the expression of Granzyme-B and IFNγ were assessed. Intracellular Granzyme-B expression was detected in ~40% of stimulated $CD3^+CD8^+$ T-cells, as compared to non-stimulated cells that failed to express Granzyme-B (FIG. 4D). Finally, supernatants from wells containing in vitro-generated SP8s were analyzed for the presence of IFNγ following stimulation. As shown in FIG. 4E, supernatants from stimulated cells showed a significant dose-dependent increase in the amount of IFNγ, as compared to non-stimulated cells.

$CD34^+CD38^-$ and $CD34^+CD38^{lo}$ UCB Cells Exhibit High T-Lymphopoietic Potential.

Figure 8:
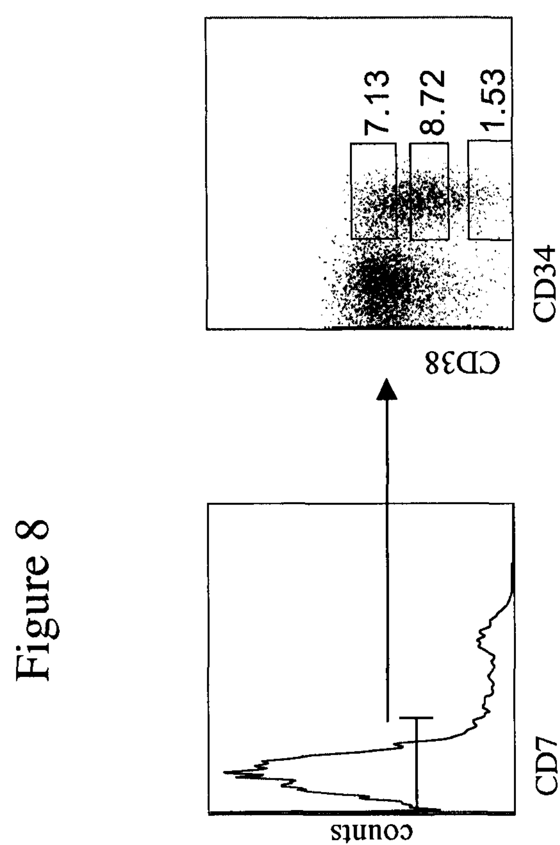
FIG. 8. Characterization of the UCB-derived $CD34^+$ subsets used for the progenitor frequency determination in limiting dilution assay. Lineage-depleted UCB cells were gated to exclude CD7-expressing cells, sorted into $CD34^+$ $CD38^-$, $CD34^+$ $CD38^{lo}$, and $CD34^+$ $CD38^{+/hi}$ subsets, plated onto OP9-DL1 cells, and cultured for 11 days. Results from the limiting dilution assay are shown in Table I.

Several studies have provided evidence that the UCB-$CD34^+$ stem cell pool is heterogeneous in terms of its repopulation, differentiation and renewal potential (Guenechea et al., 2001; Hogan et al., 2002). Indeed, the $CD34^+$ population can be subfractionated into distinct subsets based on CD38 expression (Guenechea et al., 2001; Hogan et al., 2002; Mazurier et al., 2004). The $CD38^-$ subfraction contains primitive precursors capable of long-term reconstitution with slower engraftment kinetics (Hogan et al., 2002). Conversely, UCB cells from the $CD34^+CD38^{lo}$ or $CD38^{+/hi}$ subsets exhibit different characteristics, giving rise to rapid myeloid-erythroid differentiation with short-term repopulating ability (Guenechea et al., 2001; Hogan et al., 2002; Mazurier et al., 2004). However, these studies did not address the frequency of progenitors with T-lineage potential among these different $CD34^+$ subsets. To determine the T-progenitor frequency of the various UCB-$CD34^+$ subsets, $CD34^+CD38^-$, $CD34^+CD38^{lo}$ and $CD34^+CD38^{+/hi}$ cells were sorted (FIG. 8) and placed at limiting cell numbers into wells containing OP9-DL1 cells. As shown in Table I, $CD34^+CD38^-$ or $CD34^+CD38^{lo}$ cells gave rise to T-lineage cells with similar overlapping frequencies of 1 in 4.8 and 1 in 3.9, respectively, while the $CD34^+CD38^{+/hi}$ subset possessed a nearly 5-fold diminished T-lineage progenitor frequency of 1 in 19. Thus, the $CD34^+CD38^-$ and $CD34^+CD38^{lo}$ fraction contains a greater frequency of cells that can give rise to T-lineage cells.

In Vitro-Generated pro-T Cells Show Thymus Reconstituting Ability.

The earliest cell thought to colonize the thymus has been described as a $CD34^+$ cell expressing CD45RA and CD7 (Haddad et al., 2004; Haddad et al., 2006). The inventors have shown that in HSC/OP9-DL1 cocultures cells with this phenotype are present (FIG. 2), however whether these cells also possess thymus-reconstituting potential remained untested.

Figure 5:
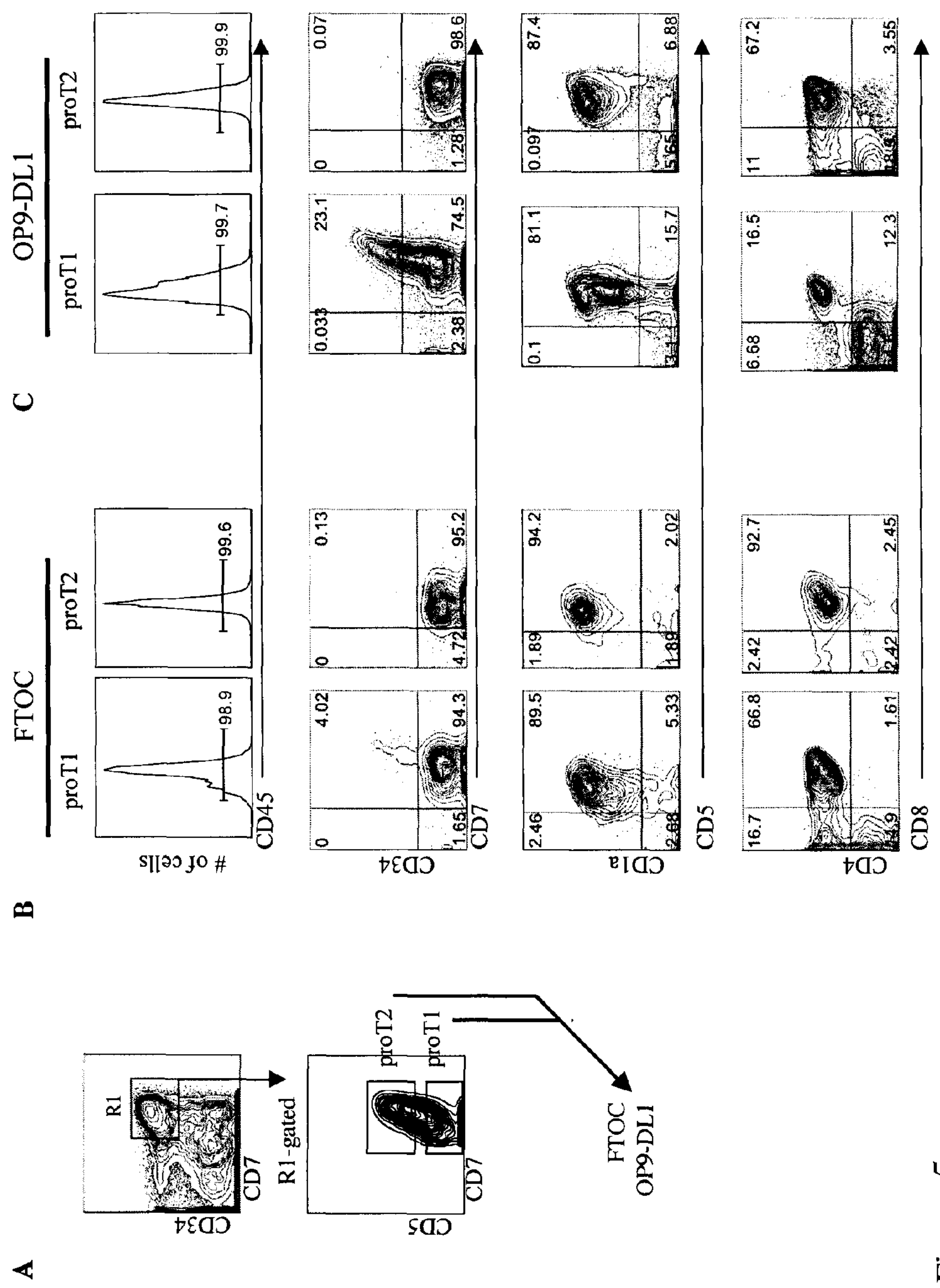
FIG. 5. Analysis of engraftment and differentiation by in vitro-derived progenitor T cell subsets in FTOC. UCB $CD34^+$ $CD38^{-/lo}$ HSCs were differentiated for 13 days on OP9-DL1 cells and $CD34^+$ $CD7^{++}$ $CD5^-$ (proT1) and $CD34^+$ $CD7^{++}$ $CD5^+$ (proT2) subsets were sorted by flow cytometry as indicated in (A), and placed into FTOC (B) or placed back onto OP9-DL1 cells (C) for 19 days. Cells were harvested and analyzed for cell surface expression of CD45, CD7, CD34, CD5, CD1a, CD8, and CD4. Data are representative of 3 independent experiments in which $1.5\times10^4$ sorted proT subsets were placed either into fetal thymus lobe-pairs or in wells containing OP9-DL1 cells.

To test whether in vitro-generated cells that share a thymus-colonizing cell surface phenotype are able to engraft a thymus, the inventors utilized a hybrid human/mouse FTOC approach (Fisher et al., 1990). Additionally, the inventors further dissected the $CD34^+CD45RA^+CD7^{++}CD1a^-$ progenitor subset based on the presence or absence of CD5 expression, which, as shown in FIG. 5A (and data not shown), CD5 is expressed on ~45% of these cells. To determine whether these T-progenitor subsets have the potential to engraft and differentiate within a host thymus, $CD34^+CD45RA^+CD7^{++}CD1a^-$ cells that are either $CD5^-$ or $CD5^+$ (hereafter referred to as proT1 and proT2, respectively) were sorted from a day 13 HSC/OP9-DL1 coculture and placed in FTOCs for 19 days (FIG. 5B). Additionally, the same subsets were placed back onto OP9-DL1 cells (FIG. 5C) and their development compared to that occurring in FTOC.

Shown in FIG. 5B, both proT1 and proT2 subsets successfully engrafted the FTOCs, and their progeny accounted for nearly all of the cells present in the lobes, based on human CD45 expression (≥95%). Additionally, the reconstituted FTOCs contained T-cells that were derived from either the proT1 or proT2 subsets. While the input proT1 cells were initially $CD34^+CD7^+CD5^-$, nearly all of the cells within the engrafted lobes had differentiated into $CD34^-CD5^+CD1a^+$ T-lineage cells, with 67% also coexpressing CD4 and CD8 and 2-16% expressing either CD8 or CD4, with the majority of these being CD4ISPs (data not shown). Similarly, the proT2 cells, which initially expressed CD5, also gave rise to T-cells, however with an increase in the frequency of DP cells (93%). This difference may relate to the later differentiation state of the proT2 cells, which as demonstrated in FIG. 21, purified proT1 cells gave rise to cells with the proT2 phenotype within 24 hours and the majority of these cells reached the next stage by 48 hours. Additionally, purified proT2 cells did not give rise to cells with the proT1 phenotype. The precursor-product relationship from proT1 to proT2 is further highlighted by the presence of a small fraction (4%) of $CD34^+CD7^{++}$ cells remaining in FTOC seeded with proT1 but not proT2 cells. Keeping with this, proT1 cells placed back onto OP9-DL1 cells also showed the presence of a $CD34^+CD7^{++}$ progenitor population, which was absent in proT2 cultures (FIG. 5C). Nevertheless, both proT1 and proT2 cells showed a similar overall ability to continue to differentiate along the T-lineage pathway in these cocultures, giving rise to $CD1a^+$ and CD4/CD8-expressing cells.

Since proT1 and proT2 cells share a similar progenitor phenotype with cells found in the human thymus that have been shown to also possess NK-lineage potential, the inventors addressed whether NK cells could also be generated from these subsets. Consistent with this, the inventors confirmed that in vitro-derived proT1 and proT2 cells give rise to NK cells when cultured on OP9-control cells, supplemented with IL-15 (FIG. 22). These results are consistent with studies demonstrating the presence of cells with dual T/NK potential within the $CD34^+CD7^{++}$ thymocyte subset (Sanchez et al., 1994; Spits et al., 1995). Of note, both proT1 and proT2 cells when cultured on OP9-DL1 cells did not give rise to NK cells, rather they continued to differentiate along the T cell pathway (FIG. 22), which is consistent with the known role of Notch signaling in maintaining commitment to the T-lineage while inhibiting alternate lineage outcomes. Additionally, methylcellulose assays were performed to test the capacity of in vitro generated proT cells to give rise to erythroid, myeloid and granulocytic lineages (Table III). While, sorted CD34+ UCB-HSCs generated colonies for all lineages, in vitro-generated proT cells displayed a markedly reduced capacity for non-lymphoid colony formation, including an absence of erythroid potential from the proT2 cells, further highlighting their diminished ability to generate alternative lineage outcomes with the favored acquisition of lymphoid potential.

Although both proT1 and proT2 cells can give rise to T-cells, it remained unclear whether these subsets contained a similar progenitor frequency to reconstitute a host thymus. To address this, sorted proT1 and proT2 cells were placed in limiting cell numbers in FTOCs or on OP9-DL1 cells for 7 days, and analyzed by flow cytometry for the presence of human T-lineage cells. The results shown in Table II demonstrate that the proT2 subset displayed a 3-fold higher T-lineage engraftment frequency than that of the proT1 cells (1:400 and 1:1400, respectively). To further examine whether this difference was cell intrinsic, the T-progenitor frequency of these subsets was determined in a limiting dilution assay with OP9-DL1 cells. Of note, and in contrast to the progenitor frequencies observed in FTOCs, the results from the cocultures revealed that both pro-T subsets possess a similar and high (~1:2) progenitor frequency (Table II).

Figure 6:
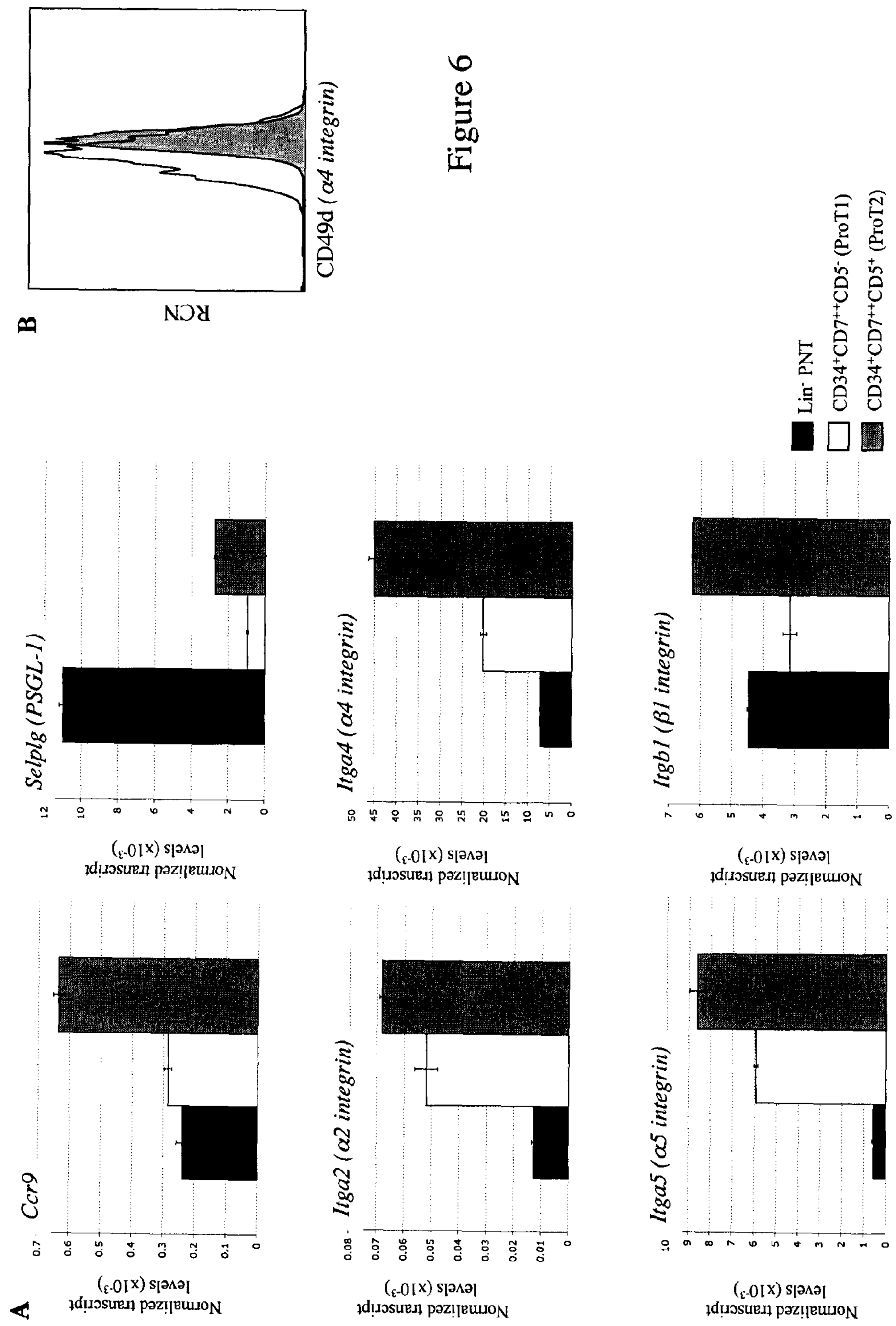
FIG. 6. Gene expression analysis of $CD34^+$ $CD7^{++}$ $CD5^-$ and $CD34^+$ $CD7^{++}$ $CD5^+$ proT cell subsets. (A) Q-PCR analysis of $CD34^+$ $CD7^{++}$ $CD5^-$ (proT1) and $CD34^+$ $CD7^{++}$ $CD5^+$ (proT2) cells purified by flow cytometric cell sorting from a day 14 HSC/OP9-DL1 coculture. Thymocytes obtained from the $Lin^-$ fraction of a human post-natal thymus (PNT) served as a control sample. Transcript levels for the indicated genes [Ccr9 (CD199), Selplg1 (PSGL-1, CD162), Itga2 (α2, CD49b), Itga4 (α4, CD49d), Itga5 (α5, CD49e), and Itgb1 (β1, CD29)] were normalized to human β-actin. These data are representative of 3 independent experiments, with the STD error bars shown corresponding to values obtained from triplicate wells within an individual experiment. (B) Flow cytometric analysis for cell surface expression of CD49d on gated $CD34^+$ $CD7^{++}$ $CD5^-$ (proT1, open) and $CD34^+$ $CD7^{++}$ $CD5^+$ (proT2, shaded) cells from a day 11 HSC/OP9-DL1 coculture.

In light of these findings, it would appear that human pro-T cells, which otherwise display a similarly high T-cell progenitor frequency when assayed on the OP9-DL1 monolayer, possess a differential capability to engraft a mouse thymus lobe in vitro, which may relate to differences in the expression of molecules important for entry or niche occupancy within the thymus. To determine a potential mechanism for the observed difference in engrafting ability, the inventors analyzed by Q-PCR for the expression of genes associated with thymus homing or entry (Arroyo et al., 1996; Benz and Bleul, 2005; Goldschneider, 2006; Hirsch et al., 1996; Lai and Kondo, 2007; Rossi et al., 2005; Schwarz et al., 2007). FIG. 6A shows that proT2 cells express higher transcript levels of CCR9 (CD199), PSGL-1 (CD162), CD49b ($\alpha$2 integrin), CD49d ($\alpha$4 integrin) and CD49e ($\alpha$5 integrin). A similar trend of elevated expression was observed for CD29 ($\beta$1 integrin) in proT2 cells. Additionally, flow cytometric analysis of these subsets confirmed that proT2 cells express higher levels of CD49d than proT1 cells (FIG. 6B). These data are consistent with previous findings (Arroyo et al., 1996; Hirsch et al., 1996) that point to the CD49d/CD29 heterodimer, which binds to VCAM-1 (CD106) expressed on thymus stromal cells, as well as CCR9 and PSGL-1 as important players in facilitating thymus entry by the proT2 cell subset.

In Vitro-Generated Pro-T Cells Injected into Immunodeficient Mice Exhibit Thymic Reconstitution Ability In Vivo.

The inventors' finding that human pro-T cells generated in OP9-DL1 cells could exhibit thymic reconstitution potential in vitro when assayed in FTOC, suggested the possibility that human pro-T cells would similarly display thymic reconstitution potential when assayed in vivo. To ascertain whether in vitro-generated progenitor-T cells can effectively reconstitute the T cell compartment in vivo, the inventors have utilized two immunodeficient strains of mice (nonobese diabetic/severe combined immunodeficient (NOD/SCID$\gamma_c^{-/}$) (Greiner et al., 1998; Ito et al., 2002; Kollet et al., 2000; Shultz et al., 1995; Vila-Coro et al., 2000) mice and RAG2-deficient, gamma-chain ($\gamma_c$) deficient (RAG2$^{-/-}\gamma_c^{-/-}$) (Goldman et al., 1998; Mazurier et al., 1999)) that have been reported to support the engraftment of human $CD34^+$ CB-derived cells (Gimeno et al., 2004; Hogan et al., 1997; Traggiai et al., 2004).

Figure 11:
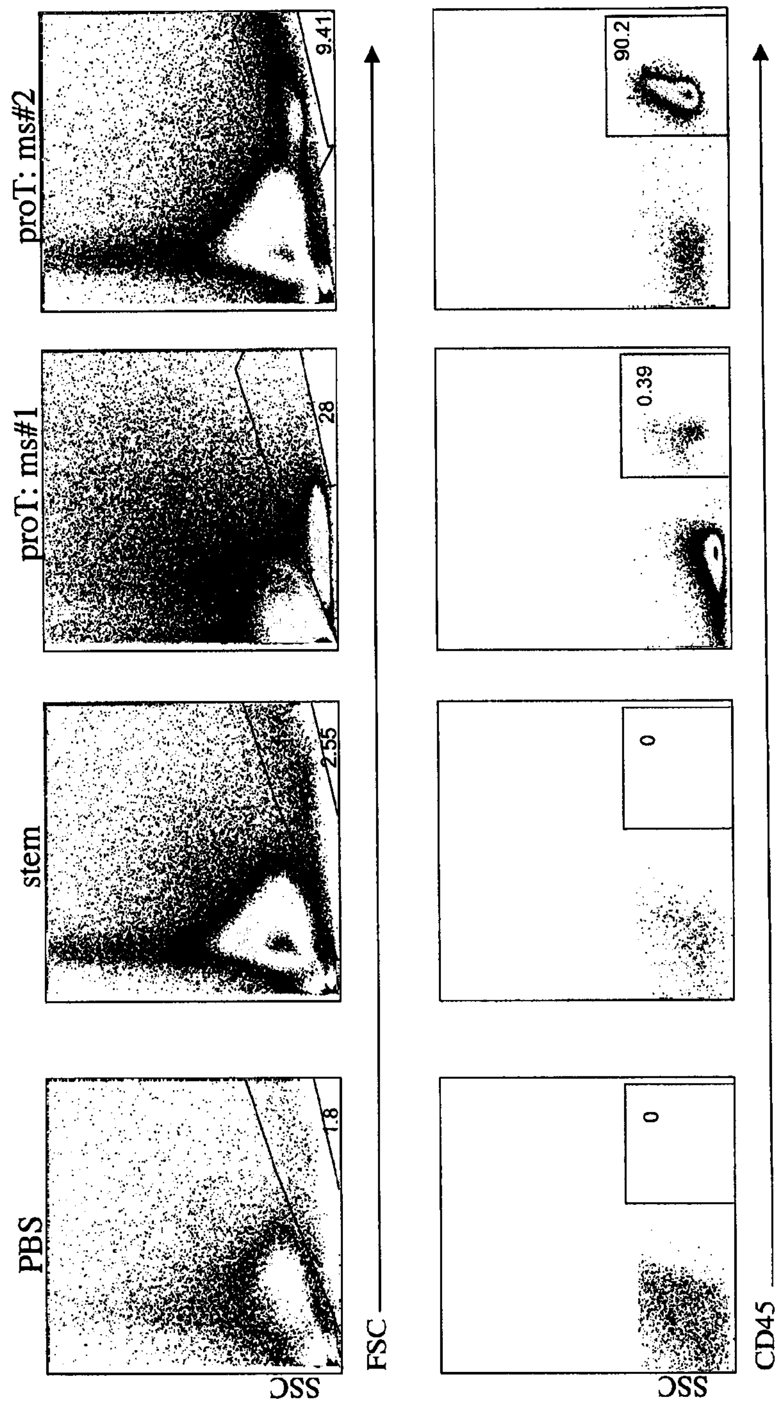
FIG. 11. (Top panel) Flow cytometric analysis and gating on lymphocytes by FSC and SSC gating in thymus of indicated mice. (Lower panel) Following live lymphocyte gating, cells were analyzed based on SSC and human CD45 staining. Numbers in plots indicate percentage of cells within each quadrant.
Figure 12:
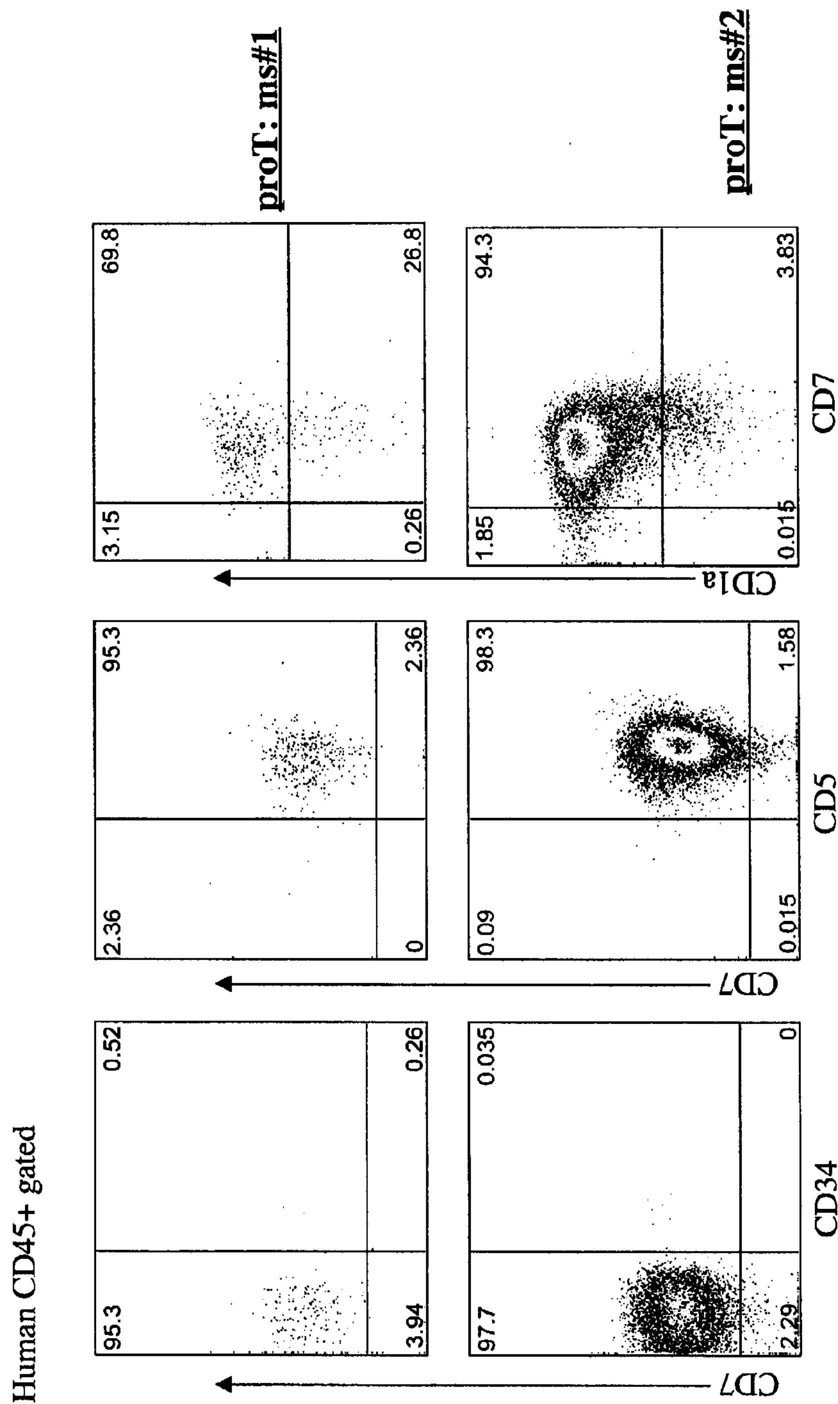
FIG. 12. $CD45^+$-gated flow cytometric analysis for the expression of CD34, CD7, CD5 and CD1a from thymuses of two reconstituted mice. Numbers in plots indicate percentage of cells within each quadrant.
Figure 13:
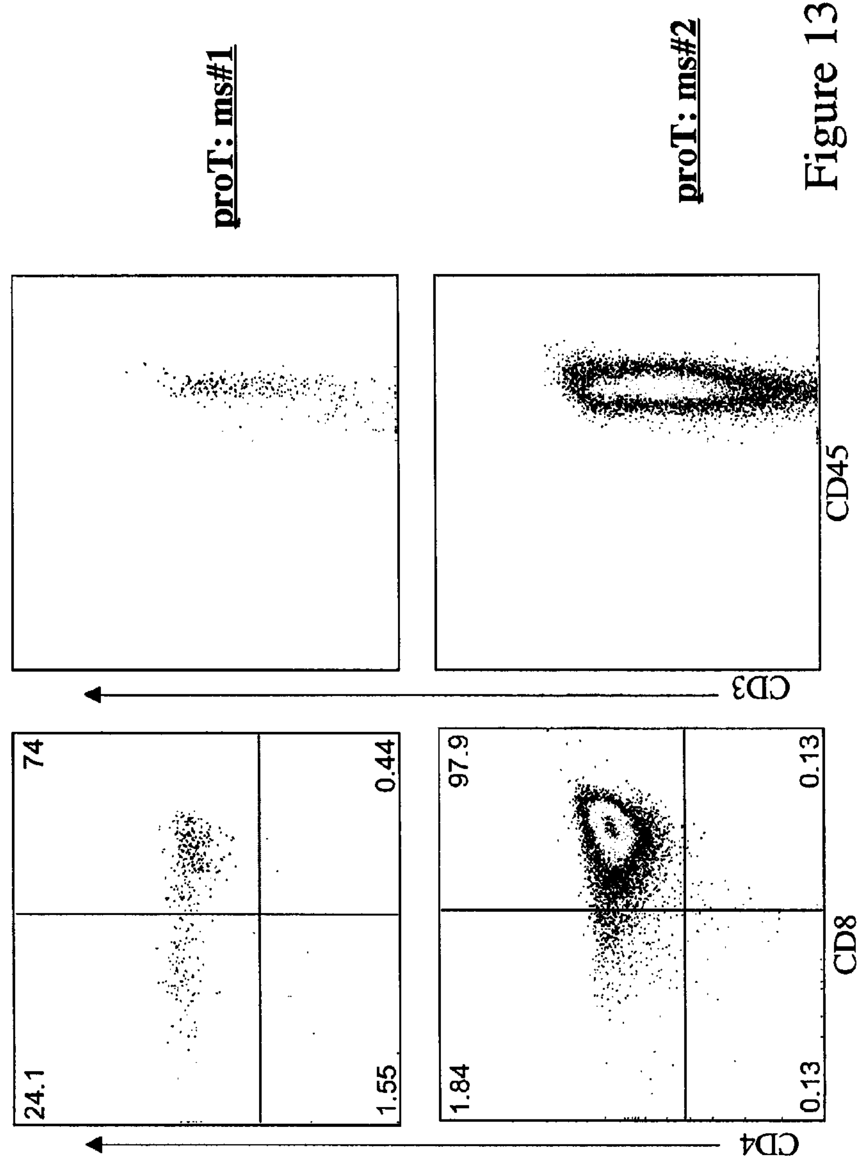
FIG. 13. CD45+-gated flow cytometric analysis for the expression of CD4, CD8, and CD3 cell surface expression from thymuses of two reconstituted mice. Numbers in plots indicate percentage of cells within each quadrant.

As seen in FIG. 11, RAG2$^{-/-}\gamma_c^{-/-}$ mice injected intrahepatically with OP9-DL1 coculture derived-bulk human progenitor-T cells ($CD34^+CD7^+$) displayed human hematopoietic engraftment potential within the thymus as early as ~3 weeks post injection as evidenced by the expression of a distinct lymphocytic population that expressed human CD45. Although a lymphocytic population could be detected to a lesser degree within the thymus of RAG2$^{-/-}\gamma_c^{-/}$ mice injected intrahepatically with human $CD34^+$ stem cells or mock PBS control, these lymphocytes did not express human CD45 suggesting these cells were of mouse origin. Upon further analysis of RAG2$^{-/-}\gamma_c^{-/}$ mice injected with bulk pro-T cells, human $CD45^+$-expressing thymocytes displayed a phenotype consistent with T cell development (FIGS. 12 and 13). Although differences in overall cellularity were noted between the two RAG2$^{-/-}\gamma_c^{-/}$ mice injected intrahepatically pro-T cells, the vast majority of $CD45^+$-gated thymocytes expressed early markers of T cell differentiation such as CD7, CD5 and CD1a (FIG. 12). Specifically, ~95% of the thymocytes co-expressed CD7 and CD1a, suggesting pro-T cells efficiently committed to the T cell lineage rather than maintaining their input phenotype. Upon closer examination, these $CD45^+$-gated thymocytes also expressed more definitive markers of T cell differentiation such as CD4, CD8, and CD3 (FIG. 13). By far the vast majority of these cells exhibited a $CD4^+CD8^+$ double positive (DP) phenotype and could be broken down into CD3-positive and CD3-negative populations.

Figure 14:
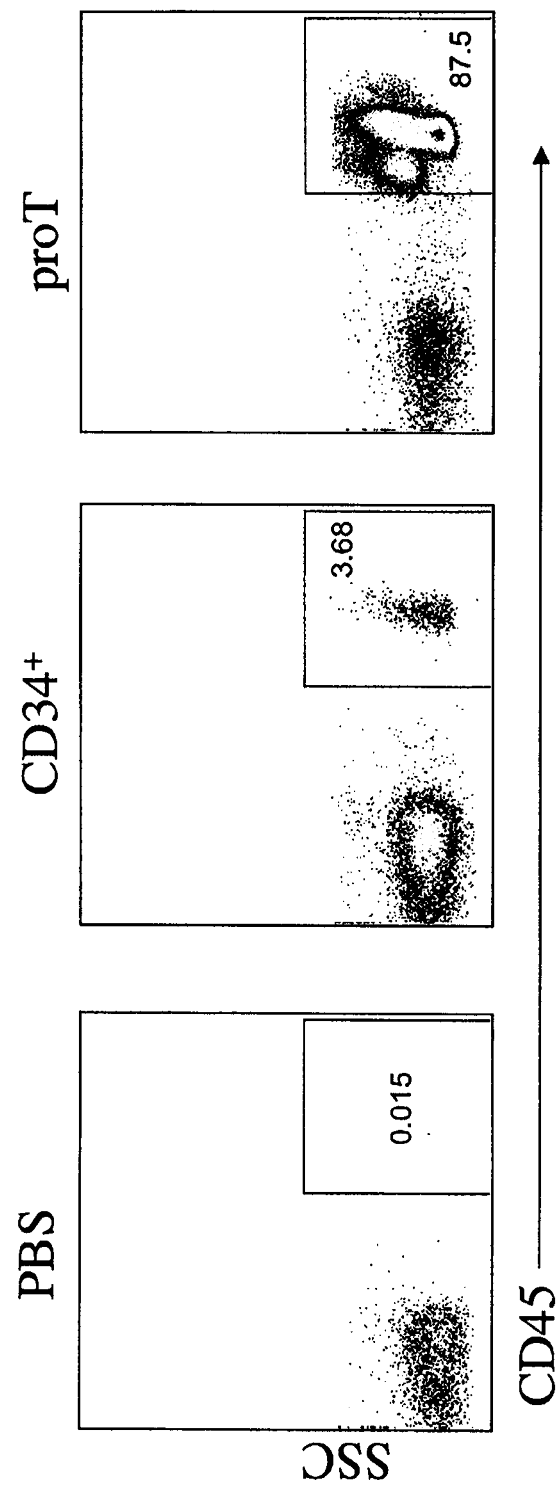
FIG. 14. Following live lymphocyte gating, cells were analyzed based on SSC and human CD45 staining from thymus of indicated mice. Numbers in plots indicate percentage of cells within each quadrant.

While PBS control injected RAG2$^{-/-}\gamma_c^{-/}$ mice did not spontaneously generate human $CD45^+$ cells in a $^{second}$ experiment, a small but detectable population of human $CD45^+$ cells were present when RAG2$^{-/-}\gamma_c^{-/}$ mice were injected intrahepatically at a higher dose with human $CD34^+$ hematopoietic stem cells (FIG. 14). Consistent with the previous experiment (FIG. 11), a robust population of $CD45^+$ thymocytes was present in RAG2$^{-/-}\gamma_c^{-/}$ mice that were injected with bulk pro-T cells (FIG. 14). When examined in greater detail (FIG. 15), the vast majority of the thymocytes in both the $CD34^+$ HSC-injected and $CD34^+CD7^+$ pro-T-injected RAG2$^{-/-}\gamma_c^{-/}$ mice expressed both CD4 and CD8. While single positive CD8 could be detected in the pro-T-injected mouse at three weeks, but not the $CD34^+$ HSC-injected mouse, the vast majority of the single positive cells expressed CD4, suggesting they could be either CD4-intermediate single positive cells (CD4-ISPs) or true CD4-SP cells. When $CD45^+$ cells that expressed high levels of CD3 were examined for the expression, both CD4 and CD8 SP cells could be detected, suggesting that the most of the of CD4 cells present within the reconstituted thymus of the RAG2$^{-/-}\gamma_c^{-/}$ mouse were CD4-ISP and not CD4-SP cells. In contrast to the $CD34^+$ HSC-injected mouse, which lacked CD4 and CD8 SP cells, the pro-T-injected mouse at three weeks differentiated further and more efficiently.

The ability of pro-T cells to display thymus reconstitution potential was also evaluated in the NOD/SCID$\gamma_c^{-/}$ strain of mouse (Greiner et al., 1998; Ito et al., 2002; Kollet et al., 2000; Shultz et al., 1995; Vila-Coro et al., 2000). As shown in FIG. 16, NOD/SCID$\gamma_c^{-/}$ mice injected intrahepatically with OP9-DL1 coculture derived-bulk human progenitor-T cells ($CD34^+CD7^+$), but not $CD34^+$HSCs, expressed human $CD45^+$ cells within their thymus, the vast majority of which, displayed an early T cell phenotype as evidenced by expression of CD5, CD7, and CD1a. Greater than 70% of these developing T cell committed thymocytes expressed CD4 on their cell surface, while ~2-20% of the CD4-positive cells co-expressed CD8, suggesting that CD4-ISP cells were transitioning to the DP stage. Taken together pro-T cells are capable of engrafting into two immunodeficient strains of mice.

Although experiments reconstituting mouse thymus in vitro indicated that the proT2 subset displayed a 3-fold higher T-lineage engraftment frequency than that of the proT1 cells (1:400 and 1:1400, respectively), it remained to be determined whether similar results would be observed in vivo. Since the inventors demonstrated the ability of bulk $CD34^{++}$ $CD7^{++}$ to engraft immunodeficient mice, the inventors tested the ability of each proT subset for their threshold for thymus reconstitution in vivo. Cells were sorted and either proT1 or proT2 cells were injected into individual neonatal mice at $2.5\times10^4$ or $1\times10^4$ cells, 10-25 fold lower cell numbers, respectively, than used in previous experiments in which bulk proT cells were used. Three weeks post-injection, the thymuses of mice were harvested and analyzed for engraftment. Results summarized in Table IV show that proT2 cells had a higher frequency of engraftment than proT1 cells (38% vs 14%) when $2.5\times10^4$ cells were injected. Furthermore, when only $1\times10^4$ cells were injected into mice, the inventors observe engraftment of both subsets with proT2 cells again displaying higher thymus engraftment frequency than their more immature counterpart.

Figure 15:
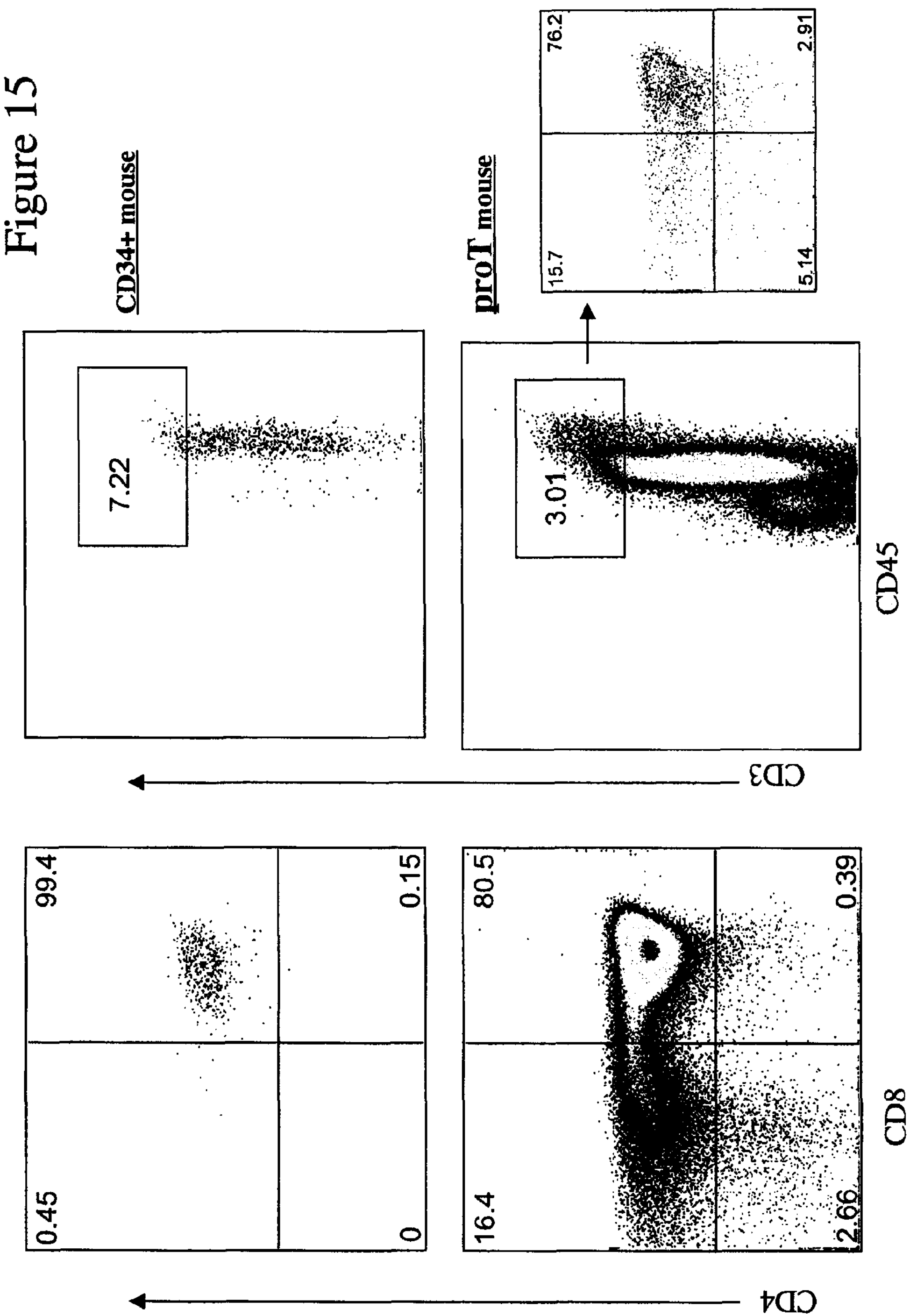
FIG. 15. $CD45^+$-gated flow cytometric analysis for the expression of CD4, CD8, and CD3 cell surface expression from the thymus of an HSC-reconstituted (top) and proT reconstituted (lower) mouse. Inset plot shows CD4 and CD8 expression on $CD3^{hi}$ gated cells. Numbers in plots indicate percentage of cells within each quadrant.
Figure 23A:
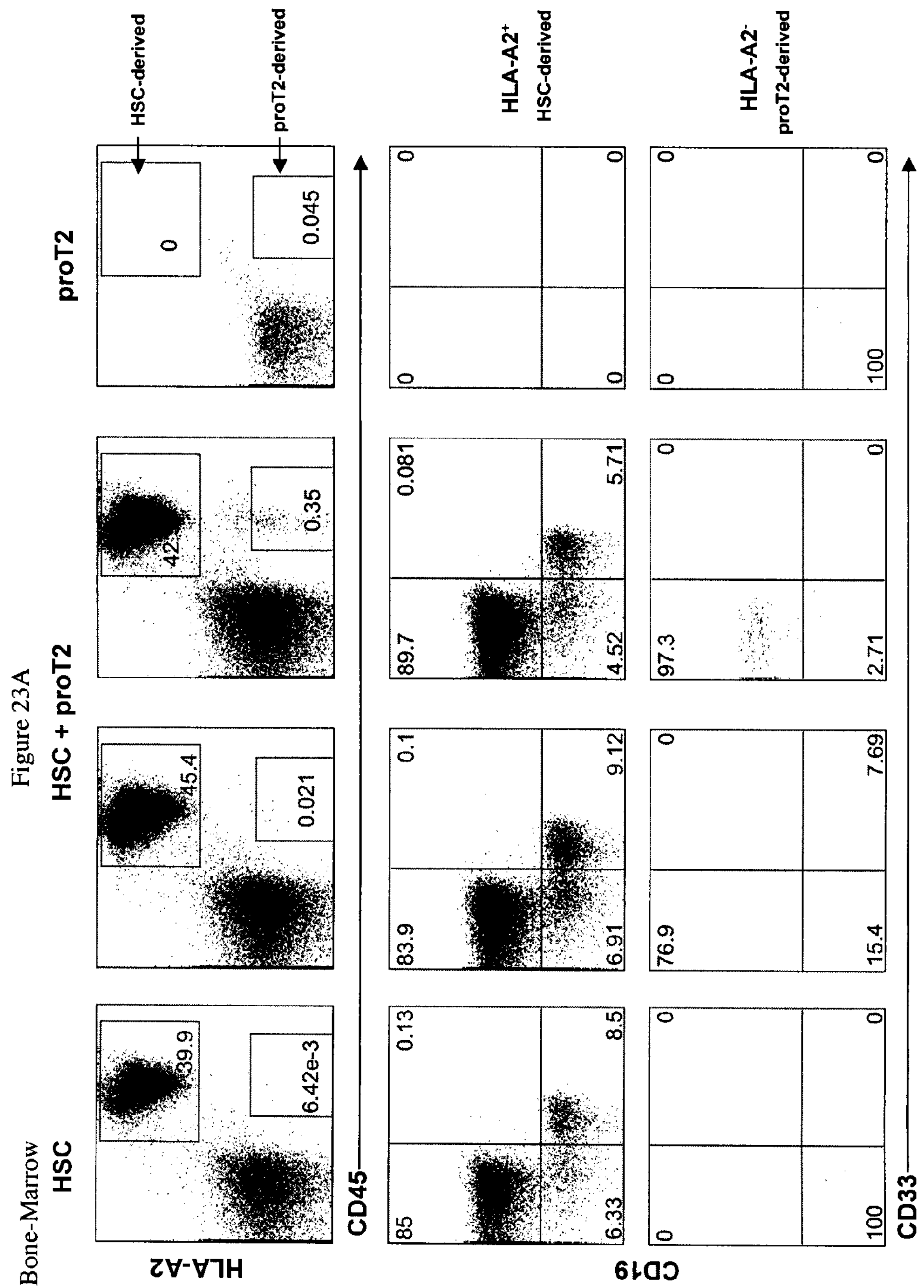
Figure 23B:
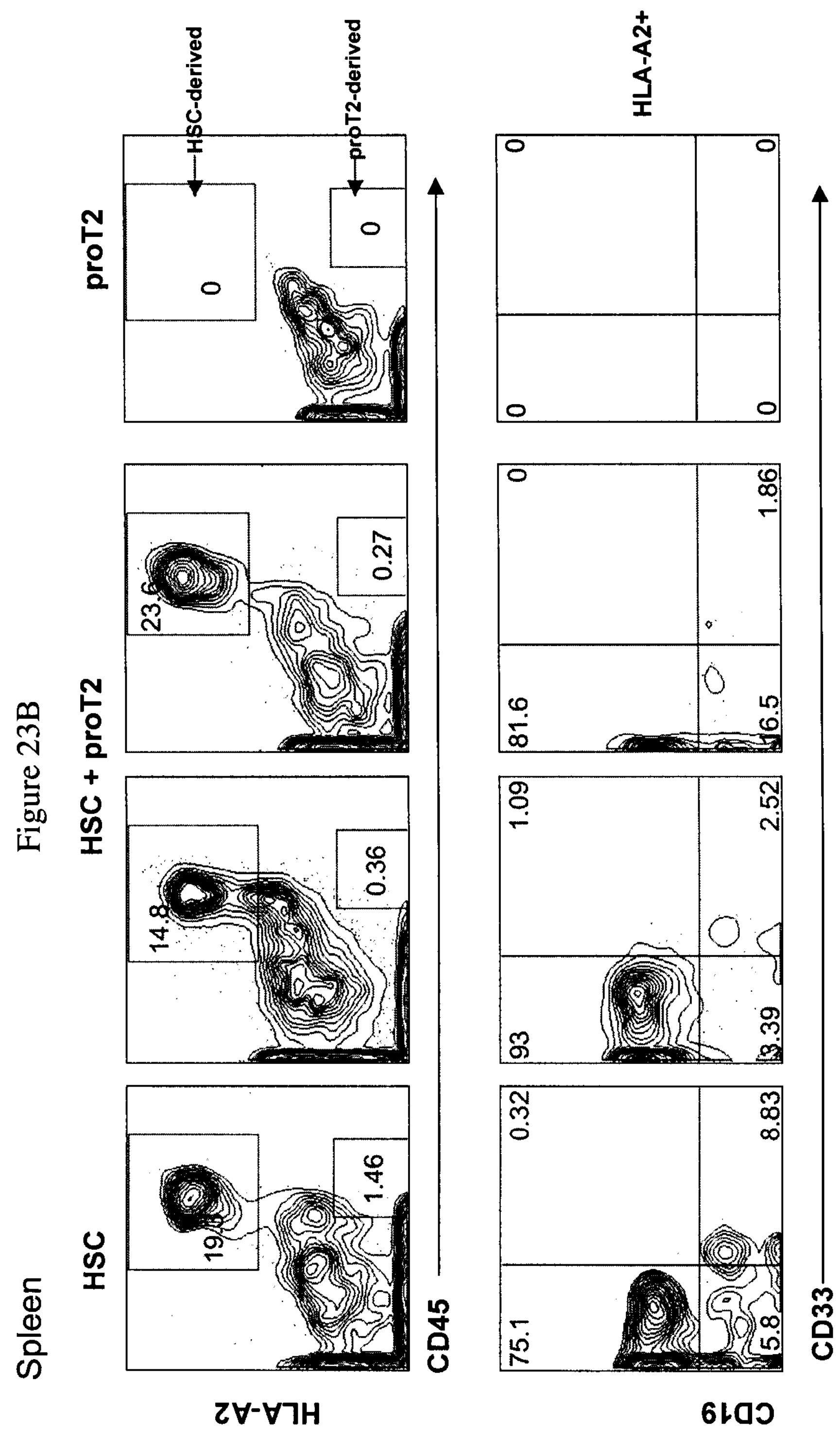
Figure 23C:
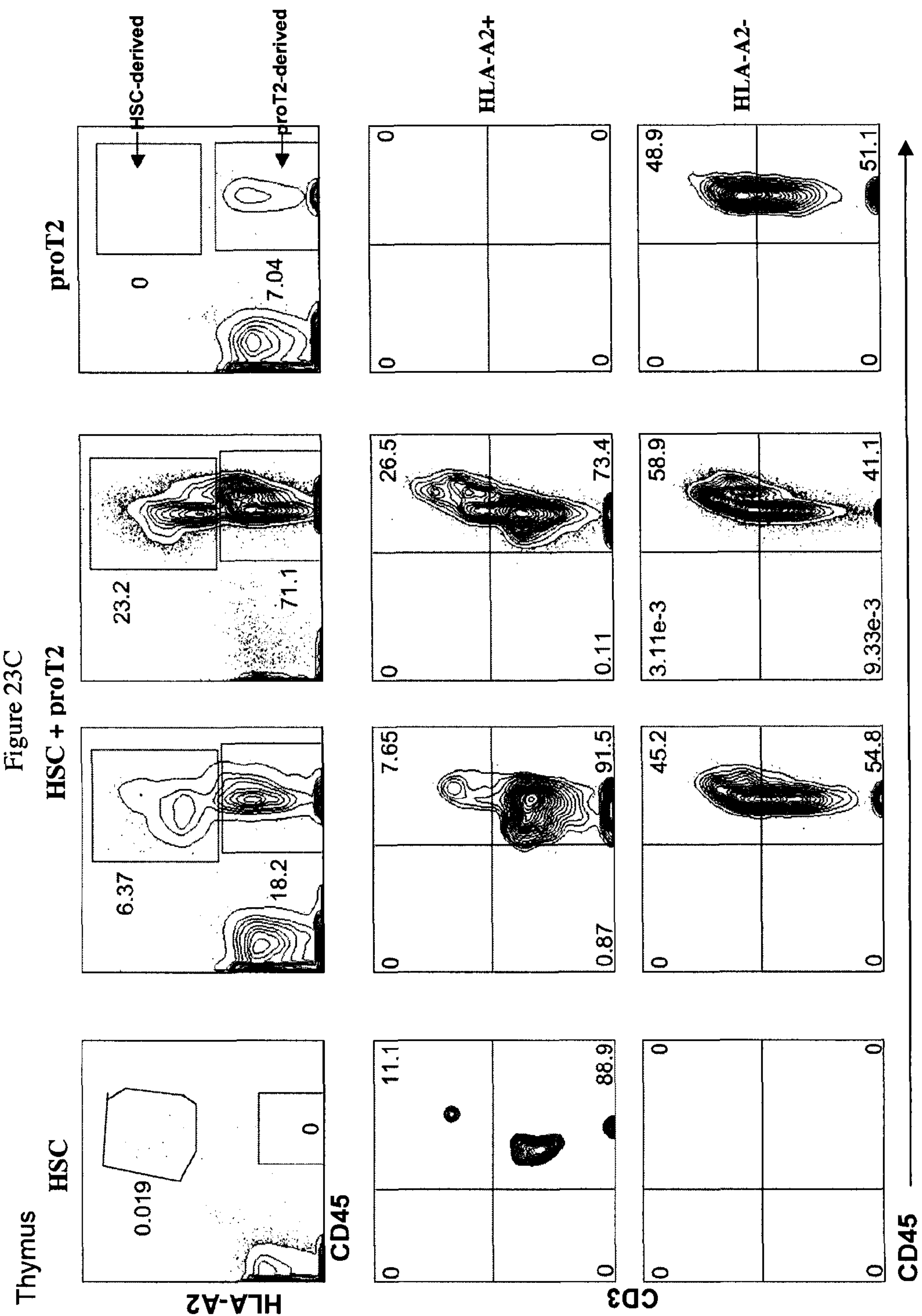
Figure 23D:
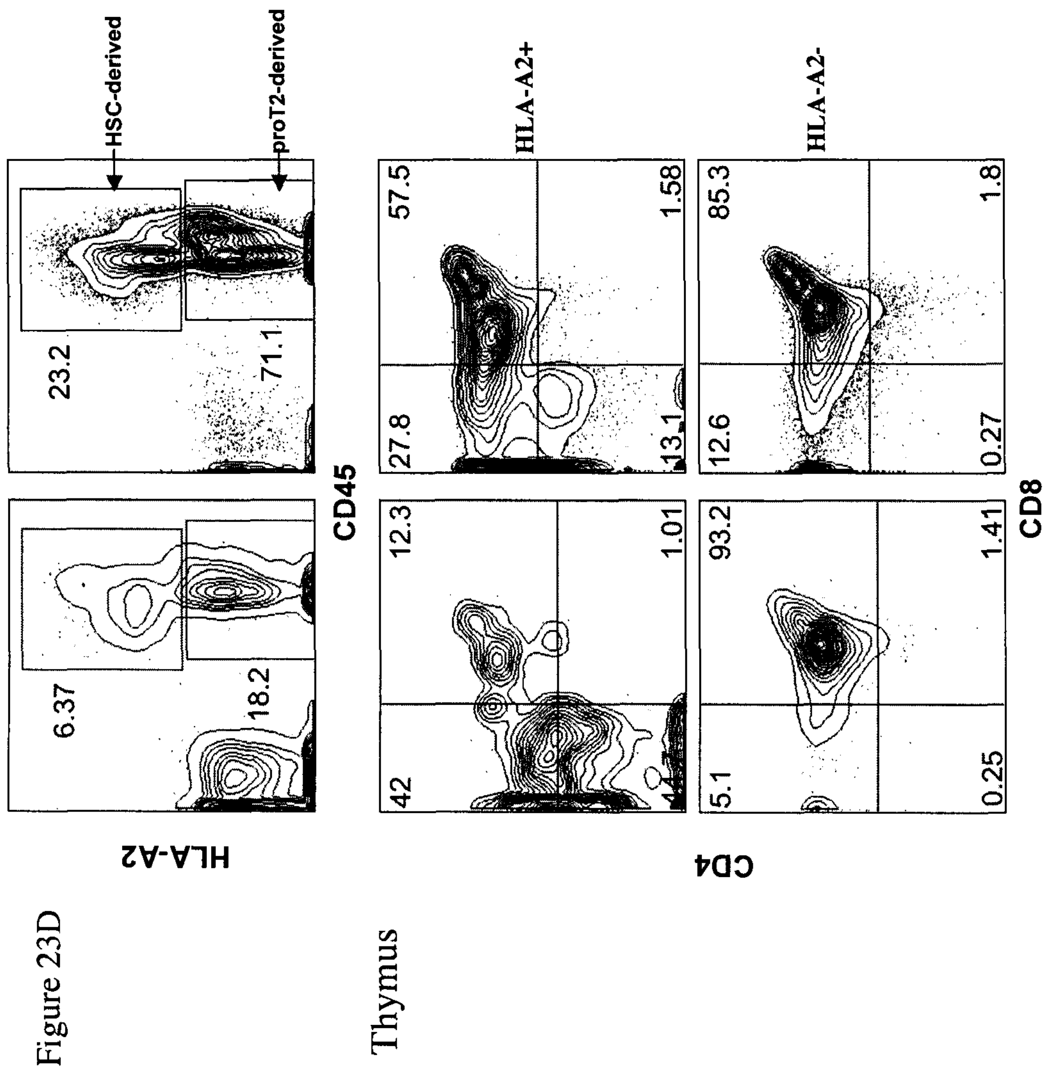

In Vitro-Generated pro-T2 Cells Coinjected with Human HSCs into Immunodeficient Mice Enhance HSC-Derived Thymopoiesis As shown in FIGS. 14 and 15, proT cells are capable of engrafting and reconstituting the thymuses of RAG2$^{-/-}\gamma_c^{-/}$ and NOD/SCID$\gamma_c^{-/}$ mice. Furthermore, the inventors noted that CD34+ HSCs displayed lower or negligible engraftment capacity, thus the inventors sought to determine whether the coinjection of in vitro generated proT2 cells with HSCs (derived from a different donor) could positively affect T-lineage reconstitution contributed by HSC-derived cells. To this end, human UCB $CD34^+CD38^{-/lo}$ (HLA-AZ) cells were differentiated on OP9-DL1 cells for 10-12 days, and $CD34^+CD7^{++}$ $CD5^+$ (proT2) cells were sorted by flow cytometry. $CD34^+$ $CD38^{-/lo}$ (HLA-A2$^+$) cells from umbilical cord-blood were also sorted. Irradiated (130 rads) neonatal NOD/SCID/$\gamma c^{null}$ mice from the same litter were divided into 3 groups and injected intrahepatically with $3.5\times10^4$ HSCs, $2.5\times10^5$ proT2 cells, or $3.5\times10^4$ HSCs mixed with $2.5\times10^5$ proT2 cells. At 6 weeks post-injection, the inventors looked for the presence of human cells in the BM (FIG. 23A) and were able to trace the origin of the donor cells based on HLA-A2 cell surface expression. The inventors observed the presence of human $CD45^+$HLA-A2$^+$ cells in the BM of mice injected with HSCs only, or receiving both HSCs plus proT2 cells. This population corresponded to cells that were generated from HSCs (HLA-A2+), as such, cells with this phenotype were not observed in mice injected with proT2 cells alone. Further gating on HSC-derived $CD45^+$HLA-A2$^+$ revealed that these cells belonged primarily to the B cell lineage ($CD19^+$) with a smaller proportion of these being myeloid lineage cells ($CD33^+$). Specifically, in the HSC injected mouse these lineages were 85% and 8.5%, respectively, with very similar percentages observed in both mice coinjected with HSCs and proT2 cells. FIG. 23B shows that human B and myeloid cells derived from HSCs could be found in the spleen. Of note, for both BM and spleen engraftment the inventors did not observe an enhancement or detriment to the HSC derived lineages when coinjected with proT2 cells; and little to no proT2-derived cells were found at these sites. In contrast, HSC-derived T-lymphopoiesis was drastically improved by coinjection with in vitro-generated proT2 cells. FIG. 23C shows cell surface staining for CD45 and HLA-A2, in which the HSC-only injected mouse showed an extremely low population of human cells in the thymus (as expected based on the results shown in FIG. 16). However, coinjected mice had a dramatic 300-1000 fold increase in the percentage of $CD45^+$HLA-A2$^+$ (HSC-derived) cells. Additionally, coinjected mice also possessed a large percentage of cells that corresponded to proT2-derived ($CD45^+$HLA-A2$^-$) cells (18% and 71%), and as expected, this population was not be observed in mice that received HSCs only. Further analysis of $CD45^+$HLA-A2$^+$ and $CD45^+$HLA-A2$^-$ cells in coinjected mice showed that HSC-derived cells contained less $CD3^{hi}$ cells (7% and 27%) as well as decreased percentages of $CD4^+CD8^+$ DP (12% and 58%) T cells as compared proT2-derived cells, which displayed increased CD3 expression and an increase in the percentage of DP T cells (over 85% in both mice) (FIG. 23D). The delay in their T-lineage differentiation kinetics by HSC-derived cells is consistent with their more immature and primitive status at time of injection, as compared to in vitro-generated proT2 cells.

Discussion

The early stages of human T-cell development have been broadly-defined by several investigators (Blom and Spits, 2006; Weerkamp et al., 2006c). Here, the inventors have taken advantage of a simple and powerful in vitro system to further refine this view by examining the differentiation of human UCB-HSCs cultured with OP9-DL1 cells, in which the early stages of T-cell development can be readily characterized. The temporal kinetic analysis of early and late time points allowed the inventors to discern an ordered pattern of developmental stages, which is highlighted by the sequential cell surface expression of CD34, CD45RA, CD7, CD5, CD1a, CD2, CD4, CD8, and CD3.

Although the OP9-DL1 system recapitulates the stages of human thymocyte differentiation, the inventors noted one difference regarding the expression of CD2, which has been reported to be expressed on some of the early $CD34^+$ thymocytes as well as in $CD34^+$ cells found in the bone marrow (Haynes and Heinly, 1995; Haynes et al., 1988; Terstappen et al., 1992). The inventors observed CD2 expression only at low levels on cells that were down-regulating CD34 expression, and high expression of CD2 was seen only at later developmental stages. One possibility for these differences could be an accumulation of $CD34^+$ cells with this early phenotype within the thymus or that the signals that normally induce the expression of CD2 on all thymocytes may be lacking in vitro.

Initial findings by the inventors' lab and others have clearly shown that UCB-$CD34^+$ cells can be induced to differentiate to the T-cell fate upon coculture with stromal cells ectopically-expressing Dll1 (Jaleco et al., 2001; La Motte-Mohs et al., 2005). However, several groups have demonstrated that the $CD34^+$ population is heterogeneous in regards to their self-renewal ability, engraftment and lineage potential (Byk et al., 2005; Guenechea et al., 2001; Kollet et al., 2001; Mazurier et al., 2004). With this in mind, the inventors examined whether specific $CD34^+$ subsets differed in their ability to serve as T-cell progenitors. Additionally, Hogan et al. suggested that the $CD34^+CD38^-$ pool contains a higher frequency of cells with T-cell potential, since NOD/SCID mice engrafted with this fraction showed greater thymus repopulation as compared to animals receiving $CD34^{+}CD38^{lo}$ or $CD38^{+/hi}$ cells (Hogan et al., 2002). In keeping with this, the inventors' results indicated that the $CD38^{+/hi}$ fraction has a significantly 5-fold lower T-cell potential than the more primitive $CD38^{-}$ or $CD38^{lo}$ subsets, which surprisingly showed similar T-progenitor frequencies. The comparable progenitor frequencies by these $CD34^{+}CD38^{-or\ lo}$ cells may be accounted for by a report suggesting that CD38 is reversibly expressed between negative and low levels (McKenzie et al., 2007).

The critical role of Notch signals for inducing T-lymphopoiesis is now well-established (Ciofani and Zuniga-Pflucker, 2007; Pear and Radtke, 2003). Here, the inventors identified the stages of T-cell development in which the induction of Notch target genes are first up-regulated. These stages corresponded to when $CD34^{+}$ cells begin to express CD7 at high levels, with some further induction following the loss of CD34 expression. The inventors' findings are supported by several studies demonstrating that UCB-$CD34^{+}$ CD7-expressing cells are strongly biased to the lymphoid lineage with very little myeloid potential (Haddad et al., 2004; Hao et al., 2001; Hoebeke et al., 2007). These observations are consistent with the notion that T-cell specification occurs early, within the first week, and therefore these Notch-induced $CD34^{+}CD7^{++}$ cells would likely show an increased T-progenitor frequency. Indeed, the inventors' results indicated that following Notch/Delta-like interactions, $CD34^{+}$ $CD7^{++}$ cells show a 2-fold higher T-progenitor frequency than the initial UCB-$CD34^{+}$CDT cells. These findings suggested that the HSC/OP9-DL1 cocultures readily support the generation of T-cell progenitors, which could be akin to thymus-colonizing cells.

Figure 9:
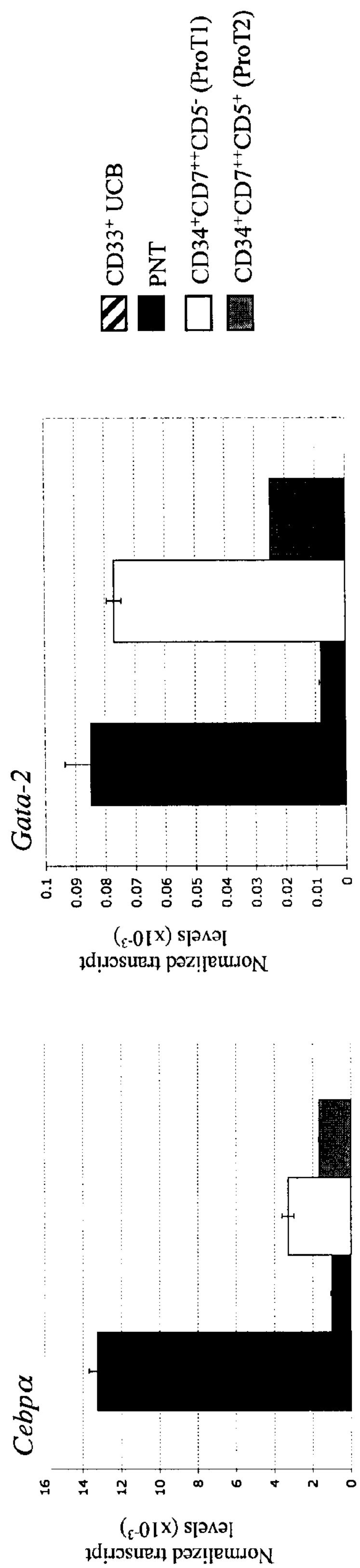
FIG. 9. Gene expression analysis of $CD34^+$ $CD7^{++}$ $CD5^-$ and $CD34^+$ $CD7^{++}$ $CD5^+$ subsets. Q-PCR analysis for the expression of Cebpα and Gata-2 from $CD34^+$ $CD7^{++}$ $CD5^-$ (proT1) and $CD34^+$ $CD7^{++}$ $CD5^+$ (proT2) cells sorted from a day 14 HSC/OP9-DL1 coculture. $Lin^-$ thymocytes obtained $^{from}$ human PNT or $CD33^+$ myeloid cells obtained from the $Lin^+$ fraction of UCB served as controls. Transcript levels for the indicated genes were normalized to human β-actin. These data are representative of 3 independent experiments, with the STD error bars shown corresponding to values obtained from triplicate wells within an individual experiment.

It is well-established that the thymus is continuously seeded with blood-borne progenitors, as the thymus-resident progenitors do not possess self-renewing potential (Donskoy and Goldschneider, 1992). A study by Haddad et al. (Haddad et al., 2006) proposed that thymus-colonizing cells express $CD34^{+}CD7^{++}CD45RA^{+}$. Cells with a similar phenotype are detected in HSC/OP9-DL1 cocultures, and here the inventors show that these cells were able to serve as thymus-colonizing cells. Additionally, the inventors noticed the presence of two distinct progenitor subsets within the $CD34^{+}CD7^{++}CD1a^{-}$ population, termed proT1 (CD5") and proT2 cells ($CD5^{+}$). Both subsets are capable of thymus reconstitution, however, when used in limiting dilution assays, the inventors observed dramatic differences in their ability to engraft a host thymus in vitro, with the more mature proT2 cells showing a 3-fold higher progenitor frequency than proT1 cells. In contrast, when assayed on OP9-DL1 cells both pro-T subsets exhibited statistically similar progenitor frequencies, which were also dramatically higher (200-600×) than those observed in FTOC. These findings suggest that human pro-T cells, which otherwise possess high T-cell potential, are affected by xenogeneic barriers present in the mouse FTOC system, which severely lowers their engraftment effectiveness. Additionally, the inventors noted that these pro-T subsets differed in the expression of CCR9, PSGL-1 and multiple integrins, which serve to provide a potential mechanism for the enhanced engrafting ability demonstrated by proT2 cells. The higher expression levels of these molecules by proT2 cells was specific, in that the transcript levels of Cebpα and Gata-2 were higher in the proT1 subset, which is consistent with their more immature status (FIG. 9).

The HSC/OP9-DL1 cocultures not only serve to characterize progenitor function or early events in human T-cell development, but may also provide a simple method for the generation of functional T-cells in vitro. This approach may be applicable to cell-based immunotherapies that presently capitalize on T-cell effector-function to induce/enhance anti-tumor eradicating immunity (Rosenberg et al., 2008). Indeed, the inventors now provide clear evidence for the maturation of functionally-responsive SP8s generated from HSC/OP9-DL1 cocultures. This raises the question of which cell-type, within the cultures, is mediating the MHC-dependent positive selection of SP8s. It is unlikely that the OP9 cells, which express mouse MHC class I that is not effectively recognized by human CD8 molecules (Irwin et al., 1989), would supply the required positive selection signals. Rather, a human MHC class I-expressing UCB-derived cell, which may or may not be a T-lineage cell, is likely to be the conveyor of these signals. Additionally, the inventors also noted the appearance of $CD3^{+}CD4^{+}$ T-cells (FIGS. 4A and 4B), which could be similarly selected by human MHC class II-expressing cells. However, in contrast to the SP8s, these cells do not show the hallmarks of functional mature T-cells (data not shown), and may represent transitional cells that require additional differentiation signals that are not readily available in these cultures.

Figure 10:
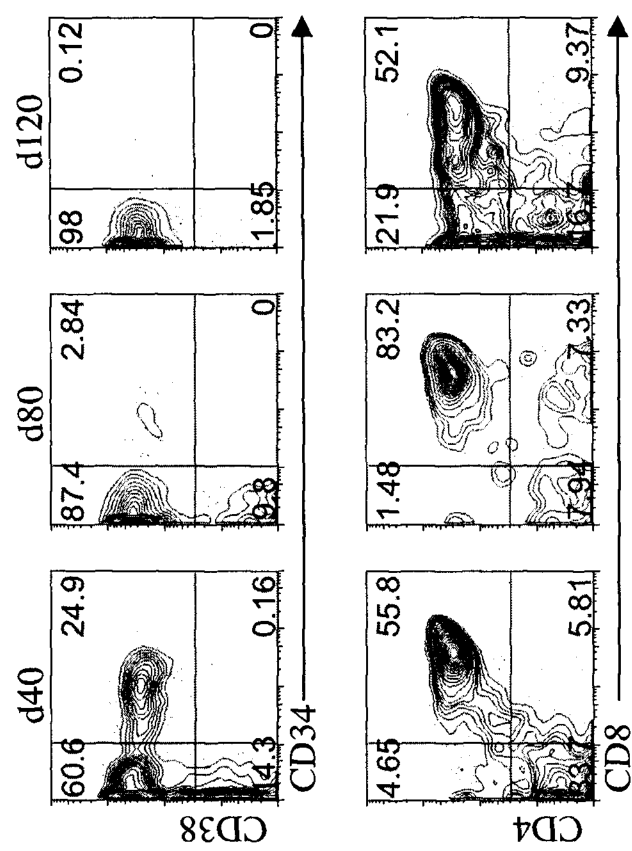
FIG. 10. Analysis of long-term HSC/OP9-DL1 cocultures. $CD34^+$ $CD38^{-/lo}$ cells cultured on OP9-DL1 cells for 40, 80 and 120 days were analyzed by flow cytometry for the expression of CD7, CD34, CD8 and CD4. These data are representative of at least 5 independent experiments.

Human HSC/OP9-DL1 cultures showed robust and continued expansion of DP cells, and could be observed in cultures lasting up to or beyond 4-months (FIG. 10). $CD4^{+}CD8^{+}$ DP cells are known to be short-lived (Shortman et al., 1990), and thus their presence at these late-time points implies that a progenitor cell is maintained and sustains this population. Of note, the inventors are able to detect a population of $CD34^{+}$ pro-T cells at these late-time points, but it is unclear whether these cells persist over time from an initial large pool of progenitors or from an ability to self-renew and expand in these cultures. One possible mechanism would involve Notch signals in the maintenance or extended self-renewal of a progenitor cell subset (Karanu et al., 2000; Karanu et al., 2001; Varnum-Finney et al., 1998), however this notion remains to be directly examined.

Our findings demonstrate that $CD34^{+}CD7^{++}$ T-progenitors expressing CD5 possess a higher progenitor potential in their ability to engraft FTOCs than their CD5-negative counterpart. The insight obtained from this analysis makes these $CD5^{+}$ proT2 cells an attractive subset for further studies to evaluate their immune reconstitution potential in mouse models (Legrand et al., 2006). Upon further analysis, bulk $CD34^{+}$ $CD7^{++}$ T-progenitors derived from human umbilical cord blood HSCs and generated in vitro utilizing the OP9-DL1 coculture system are capable of thymic reconstitution in two immunodeficient mouse models (FIG. 11-16). These thymocytes bear the hallmark signature of committed T-lineage cells through the expression of CD7, CD5, CD1a, CD4 and CD8 on their cell surface. Although the vast majority of human thymocytes at three weeks post intrahepatic injection of progenitor-T cells are CD4 CD8 double positive cells, a small percentage of CD4- and CD8-single positive cells can be detected amongst gated $CD45^{+}CD3^{hi}$ cells. These single positive cells have yet to appear in peripheral organs such as the spleen (data not shown), suggesting that positive and negative selection initiated by stromal elements within the mouse thymus and/or human antigen presenting cells derived from progenitor-T cells, have yet to occur and thus, premature for thymic export. The inventors' data also demonstrate that human CD34+ HSCs also exhibit thymic reconstitution following intrahepatic injection into immodeficient strains of mice and are consistent with previous reports by Gimeno et al. and Traggiai, et al (Gimeno et al., 2004; Traggiai et al., 2004). In the inventors' hands, thymic reconstitution potential from $CD34^+$HSCs appears less efficient and robust than from $CD34^+CD7^+$ bulk progenitor-T cells. Two and not necessarily mutually exclusive possibilities can be advanced to explain this observation. In one scenario, while sub-lethal irradiation is not required to condition the bone marrow of $RAG2^{-/-}\gamma_c^{-/-}$ two week neonates, to accept an HSC cell engraftment Gimeno, 2004 #1087}, it may facilitate bone marrow engraftment and the subsequent generation of thymic colonizing cells reported and detected by Haddad et al in the fetal liver and bone marrow of humans (Haddad et al., 2004; Haddad et al., 2006). It is therefore plausible that should such cells be generated by human HSC engraftment into immunodeficient mice, that these cells would colonize and differentiation into human T cell lineage cells within the host thymus. Alternatively, thymic colonizing cells might be present in limiting numbers within the heterogeneous populations sorted by a $CD34^+CD38^{-/lo}$ phenotype. In both scenarios, it is conceivably that human HSCs would exhibit delayed kinetics thymic reconstitution potential compared to human bulk progenitor-T cells.

It has been established that patients undergoing autologous or allogeneic hematopoietic stem cell transplants (HSCT) for the treatment of various hematological disorders display a profound defect in T cell recovery after HSCT. In contrast to the majority of hematopoietic cells whose levels are restored within weeks post transplant, T-lineage recovery is impaired in both cell number and function for up to 2 years or it may never recover (Fry and Mackall, 2005). This delay or absence results in impaired immune function and is associated with increased susceptibility to infection or relapse. Similar to the approach published by Van den Brink's group (Zakrzewski et al., 2006a) using mouse precursors, the inventors' results demonstrate that in vitro-generated human proT or proT2 cells dramatically improved HSC-derived T-lymphopoiesis, which in fact was not typically observed in mice receiving HSCs alone (FIG. 23). Furthermore the coinjection of in vitro-generated proT cells with HSCs did not affect HSC-derived myelopoiesis or B-lymphopoiesis indicating a targeted effect on the generation of T cells from HSCs. A potential mechanism for this effect may be due to the rapid restoration of the host thymic niches, involving cell cross talk between T-lineage to thymic stromal cells, resulting in improved stromal cell cellularity and function, such as cytokine and chemokine production that may then result in enhanced HSC-derived T-progenitor migration and recruitment from the bone marrow into the thymus. Another explanation, for the observed results may be a direct "piggy-back" of proT cells at the time of injection allowing HSCs to bypass the bone marrow and enter the thymus immediately by attaching to the proT cells.

Taken together, the inventors' data suggests that rapid immune reconstitution for the treatment of immunodeficiency may be facilitated though the utilization of progenitor T cells either in concert or in the absence of hematopoietic stem cell approaches. Such approaches can be tailored or genetically-engineered to generate large numbers of the progenitor T cells described herein and their progeny to treat immunodeficiency, triggered by cancer chemo/radio therapeutic regimens and HIV infection, or even restore proper immune function and regulation for the suppression of autoimmunity, Indeed, the use of in vitro-derived progenitor T-cells may prove therapeutically relevant over mature effector T-cells by avoiding issues such as graft versus host disease, as these cells would undergo positive and negative selection within the host thymus (Zakrzewski et al., 2006b). It is possible then to speculate that in vitro-generated T-progenitor cells may eventually serve as a viable option for cell-based therapies (La Motte-Mohs et al., 2007; Zakrzewski et al., 2008), as these cells can be generated in large numbers, allowing for novel strategies to be developed for the re-establishment of adaptive-immunity in immunocompromised individuals.

Example 9

Progenitor T Cells are Generated Following Coculture on OP9-DL4 Cells

Materials and Methods

Sorted human cord blood derived-HSCs were placed on OP9-control, OP9-DL1 or OP9-DL4 cells and cocultured for 24 or 40 days in presence of recombinant human cytokines Flt-3L (5 ng/ml) (R&D Systems, Minneapolis, Minn.) and IL-7 (5 ng/ml) (Peprotech, Rocky Hill, N.J.) as previously described. At day 24 of coculture, developing cells were stained in FACS Buffer (Hank's Balanced Salt Solution (HBSS) 1×—no phenol, no $Ca^{2+}$ no $Mg^{2+}$, bovine serum albumin (BSA) 1.0% and sodium azide 0.05%) with the following human antibodies: PE-CD4 [clone RPA-T4], FITC-CD8 [clone RPA-T8], PE-CD7 [clone M-T701], APC-CD1a [clone HI149], biotin-CD5 [clone UCHT2], FITC-TCR-αβ [T10B9.1A-31], FITC TCR-γδ [B1.1], APC-CD3 [UCHT2], PE-TCRvβ3 [JOVI-3], PE-TCRvβ5 [MH3-2], PE-TCRvβ8 [JR2], PE-TCRvβ12 [S511], PE-TCRvβ23 [AHUT7] (all purchased from BD-Pharmigen, San Jose, Calif.), and biotin-pre-Ta (a gift from Dr. Maria Louisa Toribio) against the appropriate isotype controls. After incubation, cells were washed and stained with either FITC-Streptavidin (SAv) and APC-SAv secondary reagents (also purchased from BD Pharmigen) for biotin-labeled cells primary antibodies. Following a second incubation and wash, cells were resuspended in FACS buffer containing propidium iodide (0.2 μg/ml) and were run on a FACSCalibur (BD-Biosciences) flow cytometer. Data analysis was performed using FlowJo software (Tree Star, Ashland, Oreg.) by gating on live lymphocytes and lack of propidium iodide uptake. GFP-expressing OP9 stromal cells were excluded through GFP expression and side scatter gating. This procedure eliminated 99% of contaminating GFP-expressing OP9 stromal cells. Numbers in quadrant corners represent percent of gated cells.

Results

As OP9-DL1 cells supported robust T cell development generating both progenitor T and double positive T cells (FIGS. 17, 18, and 20), the inventors undertook studies to determine whether OP9 cells transduced to express the stronger affinity ligand for the Notch1 receptor (Besseyrias et al., 2007), Delta-like-4 (OP9-DL4 cells) could also support the differentiation of umbilical cord blood-derived HSCs towards the T cell lineage.

As seen in FIG. 17, human HSCs cocultured on OP9-DL1 or OP9-DL4 cells, but not OP9-control cells, generated CD4 CD8 double positive T cells following 24 days of coculture. Specifically, double positive T cells accounted for between ~15-30% of the lymphocyte population when cocultured on OP9-DL4 or OP9-DL4 cells respectively and proceeded through the CD4-intermediate single positive stage (ISP). At this stage of T cell development, where double positive T cells are starting to emerge, pre-Tα expression (Carrasco et al., 2002), a key molecule involved in developing T cell survival and expansion, was also evident on CD4-positive cells and CD4-negative cells in OP9-DL1 and OP9-DL4 cocultures, but not OP9-control cocultures. As pre-Tα expression was observed on both CD4-positive and CD4-negative cells, the inventors undertook further studies to determine whether progenitor T cell populations that expressed (proT1) or lacked (proT2) CD5 could be evidenced. FIG. 18 shows that OP9-DL1 and OP9-DL4 cocultures, but not OP9-control cocultures, generate cells of the T lineage which can be broken down into three populations, $CD7^{+}CD1a^{++}$ (more mature T cells), $CD7^{++}CD1a^{+}$ (committed T cells), and $CD7^{++}CD1a^{-}$ (specified progenitor T cells). Consistent with its role as a T cell marker, CD5 is nearly ubiquitously expressed on the $CD7^{+}CD1a^{++}$ and $CD7^{++}CD1a^{+}$. In contrast, progenitor $CD7^{++}CD1a^{-}$ cells can be broken down into two populations by the absence or presence of CD5 expression, proT1 cells and proT2 cells respectively.

As both OP9-DL1 and OP9-DL4 cocultures generated progenitor T cells and their more differentiated progeny, the inventors then undertook studies to determine whether continued coculture would result in the emergence of T cells that expressed TCRαβ or TCRγδ. FIG. 19 shows that while $TCR\alpha\beta^{-}$ or $TCR\gamma\delta^{-}$ expressing cells can detected amongst the gated $CD7^{++}CD1a^{-}$ $CD7^{++}CD1a^{+}$, both TCR-bearing subsets are increased in the more mature $CD7^{+}CD1a^{+}$. In order to determine whether developing TCRαβ utilized different V-beta regions, developing T cells from OP9-control, OP9-DL1, and OP9-DL4 cocultures were stained against CD3 and several V-beta regions. As FIG. 20 illustrates, developing cells from OP9-DL1 cocultures and OP9-DL4 contained CD3-expressing cells (~38% and ~13%, respectively) compared to OP9-control cocultures, which lacked CD3-expressing cells. Furthermore, multiple V-beta usage was observed on CD3-expressing cells in OP9-DL1 cocultures, and to a lesser extent OP9-DL4 cocultures, compared to isotype controls. Specifically, of the V-betas that were examined by flow cytometric analysis, V 3 and V 5 expression was most readily detected. Taken together, these results show that OP9-DL4 cells behave similarly to OP9-DL1 cells in their capacity to generate progenitor T cell subsets: proT1 and proT1 cells, that can further undergo differentiation to give rise to more mature T cells.

Discussion:

The results showing that OP9-DL4 cells, like OP9-DL1 cells, can generate both progenitor T and more differentiated T cell progeny, supports the notion that additional Notch receptor ligands such as Delta-like-4 may offer additional signals that may further enhance or promote directed differentiation of human HSCs towards cells of the T cell lineage. Whether these Delta-like-4 signals are distinct and/or overlapping remains to be further elucidated and is thus far difficult to test experimentally due to the lack of commercially available, non-cross reacting, ligand specific-monoclonal antibodies. Recently, it has been demonstrated that Delta-like-4 is the favored ligand that binds with higher affinity to the Notch1 receptor suggesting that Delta-like-4 may be the ligand with the greatest capacity to induce T cell and support T cell development (Besseyrias et al., 2007). Interestingly, human T cell development induced by OP9-DL1 or OP9-DL4 cocultures seems to suggest that while OP9-DL4 support T cell development, by far OP9-DL1 cells seem superior in their capacity to induce and support robust human T cell development. It should be noted that in the inventors' coculture system, comparable level of Delta-like-expression is difficult to ascertain through reporter GFP-expression alone. Thus, given the over-expression of both Delta-like-1 and Delta-like-4 and their capacity to endocytosis (Bray, 2006), it becomes unclear whether the overall signal strength transduced to Notch receptor bearing differentiation cells, masks or exacerbates the differences observed upon supra-optimal expression found on Delta-like molecules within the OP9-DL1 or OP9-DL4 coculture system. To address this issue, the inventors have begun to engineer tagged versions of OP9-DL1 and OP9-DL4 cells to assess the expression of protein levels within these cells to determine whether distinct or similar signals are transmitted towards developing progenitor T cells. Nevertheless, it is clear from the inventors' studies that both OP9-DL1 and OP9-DL4 cells can support the robust and directed-differentiation of human umbilical cord blood-derived HSCs towards cells of the T lineage, generating large numbers of progenitor T cell subsets, proT1 and proT2 as well as their more differentiated progeny.

Example 10

Human Embryonic Stem Cells (hESCs) and Human Induced Pluripotent Stem Cells (hiPSCs) Differentiate into Early T-Lineage Cells when Cultured with OP9-DL1 or OP9-DL4 Cells Materials and Methods As previously described (Kennedy et al., 2007) human ESCs are aggregated to form embryoid bodies (EB) and then sequentially induced to differentiate towards the hematopoietic lineage through the sequential addition of exogenous cytokines. Briefly, during the EB formation, cytokines were added as follows: bone morphogenic protein 4 (BMP4) 10 ng/ml at day 0-4, basic fibroblastic growth factor (bFGF) 5 ng/ml at day 1-8, Activin A 0.3 ng/ml at day 2-4, vascular growth factor (VEGF) 15 ng/ml at day 4-8, dickkopf-1 (Dkk1) 50 ng/ml at day 4-6, interleukin 11 (IL-11) 5 ng/ml at day 6-8, IL-6 10 ng/ml at day 6-8, insulin-like growth factor IGF-1 25 ng/ml at day 6-8, stem cell factor (SCF) 100 ng/ml at day 6-11, thrompoietin (TPO) 50 ng/ml at day 8-11, IL-3 50 ng/ml at day 8-11, erythropoietin 4 units at day 8-11, Flt3-L 320 ng/ml at 8-11. Following 9-11 days of EB culture, sorted $CD34^{+}$ and $CD34^{-}$ cells were seeded onto OP9-DL1 cells (or OP9-DL4), cultured for 20 days, and assayed for T cell potential using flow cytometry. During the OP9-DL1 (or OP9-DL4) coculture period, media was changed twice a week, and cocultures were transferred onto new OP9-DL1 (or OP9-DL4) cells. Flt3-L 5 ng/ml, IL-7 5 ng/ml, were given during each media change. SCF 100 ng/ml was given only during the first 14 days of OP9-DL1 (or OP9-DL4) cocultures.

Human ESC and Human iPSC Differentiation into T-Lineage Cells

Although sustained and continuous T cell development can be derived in vitro from UCB-HSCs and can generate $CD4^{+}$ $CD8^{+}$ DP, $CD4^{+}$ SP and $CD8^{+}$ SP cells, human embryonic stem cells (hESCs) are an attractive source for generating progenitor T cells for future immune-reconstitution studies. Unlike HSCs obtained from other sources, hESCs can be maintained easily in their undifferentiated state, possess unlimited expansion potential, and are easily malleable for genetic modification. Thus far, the generation of T cells from hESCs has remained possible but inefficient relying on cumbersome methodology and poorly defined inductive events (Galic et al., 2006; Galic et al., 2009; Timmermans et al., 2009). This is due in large part to the poor understanding of how hESCs differentiate in vitro. Yet, hESCs can differentiate in culture to form all three germ layers (Itskovitz-Eldor et al., 2000; Schuldiner et al., 2000) and there has been limited success in inducing hESCs to develop into hematopoietic cells and B and NK cells (Kaufman et al., 2001; Woll et al., 2005). In particular, there has been only three reports showing that hESCs can yield T cells in vivo, two of which required the direct injection of human ESC-derived $CD34^{+}$ cells into conjoint human thymic/liver (Thy/Liv) tissues implanted under the kidney capsule of sublethally irradiated immunodeficient SCID-mice (Galic et al., 2006; Galic et al., 2009). The third report (published after the initial submission of the provisional patent application) although promising relied on morphological visualization of hematopoietic zones on OP9-control rather than the isolation of specific specific subsets based on cellular markers of differentiation, which then had to be excised and purified onto OP9-DL1 cells (Timmermans et al., 2009). Importantly, there are no reports to date regarding the generation of T lymphocytes from human ESCs entirely in vitro—underscoring the need to develop a simple and effective in vitro system for T cell development.

Results

Using the two-stage protocol method for the differentiation of hESCs (Kennedy et al., 2007), sorted $CD34^{++}$ cells, but not $CD34^-$ cells, could generate immature early cells of the T-lineage by 20 days of OP9-DL1 coculture, as evidence by the expression of CD7 and CD5 (FIG. 24A). Furthermore, the inventors have extended these findings to hiPSCs, also obtained from the Keller group, and as shown in FIG. 24B, using a similar protocol as above, hiPSCs were sorted for $CD34^{++}$ cells and then cultured for 22 days with OP9-DL4 cells. This coculture approach also gave rise to early T-lineage cells expressing CD7 and CD5, similar to the cell surface phenotype obtained from UCB-HSC/OP9-DL1 cocultures.

Discussion

The present example shows the ability to generate $CD7^+$ $CD5^+$ human T-lineage cells, which has not been previously demonstrated using a prospective isolation of hESC or hiPSC-derived $CD34^+$ progenitors. The inventors feel that the defined culture method of EB formation using a specific cocktail of cytokines followed by culture with OP9-DL1 or OP9-DL4 stromal cells that induce high Notch signaling within these cells allows for the efficient generation of human T-lineage cells from these primitive progenitors.

The ability to readily obtain large numbers of in vitro-generated T cell progenitors, which can be derived from defined sources of stem cells, whether from UCB-HSCs, hESCs, and hiPSCs, opens new opportunities for the treatment of T cell immunodeficiencies, acquired or genetic in origin.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE I

Progenitor frequency analysis of human hematopoietic stem cell subsets.

| HSC subset[a] | Progenitor Frequency$^{-1}$ [95% confidence limits][b] |
|---|---|
| $CD34^+$ $CD38^-$ | 4.76 [3.66-6.21] |
| $CD34^+$ $CD38^{lo}$ | 3.85 [2.94-5.06] |
| $CD34^+$ $CD38^{+/hi}$ | 19.30 [14.77-25.22] |

[a]$CD34^+$ $CD38^-$, $CD34^+$ $CD38^{lo}$, and $CD34^+$ $CD38^{+/hi}$ HSCs were placed in limiting numbers in wells of a 96-well/plate containing OP9-DL1 cells, and cultured for 11 days before harvesting for flow cytometric analysis.

[b]Individual wells were scored for the presence of T cells based on $CD45^+$ $CD7^{++}$ staining. Statistical analysis was performed via the method of maximum likelihood applied to the Poisson Model (Fazekas de St, 1982).

TABLE II

Progenitor frequency analysis of progenitor T-cell subsets.

| Pro-T subset[a] | Culture System[b] | Progenitor Frequency$^{-1}$ [95% confidence limits][c] |
|---|---|---|
| ProT1 - $CD34^+$ $7^+$ $5^-$ | FTOC | 1384.72 [979-1959] |
| ProT2 - $CD34^+$ $7^+$ $5^+$ | FTOC | 411.74 [256-663] |
| ProT1 - $CD34^+$ $7^+$ $5^-$ | OP9-DL1 | 2.52 [1.75-3.63] |
| ProT2 - $CD34^+$ $7^+$ $5^+$ | OP9-DL1 | 1.95 [1.35-2.80] |

[a]$CD34^+$ $CD38^{-/lo}$ UCB-derived cells were cultured on OP9-DL1 cells for 12-14 days and proT1/proT2 cells, with the indicated phenotypes, were obtained by flow cytometric cell sorting.

[b]Pro-T subsets were placed in limiting numbers in FTOC or in wells of a 96-well/plate containing OP9-DL1 cells and cultured for 7 days before harvesting for flow cytometric analysis.

[c]Individual lobes or wells were scored for the presence of T cells based on $CD45^+$ $CD7^{++}$ or $CD7^{++}$ $CD1a^{-/+}$ staining, respectively. Statistical analysis was performed via the method of maximum likelihood applied to the Poisson Model (Fazekas de St, 1982).

TABLE III

Assessment of erythroid, myeloid, megakaryocytic and granulocytic potential of CD34+ UCB cells and various OP9-DL1 coculture-derived subsets.

| 500 cells plated | CFU-Mix Average colony number (n = 2) | BFU-E Average colony number (n = 2) | CFU-GM Average colony number (n = 2) | CFU-G Average colony number (n = 2) | CFU-M Average colony number (n = 2) |
|---|---|---|---|---|---|
| $CD34^+$ CB (control) | 7.5 | 66.5 | 10.5 | 15 | 2 |
| $CD34^+CD7^+CD5^-CD1a^-$ proT1 | 0 | 11.5 | 4 | 6.5 | 5 |
| $CD34^+CD7^+CD5^+CD1a^-$ proT2 | 0 | 0.5 | 4 | 5.5 | 17 |
| $CD34^-CD7^+$ coculture-derived | 0 | 0 | 0 | 0 | 0 |

The presence of clonogenic myelo-erythroid progenitors (BFU-E), granulocyte-macrophage colony forming units (CFU-GM), granulocyte colony forming units (CFU-G), macrophage forming units (CFU-M) and macrophage-megakaryocyte, erythroid, macrophage, granulocyte (CFU-mix) potential was evaluated by plating 500 sorted in vitro-derived cells (proT1, proT2, and $CD34^-$ $CD7^+$ subsets) into semi-solid media (1% methylcellulose). $CD34^+$ cells sorted from UCB servedas a positive control. Colonies were counted from duplicate cultures and the average number of colonies is shown after 22 days.

n, the number experimental replicates analyzed.

TABLE IV

Engraftment potential of proT1 and proT2 subsets injected into immunodeficient neonatal mice.

| Cell number injected | Subset | % of mice engrafted |
|---|---|---|
| $1 \times 10^4$ | ProT1 | 16% (n = 6) |
| | ProT2 | 50% (n = 2) |
| $2.5 \times 10^4$ | ProT1 | 14% (n = 7) |
| | ProT2 | 38% (n = 8) |

ProT1 and proT2 cells were sorted from a day 10 coculture and injected at the indicated cell numbers into immunodeficient mice. Thymuses were harvested 21-25 days post injection and engraftment was determined by the presence of human $CD45^+$ $CD7^{++}$ cells. The percentage of engrafted mice is shown.
n, the number of mice analyzed for each treatment group.

FULL CITATIONS FOR REFERENCES REFERRED TO IN THE SPECIFICATION

Adolfsson, J., Mansson, R., Buza-Vidas, N., Hultquist, A., Liuba, K., Jensen, C. T., Bryder, D., Yang, L., Borge, O. J., Thoren, L. A., et al. (2005). Identification of Flt3+ lympho-myeloid stem cells lacking erythro-megakaryocytic potential a revised road map for adult blood lineage commitment. Cell 121, 295-306.

Alderuccio, F., Murphy, K., and Toh, B. H. (2003). Stem cells engineered to express self-antigen to treat autoimmunity. Trends Immunol 24, 176-180.

Allman, D., Punt, J. A., Izon, D. J., Aster, J. C., and Pear, W. S. (2002). An invitation to T and more: notch signaling in lymphopoiesis. Cell 109 Suppl, S1-11.

Anderson, G., Pongracz, J., Parnell, S., and Jenkinson, E. J. (2001). Notch ligand-bearing thymic epithelial cells initiate and sustain Notch signaling in thymocytes independently of T cell receptor signaling. Eur J Immunol 31, 3349-3354.

Anderson, M. S., Venanzi, E. S., Klein, L., Chen, Z., Berzins, S. P., Turley, S. J., von Boehmer, H., Bronson, R., Dierich, A., Benoist, C., et al. (2002). Projection of an immunological self shadow within the thymus by the aire protein. Science 298, 1395-1401.

Apostolou, I., Sarukhan, A., Klein, L., and von Boehmer, H. (2002). Origin of regulatory T cells with known specificity for antigen. Nat Immunol 3, 756-763.

Apostolou, I., and von Boehmer, H. (2004). In vivo instruction of suppressor commitment in naive T cells. J Exp Med 199, 1401-1408.

Arroyo, A. G., Yang, J. T., Rayburn, H., and Hynes, R. O. (1996). Differential requirements for alpha4 integrins during fetal and adult hematopoiesis. Cell 85, 997-1008.

Awong, G., Motte-Mohs, R. N., and Zúñiga-Pflücker, J. C. (2008). In vitro human T cell development directed by notch-ligand interactions. Methods Mol Biol 430, 135-142.

Bárcena, A., Muench, M. O., Roncarolo, M. G., and Spits, H. (1995). Tracing the expression of CD7 and other antigens during T- and myeloid-cell differentiation in the human fetal liver and thymus. Leuk Lymphoma 17, 1-11.

Barker, J. N., and Wagner, J. E. (2003). Umbilical-cord blood transplantation for the treatment of cancer. Nat Rev Cancer 3, 526-532.

Baxter, A. G., and Cooke, A. (1993). Complement lytic activity has no role in the pathogenesis of autoimmune diabetes in NOD mice. Diabetes 42, 1574-1578.

Belghith, M., Bluestone, J. A., Barriot, S., Megret, J., Bach, J. F., and Chatenoud, L. (2003). TGF-beta-dependent mechanisms mediate restoration of self-tolerance induced by antibodies to CD3 in overt autoimmune diabetes. Nat Med 9, 1202-1208.

Bennaceur-Griscelli, A., Pondarre, C., Schiavon, V., Vainchenker, W., and Coulombel, L. (2001). Stromal cells retard the differentiation of CD34(+)CD38(low/neg) human primitive progenitors exposed to cytokines independent of their mitotic history. Blood 97, 435-441.

Benz, C., and Bleul, C. C. (2005). A multipotent precursor in the thymus maps to the branching point of the T versus B lineage decision. J Exp Med 202, 21-31.

Besseyrias, V., Fiorini, E., Strobl, L. J., Zimber-Strobl, U., Dumortier, A., Koch, U., Arcangeli, M.-L., Ezine, S., MacDonald, H. R., and Radtke, F. (2007). Hierarchy of Notch-Delta interactions promoting T cell lineage commitment and maturation. J Exp Med 204, 331-343.

Blom, B., Res, P., Noteboom, E., Weijer, K., and Spits, H. (1997). Prethymic CD34+ progenitors capable of developing into T cells are not committed to the T cell lineage. J Immunol 158, 3571-3577.

Blom, B., and Spits, H. (2006). Development of human lymphoid cells. Annu Rev Immunol 24, 287-320.

Blom, B., Verschuren, M. C., Heemskerk, M. H., Bakker, A. Q., van Gastel-Mol, E. J., Wolvers-Tettero, I. L., van Dongen, J. J., and Spits, H. (1999). TCR gene rearrangements and expression of the pre-T cell receptor complex during human T-cell differentiation. Blood 93, 3033-3043.

Bluestone, J. A. (2005). Regulatory T-cell therapy: is it ready for the clinic? Nat Rev Immunol 5, 343-349.

Bluestone, J. A., and Abbas, A. K. (2003). Natural versus adaptive regulatory T cells. Nat Rev Immunol 3, 253-257.

Bosma, G. C., Custer, R. P., and Bosma, M. J. (1983). A severe combined immunodeficiency mutation in the mouse. Nature 301, 527-530.

Brandes, M., Willimann, K., and Moser, B. (2005). Professional antigen-presentation function by human gammadelta T Cells. Science 309, 264-268.

Bray, S. J. (2006). Notch signalling: a simple pathway becomes complex. Nat Rev Mol Cell Biol 7, 678-689.

Byk, T., Kahn, J., Kollet, O., Petit, I., Samira, S., Shivtiel, S., Ben-Hur, H., Peled, A., Piacibello, W., and Lapidot, T. (2005). Cycling G1 CD34+/CD38+ cells potentiate the motility and engraftment of quiescent G0 CD34+/CD38−/low severe combined immunodeficiency repopulating cells. Stem Cells 23, 561-574.

Carrasco, Y. R., Navarro, M. N., de Yebenes, V. G., Ramiro, A. R., and Toribio, M. L. (2002). Regulation of surface expression of the human pre-T cell receptor complex. Semin Immunol 14, 325-334.

Case, S. S., Price, M. A., Jordan, C. T., Yu, X. J., Wang, L., Bauer, G., Haas, D. L., Xu, D., Stripecke, R., Naldini, L., et al. (1999). Stable transduction of quiescent CD34(+)CD38(−) human hematopoietic cells by HIV-1-based lentiviral vectors. Proc Natl Acad Sci USA 96, 2988-2993.

Cerdan, C., Rouleau, A., and Bhatia, M. (2004). VEGF-A165 augments erythropoietic development from human embryonic stem cells. Blood 103, 2504-2512.

Chadwick, K., Wang, L., Li, L., Menendez, P., Murdoch, B., Rouleau, A., and Bhatia, M. (2003). Cytokines and BMP-4 promote hematopoietic differentiation of human embryonic stem cells. Blood 102, 906-915.

Chatenoud, L., Salomon, B., and Bluestone, J. A. (2001). Suppressor T cells—they're back and critical for regulation of autoimmunity! Immunol Rev 182, 149-163.

Cho, S. K., Webber, T. D., Carlyle, J. R., Nakano, T., Lewis, S. M., and Zúñiga-Pflücker J. C. (1999). Functional characterization of B lymphocytes generated in vitro from embryonic stem cells. Proc Natl Acad Sci USA 96, 9797-9802.

Choi, E. Y., Jung, K. C., Park, H. J., Chung, D. H., Song, J. S., Yang, S. D., Simpson, E., and Park, S. H. (2005). Thymocyte-thymocyte interaction for efficient positive selection and maturation of CD4 T cells. Immunity 23, 387-396.

Ciofani, M., Knowles, G. C., Wiest, D. L., von Boehmer, H., and Zúñiga-Pflücker, J. C. (2006). Stage-specific and differential notch dependency at the alphabeta and gammadelta T lineage bifurcation. Immunity 25, 105-116.

Ciofani, M., Schmitt, T. M., Ciofani, A., Michie, A. M., Cuburu, N., Aublin, A., Maryanski, J. L., and Zúñiga-Pflücker, J. C. (2004). Obligatory role for cooperative signaling by pre-TCR and Notch during thymocyte differentiation. J Immunol 172, 5230-5239.

Ciofani, M., and Zuniga-Pflucker, J. C. (2007). The thymus as an inductive site for T lymphopoiesis. Annu Rev Cell Dev Biol 23, 463-493.

Ciofani, M., and Zúñiga-Pflücker, J. C. (2005). Notch promotes survival of pre-T cells at the beta-selection checkpoint by regulating cellular metabolism. Nat Immunol 6, 881-888.

Clark, R. A., Yamanaka, K., Bai, M., Dowgiert, R., and Kupper, T. S. (2005). Human skin cells support thymus-independent T cell development. J Clin Invest 115, 3239-3249.

Dahl, R., Walsh, J. C., Lancki, D., Laslo, P., Iyer, S. R., Singh, H., and Simon, M. C. (2003). Regulation of macrophage and neutrophil cell fates by the PU.1:C/EBPalpha ratio and granulocyte colony-stimulating factor. Nat Immunol 4, 1029-1036.

De Smedt, M., Hoebeke, I., and Plum, J. (2004). Human bone marrow CD34+ progenitor cells mature to T cells on OP9-DL1 stromal cell line without thymus microenvironment. Blood Cells Mol Dis 33, 227-232.

De Smedt, M., Reynvoet, K., Kerre, T., Taghon, T., Verhasselt, B., Vandekerckhove, B., Leclercq, G., and Plum, J. (2002). Active form of Notch imposes T cell fate in human progenitor cells. J Immunol 169, 3021-3029.

de Wynter, E. A., Emmerson, A. J., and Testa, N. G. (1999). Properties of peripheral blood and cord blood stem cells. Baillieres Best Pract Res Clin Haematol 12, 1-17.

Deftos, M. L., and Bevan, M. J. (2000). Notch signaling in T cell development. Curr Opin Immunol 12, 166-172.

Deftos, M. L., Huang, E., Ojala, E. W., Forbush, K. A., and Bevan, M. J. (2000). Notch1 signaling promotes the maturation of CD4 and CD8 SP thymocytes. Immunity 13, 73-84.

Dik, W. A., Pike-Overzet, K., Weerkamp, F., de Ridder, D., de Haas, E. F., Baert, M. R., van der Spek, P., Koster, E. E., Reinders, M. J., van Dongen, J. J., et al. (2005). New insights on human T cell development by quantitative T cell receptor gene rearrangement studies and gene expression profiling. J Exp Med 201, 1715-1723.

Donskoy, E., and Goldschneider, I. (1992). Thymocytopoiesis is maintained by blood-borne precursors throughout postnatal life. A study in parabiotic mice. J Immunol 148, 1604-1612.

Ehrenstein, M. R., Evans, J. G., Singh, A., Moore, S., Warnes, G., Isenberg, D. A., and Mauri, C. (2004). Compromised function of regulatory T cells in rheumatoid arthritis and reversal by anti-TNFalpha therapy. J Exp Med 200, 277-285.

Ellisen, L. W., Bird, J., West, D. C., Soreng, A. L., Reynolds, T. C., Smith, S. D., and Sklar, J. (1991). TAN-1, the human homolog of the Drosophila notch gene, is broken by chromosomal translocations in T lymphoblastic neoplasms. Cell 66, 649-661.

Fazekas de St, G. (1982). The evaluation of limiting dilution assays. J Immunol Methods 49, R11-23.

Ferrando, A. A., Neuberg, D. S., Staunton, J., Loh, M. L., Huard, C., Raimondi, S. C., Behm, F. G., Pui, C. H., Downing, J. R., Gilliland, D. G., et al. (2002). Gene expression signatures define novel oncogenic pathways in T cell acute lymphoblastic leukemia. Cancer Cell 1, 75-87.

Fisher, A. G., Larsson, L., Goff, L. K., Restall, D. E., Happerfield, L., and Merkenschlager, M. (1990). Human thymocyte development in mouse organ cultures. Int Immunol 2, 571-578.

Fleming, H. E., and Scadden, D. T. (2006). Embryonic stem cells make human T cells. Proc Natl Acad Sci USA 103, 12213-12214.

Fontenot, J. D., Gavin, M. A., and Rudensky, A. Y. (2003). Foxp3 programs the development and function of CD4+ CD25+ regulatory T cells. Nat Immunol 4, 330-336.

Fry, T. J., and Mackall, C. L. (2005). Immune reconstitution following hematopoietic progenitor cell transplantation: challenges for the future. Bone Marrow Transplant 35 *Suppl* 1, S53-57.

Galic, Z., Kitchen, S. G., Kacena, A., Subramanian, A., Burke, B., Cortado, R., and Zack, J. A. (2006). T lineage differentiation from human embryonic stem cells. Proc Natl Acad Sci USA 103, 11742-11747.

Galic, Z., Kitchen, S. G., Subramanian, A., Bristol, G., Marsden, M. D., Balamurugan, A., Kacena, A., Yang, O., and Zack, J. A. (2009). Generation of T lineage cells from human embryonic stem cells in a feeder free system. Stem Cells 27, 100-107.

Galy, A., Verma, S., Barcena, A., and Spits, H. (1993). Precursors of CD3+CD4+CD8+ cells in the human thymus are defined by expression of CD34. Delineation of early events in human thymic development. J Exp Med 178, 391-401.

García-Peydró, M., de Yébenes, V. G., and Toribio, M. L. (2003). Sustained Notch1 signaling instructs the earliest human intrathymic precursors to adopt a gammadelta T-cell fate in fetal thymus organ culture. Blood 102, 2444-2451.

Gimeno, R., Weijer, K., Voordouw, A., Uittenbogaart, C. H., Legrand, N., Alves, N. L., Wijnands, E., Blom, B., and Spits, H. (2004). Monitoring the effect of gene silencing by RNA-interference in human CD34+ cells injected into newborn RAG2−/− gamma common−/− mice:Functional inactivation of p53 in developing T cells. Blood.

Gluckman, E., Rocha, V., Boyer-Chammard, A., Locatelli, F., Arcese, W., Pasquini, R., Ortega, J., Souillet, G., Ferreira, E., Laporte, J. P., et al. (1997). Outcome of cord-blood transplantation from related and unrelated donors. Eurocord Transplant Group and the European Blood and Marrow Transplantation Group. N Engl J Med 337, 373-381.

Goldman, J. P., Blundell, M. P., Lopes, L., Kinnon, C., Di Santo, J. P., and Thrasher, A. J. (1998). Enhanced human cell engraftment in mice deficient in RAG2 and the common cytokine receptor gamma chain. Br J Haematol 103, 335-342.

Goldschneider, I. (2006). Cyclical mobilization and gated importation of thymocyte progenitors in the adult mouse: evidence for a thymus-bone marrow feedback loop. Immunol Rev 209, 58-75.

Gregori, S., Bacchetta, R., Hauben, E., Battaglia, M., and Roncarolo, M. G. (2005). Regulatory T cells: prospective for clinical application in hematopoietic stem cell transplantation. Curr Opin Hematol 12, 451-456.

Greiner, D. L., Hesselton, R. A., and Shultz, L. D. (1998). SCID mouse models of human stem cell engraftment. Stem Cells 16, 166-177.

Grossman, Z., Meier-Schellersheim, M., Paul, W. E., and Picker, L. J. (2006). Pathogenesis of HIV infection: what the virus spares is as important as what it destroys. Nat Med 12, 289-295.

Grünweller, A., Wyszko, E., Bieber, B., Jahnel, R., Erdmann, V. A., and Kurreck, J. (2003). Comparison of different antisense strategies in mammalian cells using locked nucleic acids, 2'-O-methyl RNA, phosphorothioates and small interfering RNA. Nucleic Acids Res 31, 3185-3193.

Guenechea, G., Gan, O. I., Dorrell, C., and Dick, J. E. (2001). Distinct classes of human stem cells that differ in proliferative and self-renewal potential. Nat Immunol 2, 75-82.

Gutiérrez-Frías, C., Sacedón, R., Hernández-López, C., Cejalvo, T., Crompton, T., Zapata, A. G., Varas, A., and Vicente, A. (2004). Sonic hedgehog regulates early human thymocyte differentiation by counteracting the IL-7-induced development of CD34+ precursor cells. J Immunol 173, 5046-5053.

Haas, D. L., Case, S. S., Crooks, G. M., and Kohn, D. B. (2000). Critical factors influencing stable transduction of human CD34(+) cells with HIV-1-derived lentiviral vectors. Mol Ther 2, 71-80.

Haddad, R., Guardiola, P., Izac, B., Thibault, C., Radich, J., Delezoide, A. L., Baillou, C., Lemoine, F. M., Gluckman, J. C., Pflumio, F., et al. (2004). Molecular characterization of early human T/NK and B-lymphoid progenitor cells in umbilical cord blood. Blood 104, 3918-3926.

Haddad, R., Guimiot, F., Six, E., Jourquin, F., Setterblad, N., Kahn, E., Yagello, M., Schiffer, C., Andre-Schmutz, I., Cavazzana-Calvo, M., et al. (2006). Dynamics of thymus-colonizing cells during human development. Immunity 24, 217-230.

Hamann, D., Baars, P. A., Rep, M. H., Hooibrink, B., Kerkhof-Garde, S. R., Klein, M. R., and van Lier, R. A. (1997). Phenotypic and functional separation of memory and effector human CD8+ T cells. J Exp Med 186, 1407-1418.

Hao, Q. L., Zhu, J., Price, M. A., Payne, K. J., Barsky, L. W., and Crooks, G. M. (2001). Identification of a novel, human multilymphoid progenitor in cord blood. Blood 97, 3683-3690.

Haynes, B. F., and Heinly, C. S. (1995). Early human T cell development: analysis of the human thymus at the time of initial entry of hematopoietic stem cells into the fetal thymic microenvironment. J Exp Med 181, 1445-1458.

Haynes, B. F., Martin, M. E., Kay, H. H., and Kurtzberg, J. (1988). Early events in human T cell ontogeny. Phenotypic characterization and immunohistologic localization of T cell precursors in early human fetal tissues. J Exp Med 168, 1061-1080.

Hirsch, E., Iglesias, A., Potocnik, A. J., Hartmann, U., and Fassler, R. (1996). Impaired migration but not differentiation of haematopoietic stem cells in the absence of beta1 integrins. Nature 380, 171-175.

Hoebeke, I., De Smedt, M., Stolz, F., Pike-Overzet, K., Staal, F. J., Plum, J., and Leclercq, G. (2007). T-, B- and NK-lymphoid, but not myeloid cells arise from human CD34 (+)CD38(−)CD7(+) common lymphoid progenitors expressing lymphoid-specific genes. Leukemia 21, 311-319.

Hoffmann, P., and Edinger, M. (2006). CD4+CD25+ regulatory T cells and graft-versus-host disease. Semin Hematol 43, 62-69.

Hogan, C. J., Shpall, E. J., and Keller, G. (2002). Differential long-term and multilineage engraftment potential from subfractions of human CD34+ cord blood cells transplanted into NOD/SCID mice. Proc Natl Acad Sci USA 99, 413-418.

Hogan, C. J., Shpall, E. J., McNulty, O., McNiece, I., Dick, J. E., Shultz, L. D., and Keller, G. (1997). Engraftment and development of human CD34(+)-enriched cells from umbilical cord blood in NOD/LtSz-scid/scid mice. Blood 90, 85-96.

Holling, T. M., van der Stoep, N., Quinten, E., and van den Elsen, P. J. (2002). Activated human T cells accomplish MHC class II expression through T cell-specific occupation of class II transactivator promoter III. J Immunol 168, 763-770.

Hori, S., Nomura, T., and Sakaguchi, S. (2003). Control of regulatory T cell development by the transcription factor Foxp3. Science 299, 1057-1061.

Ikawa, T., Kawamoto, H., Fujimoto, S., and Katsura, Y. (1999). Commitment of common T/Natural killer (NK) progenitors to unipotent T and NK progenitors in the murine fetal thymus revealed by a single progenitor assay. J Exp Med 190, 1617-1626.

Irwin, M. J., Heath, W. R., and Sherman, L. A. (1989). Species-restricted interactions between CD8 and the alpha 3 domain of class I influence the magnitude of the xenogeneic response. J Exp Med 170, 1091-1101.

Ito, M., Hiramatsu, H., Kobayashi, K., Suzue, K., Kawahata, M., Hioki, K., Ueyama, Y., Koyanagi, Y., Sugamura, K., Tsuji, K., et al. (2002). NOD/SCID/gamma(c)(null) mouse: an excellent recipient mouse model for engraftment of human cells. Blood 100, 3175-3182.

Itskovitz-Eldor, J., Schuldiner, M., Karsenti, D., Eden, A., Yanuka, O., Amit, M., Soreq, H., and Benvenisty, N. (2000). Differentiation of human embryonic stem cells into embryoid bodies compromising the three embryonic germ layers. Mol Med 6, 88-95.

Izon, D. J., Punt, J. A., and Pear, W. S. (2002). Deciphering the role of Notch signaling in lymphopoiesis. Curr Opin Immunol 14, 192-199.

Izon, D. J., Punt, J. A., Xu, L., Karnell, F. G., Allman, D., Myung, P. S., Boerth, N. J., Pui, J. C., Koretzky, G. A., and Pear, W. S. (2001). Notch1 regulates maturation of CD4+ and CD8+ thymocytes by modulating TCR signal strength. Immunity 14, 253-264.

Jaleco, A. C., Neves, H., Hooijberg, E., Gameiro, P., Clode, N., Haury, M., Henrique, D., and Parreira, L. (2001). Differential effects of Notch ligands Delta-1 and Jagged-1 in human lymphoid differentiation. J Exp Med 194, 991-1002.

Jenkinson, E. J., and Anderson, G. (1994). Fetal thymic organ cultures. Curr Opin Immunol 6, 293-297.

Jiang, R., Lan, Y., Chapman, H. D., Shawber, C., Norton, C. R., Serreze, D. V., Weinmaster, G., and Gridley, T. (1998). Defects in limb, craniofacial, and thymic development in Jagged2 mutant mice. Genes Dev 12, 1046-1057.

Jones, P., May, G., Healy, L., Brown, J., Hoyne, G., Delassus, S., and Enver, T. (1998). Stromal expression of Jagged 1 promotes colony formation by fetal hematopoietic progenitor cells. Blood 92, 1505-1511.

Jordan, M. S., Boesteanu, A., Reed, A. J., Petrone, A. L., Holenbeck, A. E., Lerman, M. A., Naji, A., and Caton, A. J. (2001). Thymic selection of CD4+CD25+ regulatory T cells induced by an agonist self-peptide. Nat Immunol 2, 301-306.

Karanu, F. N., Murdoch, B., Gallacher, L., Wu, D. M., Koremoto, M., Sakano, S., and Bhatia, M. (2000). The notch ligand jagged-1 represents a novel growth factor of human hematopoietic stem cells. J Exp Med 192, 1365-1372.

Karanu, F. N., Murdoch, B., Miyabayashi, T., Ohno, M., Koremoto, M., Gallacher, L., Wu, D., Itoh, A., Sakano, S., and Bhatia, M. (2001). Human homologues of Delta-1 and Delta-4 function as mitogenic regulators of primitive human hematopoietic cells. Blood 97, 1960-1967.

Kaufman, D. S., Hanson, E. T., Lewis, R. L., Auerbach, R., and Thomson, J. A. (2001). Hematopoietic colony-forming cells derived from human embryonic stem cells. Proc Natl Acad Sci USA 98, 10716-10721.

Kawamoto, H., Ohmura, K., and Katsura, Y. (1997). Direct evidence for the commitment of hematopoietic stem cells to T, B and myeloid lineages in murine fetal liver. Int Immunol 9, 1011-1019.

Kennedy, M., D'Souza, S. L., Lynch-Kattman, M., Schwantz, S., and Keller, G. (2007). Development of the hemangioblast defines the onset of hematopoiesis in human ES cell differentiation cultures. Blood 109, 2679-2687.

Kerre, T. C., De Smet, G., De Smedt, M., Zippelius, A., Pittet, M. J., Langerak, A. W., De Bosscher, J., Offner, F., Vandekerckhove, B., and Plum, J. (2002). Adapted NOD/SCID model supports development of phenotypically and functionally mature T cells from human umbilical cord blood CD34(+) cells. Blood 99, 1620-1626.

Kim, S., La Motte-Mohs, R. N., Rudolph, D., Zúñiga-Pflücker, J. C., and Mak, T. W. (2003). The role of nuclear factor-kappaB essential modulator (NEMO) in B cell development and survival. Proc Natl Acad Sci USA 100, 1203-1208.

Klug, C. A., Cheshier, S., and Weissman, I. L. (2000). Inactivation of a GFP retrovirus occurs at multiple levels in long-term repopulating stem cells and their differentiated progeny. Blood 96, 894-901.

Ko, H. S., Fu, S. M., Winchester, R. J., Yu, D. T., and Kunkel, H. G. (1979). Ia determinants on stimulated human T lymphocytes. Occurrence on mitogen- and antigen-activated T cells. J Exp Med 150, 246-255.

Kodama, H., Nose, M., Niida, S., and Nishikawa, S. (1994). Involvement of the c-kit receptor in the adhesion of hematopoietic stem cells to stromal cells. Exp Hematol 22, 979-984.

Kollet, O., Peled, A., Byk, T., Ben-Hur, H., Greiner, D., Shultz, L., and Lapidot, T. (2000). beta2 microglobulin-deficient (B2m(null)) NOD/SCID mice are excellent recipients for studying human stem cell function. Blood 95, 3102-3105.

Kollet, O., Spiegel, A., Peled, A., Petit, I., Byk, T., Hershkoviz, R., Guetta, E., Barkai, G., Nagler, A., and Lapidot, T. (2001). Rapid and efficient homing of human CD34(+) CD38(−/low)CXCR4(+) stem and progenitor cells to the bone marrow and spleen of NOD/SCID and NOD/SCID/B2m(null) mice. Blood 97, 3283-3291.

Kretschmer, K., Apostolou, I., Hawiger, D., Khazaie, K., Nussenzweig, M. C., and von Boehmer, H. (2005). Inducing and expanding regulatory T cell populations by foreign antigen. Nat Immunol 6, 1219-1227.

Kyewski, B., and Derbinski, J. (2004). Self-representation in the thymus: an extended view. Nat Rev Immunol 4, 688-698.

La Motte-Mohs, R. N., Awong, G., and Zúñiga-Pflücker, J. C. (2007). In Vitro Models of Human T Cell Development: Dishing Out Progenitor T Cells. Current Immunology Reviews 3, 57-75.

La Motte-Mohs, R. N., Herer, E., and Zúñiga-Pflücker, J. C. (2005). Induction of T-cell development from human cord blood hematopoietic stem cells by Delta-like 1 in vitro. Blood 105, 1431-1439.

Lai, A. Y., and Kondo, M. (2007). Identification of a bone marrow precursor of the earliest thymocytes in adult mouse. Proc Natl Acad Sci USA 104, 6311-6316.

Lapidot, T., Pflumio, F., Doedens, M., Murdoch, B., Williams, D. E., and Dick, J. E. (1992). Cytokine stimulation of multilineage hematopoiesis from immature human cells engrafted in SCID mice. Science 255, 1137-1141.

Lardelli, M., Dahlstrand, J., and Lendahl, U. (1994). The novel Notch homologue mouse Notch 3 lacks specific epidermal growth factor-repeats and is expressed in proliferating neuroepithelium. Mech Dev 46, 123-136.

Larochelle, A., Vormoor, J., Hanenberg, H., Wang, J. C., Bhatia, M., Lapidot, T., Moritz, T., Murdoch, B., Xiao, X. L., Kato, I., et al. (1996). Identification of primitive human hematopoietic cells capable of repopulating NOD/SCID mouse bone marrow: implications for gene therapy. Nat Med 2, 1329-1337.

Legrand, N., Weijer, K., and Spits, H. (2006). Experimental models to study development and function of the human immune system in vivo. J Immunol 176, 2053-2058.

Lehar, S. M., and Bevan, M. J. (2002). T cell development in culture. Immunity 17, 689-692.

Lewis, I. D., and Verfallie, C. M. (2000). Multi-lineage expansion potential of primitive hematopoietic progenitors: superiority of umbilical cord blood compared to mobilized peripheral blood. Exp Hematol 28, 1087-1095.

Li, L., Milner, L. A., Deng, Y., Iwata, M., Banta, A., Graf, L., Marcovina, S., Friedman, C., Trask, B. J., Hood, L., et al. (1998). The human homolog of rat Jagged1 expressed by marrow stroma inhibits differentiation of 32D cells through interaction with Notch1. Immunity 8, 43-55.

Lindley, S., Dayan, C. M., Bishop, A., Roep, B. O., Peakman, M., and Tree, T. I. (2005). Defective suppressor function in CD4(+)CD25(+) T-cells from patients with type 1 diabetes. Diabetes 54, 92-99.

Lindsell, C. E., Shawber, C. J., Boulter, J., and Weinmaster, G. (1995). Jagged: a mammalian ligand that activates Notch1. Cell 80, 909-917.

Luo, B., Aster, J. C., Hasserjian, R. P., Kuo, F., and Sklar, J. (1997). Isolation and functional analysis of a cDNA for human Jagged2, a gene encoding a ligand for the Notch1 receptor. Mol Cell Biol 17, 6057-6067.

MacDonald, H. R., Wilson, A., and Radtke, F. (2001). Notch1 and T-cell development: insights from conditional knockout mice. Trends Immunol 22, 155-160.

Markovic, I. (2006). Advances in HIV-1 Entry Inhibitors: Strategies to Interfere with Receptor and CoReceptor Engagement. Curr Pharm Des 12, 1105-1119.

Mazurier, F., Fontanellas, A., Salesse, S., Taine, L., Landriau, S., Moreau-Gaudry, F., Reiffers, J., Peault, B., Di Santo, J. P., and de Verneuil, H. (1999). A novel immunodeficient mouse model—RAG2 x common cytokine receptor gamma chain double mutants—requiring exogenous cytokine administration for human hematopoietic stem cell engraftment. J Interferon Cytokine Res 19, 533-541.

Mazurier, F., Gan, O. I., McKenzie, J. L., Doedens, M., and Dick, J. E. (2004). Lentivector-mediated clonal tracking reveals intrinsic heterogeneity in the human hematopoietic stem cell compartment and culture-induced stem cell impairment. Blood 103, 545-552.

McCune, J., Kaneshima, H., Krowka, J., Namikawa, R., Outzen, H., Peault, B., Rabin, L., Shih, C. C., Yee, E., Lieberman, M., et al. (1991). The SCID-hu mouse: a small animal model for HIV infection and pathogenesis. Annu Rev Immunol 9, 399-429.

McCune, J. M., Namikawa, R., Kaneshima, H., Shultz, L. D., Lieberman, M., and Weissman, I. L. (1988). The SCID-hu mouse: murine model for the analysis of human hematolymphoid differentiation and function. Science 241, 1632-1639.

McKenzie, J. L., Gan, O. I., Doedens, M., and Dick, J. E. (2005). Human short-term repopulating stem cells are efficiently detected following intrafemoral transplantation into NOD/SCID recipients depleted of CD122+ cells. Blood 106, 1259-1261.

McKenzie, J. L., Gan, O. I., Doedens, M., and Dick, J. E. (2007). Reversible cell surface expression of CD38 on CD34-positive human hematopoietic repopulating cells. Exp Hematol 35, 1429-1436.

McManus, M. T., and Sharp, P. A. (2002). Gene silencing in mammals by small interfering RNAs. Nat Rev Genet. 3, 737-747.

Merkenschlager, M., and Fisher, A. G. (1991). CD45 isoform switching precedes the activation-driven death of human thymocytes by apoptosis. Int Immunol 3, 1-7.

Michie, A. M., and Zúñiga-Pflücker, J. C. (2000). Transfection and transcription of genes in developing thymocytes. Methods Mol Biol 134, 55-62.

Milner, L. A., Bigas, A., Kopan, R., Brashem-Stein, C., Bernstein, I. D., and Martin, D. I. (1996). Inhibition of granulocytic differentiation by mNotch1. Proc Natl Acad Sci USA 93, 13014-13019.

Milner, L. A., Kopan, R., Martin, D. I., and Bernstein, I. D. (1994). A human homologue of the Drosophila developmental gene, Notch, is expressed in CD34+ hematopoietic precursors. Blood 83, 2057-2062.

Modlin, R. L., and Sieling, P. A. (2005). Immunology. Now presenting: gammadelta T cells. Science 309, 252-253.

Odorico, J. S., Kaufman, D. S., and Thomson, J. A. (2001). Multilineage differentiation from human embryonic stem cell lines. Stem Cells 19, 193-204.

Olsen, A. L., Stachura, D. L., and Weiss, M. J. (2006). Designer blood: creating hematopoietic lineages from embryonic stem cells. Blood 107, 1265-1275.

Osborne, B., and Miele, L. (1999). Notch and the immune system. Immunity 11, 653-663.

Outram, S. V., Varas, A., Pepicelli, C. V., and Crompton, T. (2000). Hedgehog signaling regulates differentiation from double-negative to double-positive thymocyte. Immunity 13, 187-197.

Pai, S. Y., Truitt, M. L., Ting, C. N., Leiden, J. M., Glimcher, L. H., and Ho, I. C. (2003). Critical roles for transcription factor GATA-3 in thymocyte development. Immunity 19, 863-875.

Payne, K. J., and Crooks, G. M. (2002). Human hematopoietic lineage commitment. Immunol Rev 187, 48-64.

Pear, W. S., Aster, J. C., Scott, M. L., Hasserjian, R. P., Soffer, B., Sklar, J., and Baltimore, D. (1996). Exclusive development of T cell neoplasms in mice transplanted with bone marrow expressing activated Notch alleles. J Exp Med 183, 2283-2291.

Pear, W. S., and Radtke, F. (2003). Notch signaling in lymphopoiesis. Semin Immunol 15, 69-79.

Peault, B., Weissman, I. L., Baum, C., McCune, J. M., and Tsukamoto, A. (1991). Lymphoid reconstitution of the human fetal thymus in SCID mice with CD34+ precursor cells. J Exp Med 174, 1283-1286.

Petropoulos, D., and Chan, K. W. (2005). Umbilical cord blood transplantation. Curr Oncol Rep 7, 406-409.

Plum, J., De Smedt, M., Defresne, M. P., Leclercq, G., and Vandekerckhove, B. (1994). Human CD34+ fetal liver stem cells differentiate to T cells in a mouse thymic microenvironment. Blood 84, 1587-1593.

Plum, J., De Smedt, M., Verhasselt, B., Kerre, T., Vanhecke, D., Vandekerckhove, B., and Leclercq, G. (2000). Human T lymphopoiesis. In vitro and in vivo study models. Ann N Y Acad Sci 917, 724-731.

Pongracz, J., Hare, K., Harman, B., Anderson, G., and Jenkinson, E. J. (2003). Thymic epithelial cells provide WNT signals to developing thymocytes. Eur J Immunol 33, 1949-1956.

Pui, J. C., Allman, D., Xu, L., DeRocco, S., Karnell, F. G., Bakkour, S., Lee, J. Y., Kadesch, T., Hardy, R. R., Aster, J. C., et al. (1999). Notch1 expression in early lymphopoiesis influences B versus T lineage determination. Immunity 11, 299-308.

Radtke, F., Wilson, A., Ernst, B., and MacDonald, H. R. (2002). The role of Notch signaling during hematopoietic lineage commitment. Immunol Rev 187, 65-74.

Radtke, F., Wilson, A., Mancini, S. J., and MacDonald, H. R. (2004). Notch regulation of lymphocyte development and function. Nat Immunol 5, 247-253.

Rawlings, D. J., Quan, S. G., Kato, R. M., and Witte, O. N. (1995). Long-term culture system for selective growth of human B-cell progenitors. Proc Natl Acad Sci USA 92, 1570-1574.

Renkvist, N., Castelli, C., Robbins, P. F., and Parmiani, G. (2001). A listing of human tumor antigens recognized by T cells. Cancer Immunol Immunother 50, 3-15.

Res, P., Blom, B., Hori, T., Weijer, K., and Spits, H. (1997). Downregulation of CD1 marks acquisition of functional maturation of human thymocytes and defines a control point in late stages of human T cell development. J Exp Med 185, 141-151.

Res, P., Martinez-Caceres, E., Cristina Jaleco, A., Staal, F., Noteboom, E., Weijer, K., and Spits, H. (1996). CD34+ CD38dim cells in the human thymus can differentiate into T, natural killer, and dendritic cells but are distinct from pluripotent stem cells. Blood 87, 5196-5206.

Res, P., and Spits, H. (1999). Developmental stages in the human thymus. Semin Immunol 11, 39-46.

Robey, E. (1999). Regulation of T cell fate by Notch. Annu Rev Immunol 17, 283-295.

Robey, E., Chang, D., Itano, A., Cado, D., Alexander, H., Lans, D., Weinmaster, G., and Salmon, P. (1996). An activated form of Notch influences the choice between CD4 and CD8 T cell lineages. Cell 87, 483-492.

Roncarolo, M. G., Bacchetta, R., Bordignon, C., Narula, S., and Levings, M. K. (2001). Type 1 T regulatory cells. Immunol Rev 182, 68-79.

Rosenberg, S. A., Restifo, N. P., Yang, J. C., Morgan, R. A., and Dudley, M. E. (2008). Adoptive cell transfer: a clinical path to effective cancer immunotherapy. Nat Rev Cancer 8, 299-308.

Rossi, F. M., Corbel, S. Y., Merzaban, J. S., Carlow, D. A., Gossens, K., Duenas, J., So, L., Yi, L., and Ziltener, H. J. (2005). Recruitment of adult thymic progenitors is regulated by P-selectin and its ligand PSGL-1. Nat Immunol 6, 626-634.

Rothenberg, E. V., and Taghon, T. (2005). Molecular genetics of T cell development. Annu Rev Immunol 23, 601-649.

Rugg-Gunn, P. J., Ferguson-Smith, A. C., and Pedersen, R. A. (2005). Epigenetic status of human embryonic stem cells. Nat Genet 37, 585-587.

Sakaguchi, S. (2005). Naturally arising Foxp3-expressing CD25+CD4+ regulatory T cells in immunological tolerance to self and non-self. Nat Immunol 6, 345-352.

Sakaguchi, S., Sakaguchi, N., Shimizu, J., Yamazaki, S., Sakihama, T., Itoh, M., Kuniyasu, Y., Nomura, T., Toda, M., and Takahashi, T. (2001). Immunologic tolerance maintained by CD25+ CD4+ regulatory T cells: their common role in controlling autoimmunity, tumor immunity, and transplantation tolerance. Immunol Rev 182, 18-32.

Samson, M., Libert, F., Doranz, B. J., Rucker, J., Liesnard, C., Farber, C. M., Saragosti, S., Lapoumeroulie, C., Cognaux, J., Forceille, C., et al. (1996). Resistance to HIV-1 infection in caucasian individuals bearing mutant alleles of the CCR-5 chemokine receptor gene. Nature 382, 722-725.

Sanchez, M. J., Muench, M. O., Roncarolo, M. G., Lanier, L. L., and Phillips, J. H. (1994). Identification of a common T/natural killer cell progenitor in human fetal thymus. J Exp Med 180, 569-576.

Sánchez, M. J., Spits, H., Lanier, L. L., and Phillips, J. H. (1993). Human natural killer cell committed thymocytes and their relation to the T cell lineage. J Exp Med 178, 1857-1866.

Schmitt, T. M., de Pooter, R. F., Gronski, M. A., Cho, S. K., Ohashi, P. S., and Zúñiga-Pflücker, J. C. (2004). Induction of T cell development and establishment of T cell competence from embryonic stem cells differentiated in vitro. Nat Immunol 5, 410-417.

Schmitt, T. M., and Zúñiga-Pflücker, J. C. (2002). Induction of T cell development from hematopoietic progenitor cells by delta-like-1 in vitro. Immunity 17, 749-756.

Schmitt, T. M., and Zúñiga-Pflücker, J. C. (2006). T-cell development, doing it in a dish. Immunol Rev 209, 95-102.

Schuldiner, M., Yanuka, O., Itskovitz-Eldor, J., Melton, D. A., and Benvenisty, N. (2000). Effects of eight growth factors on the differentiation of cells derived from human embryonic stem cells. Proc Natl Acad Sci USA 97, 11307-11312.

Schwarz, B. A., Sambandam, A., Maillard, I., Harman, B. C., Love, P. E., and Bhandoola, A. (2007). Selective thymus settling regulated by cytokine and chemokine receptors. J Immunol 178, 2008-2017.

Shah, D. K., Hager-Theodorides, A. L., Outram, S. V., Ross, S. E., Varas, A., and Crompton, T. (2004). Reduced thymocyte development in sonic hedgehog knockout embryos. J Immunol 172, 2296-2306.

Shortman, K., Egerton, M., Spangrude, G. J., and Scollay, R. (1990). The generation and fate of thymocytes. Semin Immunol 2, 3-12.

Shultz, L. D., Lang, P. A., Christianson, S. W., Gott, B., Lyons, B., Umeda, S., Leiter, E., Hesselton, R., Wagar, E. J., Leif, J. H., et al. (2000). NOD/LtSz-Raglnull mice: an immunodeficient and radioresistant model for engraftment of human hematolymphoid cells, HIV infection, and adoptive transfer of NOD mouse diabetogenic T cells. J Immunol 164, 2496-2507.

Shultz, L. D., Schweitzer, P. A., Christianson, S. W., Gott, B., Schweitzer, I. B., Tennent, B., McKenna, S., Mobraaten, L., Rajan, T. V., Greiner, D. L., et al. (1995). Multiple defects in innate and adaptive immunologic function in NOD/LtSz-scid mice. J Immunol 154, 180-191.

Shutter, J. R., Scully, S., Fan, W., Richards, W. G., Kitajewski, J., Deblandre, G. A., Kintner, C. R., and Stark, K. L. (2000). DII4, a novel Notch ligand expressed in arterial endothelium. Genes Dev 14, 1313-1318.

Slukvin, II, Vodyanik, M. A., Thomson, J. A., Gumenyuk, M. E., and Choi, K. D. (2006). Directed differentiation of human embryonic stem cells into functional dendritic cells through the myeloid pathway. J Immunol 176, 2924-2932.

Socie, G. (2005). Current issues in allogeneic stem cell transplantation. Hematology 10 *Suppl* 1, 63.

Spits, H. (2002). Development of alphabeta T cells in the human thymus. Nat Rev Immunol 2, 760-772.

Spits, H., Couwenberg, F., Bakker, A. Q., Weijer, K., and Uittenbogaart, C. H. (2000). Id2 and Id3 inhibit development of CD34(+) stem cells into predendritic cell (pre-DC)$_2$ but not into pre-DC1. Evidence for a lymphoid origin of pre-DC2. J Exp Med 192, 1775-1784.

Spits, H., Lanier, L. L., and Phillips, J. H. (1995). Development of human T and natural killer cells. Blood 85, 2654-2670.

Staal, F. J., Weerkamp, F., Baert, M. R., van den Burg, C. M., van Noort, M., de Haas, E. F., and van Dongen, J. J. (2004). Wnt target genes identified by DNA microarrays in immature CD34+ thymocytes regulate proliferation and cell adhesion. J Immunol 172, 1099-1108.

Stier, S., Cheng, T., Dombkowski, D., Carlesso, N., and Scadden, D. T. (2002). Notch1 activation increases hematopoietic stem cell self-renewal in vivo and favors lymphoid over myeloid lineage outcome. Blood 99, 2369-2378.

Su, L., Lee, R., Bonyhadi, M., Matsuzaki, H., Forestell, S., Escaich, S., Bohnlein, E., and Kaneshima, H. (1997). Hematopoietic stem cell-based gene therapy for acquired immunodeficiency syndrome: efficient transduction and expression of RevM10 in myeloid cells in vivo and in vitro. Blood 89, 2283-2290.

Sykes, M., and Nikolic, B. (2005). Treatment of severe autoimmune disease by stem-cell transplantation. Nature 435, 620-627.

Tai, X., Cowan, M., Feigenbaum, L., and Singer, A. (2005). CD28 costimulation of developing thymocytes induces Foxp3 expression and regulatory T cell differentiation independently of interleukin 2. Nat Immunol 6, 152-162.

Takahama, Y. (2000). Differentiation of mouse thymocytes in fetal thymus organ culture. Methods Mol Biol 134, 37-46.

Terstappen, L. W., Huang, S., and Picker, L. J. (1992). Flow cytometric assessment of human T-cell differentiation in thymus and bone marrow. Blood 79, 666-677.

Thomsen, M., Yacoub-Youssef, H., and Marcheix, B. (2005). Reconstitution of a human immune system in immunodeficient mice: models of human alloreaction in vivo. Tissue Antigens 66, 73-82.

Tian, X., Woll, P. S., Morris, J. K., Linehan, J. L., and Kaufman, D. S. (2006). Hematopoietic engraftment of human embryonic stem cell-derived cells is regulated by recipient innate immunity. Stem Cells 24, 1370-1380.

Timmermans, F., Velghe, I., Vanwalleghem, L., De Smedt, M., Van Coppernolle, S., Taghon, T., Moore, H. D., Leclercq, G., Langerak, A. W., Kerre, T., et al. (2009). Generation of T cells from human embryonic stem cell-derived hematopoietic zones. J Immunol 182, 6879-6888.

Touraine, J. L., Roncarolo, M. G., Raudrant, D., Bacchetta, R., Golfier, F., Sembeil, R., and Gebuhrer, L. (2005). Induction of transplantation tolerance in humans using fetal cell transplants. Transplant Proc 37, 65-66.

Traggiai, E., Chicha, L., Mazzucchelli, L., Bronz, L., Piffaretti, J. C., Lanzavecchia, A., and Manz, M. G. (2004). Development of a human adaptive immune system in cord blood cell-transplanted mice. Science 304, 104-107.

Uyttendaele, H., Marazzi, G., Wu, G., Yan, Q., Sassoon, D., and Kitajewski, J. (1996). Notch4/int-3, a mammary protooncogene, is an endothelial cell-specific mammalian Notch gene. Development 122, 2251-2259.

van Baarle, D., Kostense, S., van Oers, M. H., Hamann, D., and Miedema, F. (2002). Failing immune control as a result of impaired CD8+ T-cell maturation: CD27 might provide a clue. Trends Immunol 23, 586-591.

van den Brink, M. R., Alpdogan, O., and Boyd, R. L. (2004). Strategies to enhance T-cell reconstitution in immunocompromised patients. Nat Rev Immunol 4, 856-867.

Vanhecke, D., Leclercq, G., Plum, J., and Vandekerckhove, B. (1995). Characterization of distinct stages during the differentiation of human CD69+CD3+ thymocytes and identification of thymic emigrants. J Immunol 155, 1862-1872.

Vanhecke, D., Verhasselt, B., De Smedt, M., De Paepe, B., Leclercq, G., Plum, J., and Vandekerckhove, B. (1997). MHC class II molecules are required for initiation of positive selection but not during terminal differentiation of human CD4 single positive thymocytes. J Immunol 158, 3730-3737.

Varnum-Finney, B., Purton, L. E., Yu, M., Brashem-Stein, C., Flowers, D., Staats, S., Moore, K. A., Le Roux, I., Mann, R., Gray, G., et al. (1998). The Notch ligand, Jagged-1, influences the development of primitive hematopoietic precursor cells. Blood 91, 4084-4091.

Viglietta, V., Baecher-Allan, C., Weiner, H. L., and Hafler, D. A. (2004). Loss of functional suppression by CD4+CD25+ regulatory T cells in patients with multiple sclerosis. J Exp Med 199, 971-979.

Vila-Coro, A. J., Mellado, M., Martin de Ana, A., Lucas, P., del Real, G., Martinez, A. C., and Rodriguez-Frade, J. M. (2000). HIV-1 infection through the CCR5 receptor is blocked by receptor dimerization. Proc Natl Acad Sci USA 97, 3388-3393.

Vodyanik, M. A., Bork, J. A., Thomson, J. A., and Slukvin, II (2005). Human embryonic stem cell-derived CD34+ cells: efficient production in the coculture with OP9 stromal cells and analysis of lymphohematopoietic potential. Blood 105, 617-626.

von Boehmer, H. (2001). Coming to grips with Notch. J Exp Med 194, F43-46.

Vormoor, J., Lapidot, T., Pflumio, F., Risdon, G., Patterson, B., Broxmeyer, H. E., and Dick, J. E. (1994). Immature human cord blood progenitors engraft and proliferate to high levels in severe combined immunodeficient mice. Blood 83, 2489-2497.

Walker, L., Lynch, M., Silverman, S., Fraser, J., Boulter, J., Weinmaster, G., and Gasson, J. C. (1999). The Notch/Jagged pathway inhibits proliferation of human hematopoietic progenitors in vitro. Stem Cells 17, 162-171.

Walker, M. R., Kasprowicz, D. J., Gersuk, V. H., Benard, A., Van Landeghen, M., Buckner, J. H., and Ziegler, S. F. (2003). Induction of FoxP3 and acquisition of T regulatory activity by stimulated human CD4+CD25− T cells. J Clin Invest 112, 1437-1443.

Wang, H., and Spangrude, G. J. (2003). Aspects of early lymphoid commitment. Curr Opin Hematol 10, 203-207.

Wang, L., Li, L., Shojaei, F., Levac, K., Cerdan, C., Menendez, P., Martin, T., Rouleau, A., and Bhatia, M. (2004). Endothelial and hematopoietic cell fate of human embryonic stem cells originates from primitive endothelium with hemangioblastic properties. Immunity 21, 31-41.

Wang, L., Menendez, P., Cerdan, C., and Bhatia, M. (2005a). Hematopoietic development from human embryonic stem cell lines. Exp Hematol 33, 987-996.

Wang, L., Menendez, P., Shojaei, F., Li, L., Mazurier, F., Dick, J. E., Cerdan, C., Levac, K., and Bhatia, M. (2005b). Generation of hematopoietic repopulating cells from human embryonic stem cells independent of ectopic HOXB4 expression. J Exp Med 201, 1603-1614.

Washburn, T., Schweighoffer, E., Gridley, T., Chang, D., Fowlkes, B. J., Cado, D., and Robey, E. (1997). Notch activity influences the alphabeta versus gammadelta T cell lineage decision. Cell 88, 833-843.

Watanabe, N., Wang, Y. H., Lee, H. K., Ito, T., Wang, Y. H., Cao, W., and Liu, Y. J. (2005). Hassall's corpuscles instruct dendritic cells to induce CD4+CD25+ regulatory T cells in human thymus. Nature 436, 1181-1185.

Weerkamp, F., Baert, M. R., Brugman, M. H., Dik, W. A., de Haas, E. F., Visser, T. P., de Groot, C. J., Wagemaker, G., van Dongen, J. J., and Staal, F. J. (2006a). Human thymus contains multipotent progenitors with T/B lymphoid, myeloid, and erythroid lineage potential. Blood 107, 3131-3137.

Weerkamp, F., Baert, M. R., Naber, B. A., Koster, E. E., de Haas, E. F., Atkuri, K. R., van Dongen, J. J., Herzenberg, L. A., and Staal, F. J. (2006b). Wnt signaling in the thymus is regulated by differential expression of intracellular signaling molecules. Proc Natl Acad Sci USA 103, 3322-3326.

Weerkamp, F., Pike-Overzet, K., and Staal, F. J. (2006c). T-sing progenitors to commit. Trends Immunol 27, 125-131.

Weerkamp, F., van Dongen, J. J., and Staal, F. J. (2006d). Notch and Wnt signaling in T-lymphocyte development and acute lymphoblastic leukemia. Leukemia 20, 1197-1205.

Weiner, H. L. (2001). Induction and mechanism of action of transforming growth factor-beta-secreting Th3 regulatory cells. Immunol Rev 182, 207-214.

Weinmaster, G., Roberts, V. J., and Lemke, G. (1991). A homolog of Drosophila Notch expressed during mammalian development. Development 113, 199-205.

Weng, A. P., Ferrando, A. A., Lee, W., Morris, J. P. t., Silverman, L. B., Sanchez-Irizarry, C., Blacklow, S. C., Look, A. T., and Aster, J. C. (2004). Activating mutations of NOTCH1 in human T cell acute lymphoblastic leukemia. Science 306, 269-271.

Williams, G. T., Kingston, R., Owen, M. J., Jenkinson, E. J., and Owen, J. J. (1986). A single micromanipulated stem cell gives rise to multiple T-cell receptor gene rearrangements in the thymus in vitro. Nature 324, 63-64.

Wilpshaar, J., Bhatia, M., Kanhai, H. H., Breese, R., Heilman, D. K., Johnson, C. S., Falkenburg, J. H., and Srour, E. F. (2002). Engraftment potential of human fetal hematopoietic cells in NOD/SCID mice is not restricted to mitotically quiescent cells. Blood 100, 120-127.

Wilson, A., MacDonald, H. R., and Radtke, F. (2001). Notch 1-deficient common lymphoid precursors adopt a B cell fate in the thymus. J Exp Med 194, 1003-1012.

Woll, P. S., Martin, C. H., Miller, J. S., and Kaufman, D. S. (2005). Human embryonic stem cell-derived NK cells acquire functional receptors and cytolytic activity. J Immunol 175, 5095-5103.

Yeoman, H., Gress, R. E., Bare, C. V., Leary, A. G., Boyse, E. A., Bard, J., Shultz, L. D., Harris, D. T., and DeLuca, D. (1993). Human bone marrow and umbilical cord blood cells generate CD4+ and CD8+ single-positive T cells in murine fetal thymus organ culture. Proc Natl Acad Sci USA 90, 10778-10782.

Zakrzewski, J. L., Kochman, A. A., Lu, S. X., Terwey, T. H., Kim, T. D., Hubbard, V. M., Muriglan, S. J., Suh, D., Smith, M. O., Grubin, J., et al. (2006a). Adoptive transfer of in vitro generated T-cell precursors enhances T-cell reconstitution after allogeneic hematopoietic stem cell transplantation. Nat. Med.

Zakrzewski, J. L., Kochman, A. A., Lu, S. X., Terwey, T. H., Kim, T. D., Hubbard, V. M., Muriglan, S. J., Suh, D., Smith, O. M., Grubin, J., et al. (2006b). Adoptive transfer of T-cell precursors enhances T-cell reconstitution after allogeneic hematopoietic stem cell transplantation. Nat Med 12, 1039-1047.

Zakrzewski, J. L., Suh, D., Markley, J. C., Smith, O. M., King, C., Goldberg, G. L., Jenq, R., Holland, A. M., Grubin, J., Cabrera-Perez, J., et al. (2008). Tumor immunotherapy across MHC barriers using allogeneic T-cell precursors. Nat Biotech 26, 453-461.

Zambidis, E. T., Péault, B., Park, T. S., Bunz, F., and Civin, C. I. (2005). Hematopoietic differentiation of human embryonic stem cells progresses through sequential hematoendothelial, primitive, and definitive stages resembling human yolk sac development. Blood 106, 860-870.

Zhan, X., Dravid, G., Ye, Z., Hammond, H., Shamblott, M., Gearhart, J., and Cheng, L. (2004). Functional antigen-presenting leucocytes derived from human embryonic stem cells in vitro. Lancet 364, 163-171.

Zúñiga-Pflücker, J. C. (2004). T-cell development made simple. Nat Rev Immunol 4, 67-72.

The invention claimed is:

1. A method of producing a $CD34^+CD7^+CDS^+CD1a^-$ progenitor T cell (pro T cell) comprising (a) culturing a mammalian hematopoietic stem cell (HSC) with a stromal cell that express a Notch ligand in a medium comprising Flt-3L and IL-7; and (b) determining the presence of $CD34^+CD7^+CD5^+CD1a^-$ pro-T cells in the culture.

2. The method of claim 1 wherein the HSC is a human HSC.

3. The method according to claim 1 wherein the Notch ligand is DL1 or DL4.

4. The method of claim 3 wherein the cell expressing the Notch ligand is an OP-9 cell.

5. A method for increasing the number of T cells in a mammal comprising administering to a mammal an effective amount of a purified human progenitor T cell having a phenotype $CD34^+CD7^+CD5^+CD1a^-$, wherein the human progenitor T cell is isolated according to the method of claim 1, wherein an increase in $CD7^+CD5^+CD1a^+$ pro-T cells and cells of a later T-cell developmental stage is seen.

6. The method according to claim 5 wherein the mammal has cancer.

7. The method according to claim 5 wherein the mammal has HIV/AIDS.

8. The method according to claim 5 wherein the mammal has an autoimmune disease.

9. The method according to claim 5 wherein the progenitor T cell contains a heterologous gene.

* * * * *